United States Patent
McCarthy et al.

(10) Patent No.: US 10,660,778 B2
(45) Date of Patent: May 26, 2020

(54) SYSTEMS AND METHODS FOR ENABLING PASSAGE OF AN INTRAGASTRIC DEVICE

(71) Applicant: Obalon Therapeutics, Inc., Carlsbad, CA (US)

(72) Inventors: Eleanor McCarthy, Oceanside, CA (US); Mark C. Brister, Encinitas, CA (US); Antonio C. Llevares, Chula Vista, CA (US); Betty Wong, San Diego, CA (US)

(73) Assignee: Obalon Therapeutics, Inc., Carlsbad, CA (US)

( * ) Notice: Subject to any disclaimer, the term of this patent is extended or adjusted under 35 U.S.C. 154(b) by 41 days.

(21) Appl. No.: 15/623,175

(22) Filed: Jun. 14, 2017

(65) Prior Publication Data

US 2017/0367863 A1  Dec. 28, 2017

Related U.S. Application Data

(60) Provisional application No. 62/355,806, filed on Jun. 28, 2016.

(51) Int. Cl.
*A61F 5/00* (2006.01)

(52) U.S. Cl.
CPC ............ *A61F 5/003* (2013.01); *A61F 5/0036* (2013.01); *A61F 5/0083* (2013.01)

(58) Field of Classification Search
CPC .... A61F 5/0003; A61F 5/0013; A61F 5/0026; A61F 5/003; A61F 5/0036; A61F 5/0083; A61B 17/42; A61B 2017/4216; A61B 2017/4225; A61B 2017/4233; A61B 17/12022; A61B 17/1214; A61B 2017/00929; A61B 2017/12068; A61B 2017/1209
USPC ......................................................... 606/191
See application file for complete search history.

(56) References Cited

U.S. PATENT DOCUMENTS

| | | | | |
|---|---|---|---|---|
| 3,800,584 | A | * 4/1974 | Edwards, Sr. | ........ H01R 43/042 29/751 |
| 5,827,269 | A | * 10/1998 | Saadat | ................... A61B 18/00 606/28 |
| 8,864,840 | B2 | 10/2014 | Dominguez et al. | |
| 2002/0151885 | A1 * | 10/2002 | Underwood | ....... A61B 18/1206 606/41 |
| 2006/0058829 | A1 * | 3/2006 | Sampson | ................ A61F 5/003 606/192 |
| 2006/0111777 | A1 * | 5/2006 | Chen | ......................... A61F 2/12 623/8 |
| 2006/0155322 | A1 * | 7/2006 | Sater | ................ A61B 17/12022 606/200 |

(Continued)

FOREIGN PATENT DOCUMENTS

| | | |
|---|---|---|
| WO | WO 2009-002855 A2 | 12/2008 |
| WO | WO 2015-079322 A2 | 6/2015 |

*Primary Examiner* — Eric J Rosen
*Assistant Examiner* — Andrew P. Restaino
(74) *Attorney, Agent, or Firm* — Knobbe, Martens, Olson & Bear, LLP

(57) ABSTRACT

Devices and methods for treating obesity are provided. More particularly, intragastric devices and methods of fabricating, deploying, inflating, monitoring, and retrieving the same are provided. More particularly, apparatuses and methods for enabling volume-occupying intragastric devices to pass through the digestive system are provided.

19 Claims, 3 Drawing Sheets

(56) References Cited

U.S. PATENT DOCUMENTS

| | | | |
|---|---|---|---|
| 2007/0212559 A1* | 9/2007 | Shah | A61F 5/0003 428/473.5 |
| 2008/0243071 A1* | 10/2008 | Quijano | A61F 5/0003 604/103.02 |
| 2009/0131968 A1* | 5/2009 | Birk | A61F 5/003 606/192 |
| 2011/0307075 A1 | 12/2011 | Sharma | |
| 2012/0296365 A1* | 11/2012 | Nguyen | A61F 5/0036 606/192 |
| 2013/0138132 A1* | 5/2013 | Phee | A61F 5/0046 606/192 |
| 2014/0288535 A1* | 9/2014 | Raven | A61F 5/004 604/891.1 |
| 2015/0196408 A1* | 7/2015 | Moss | A61F 5/003 606/192 |

* cited by examiner

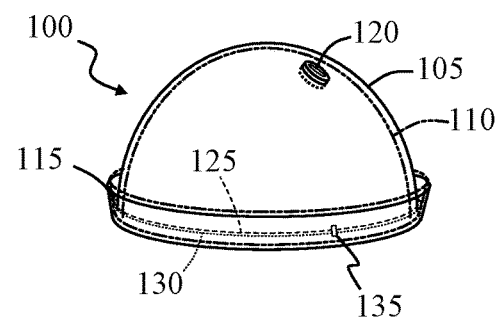
*FIGURE 1*
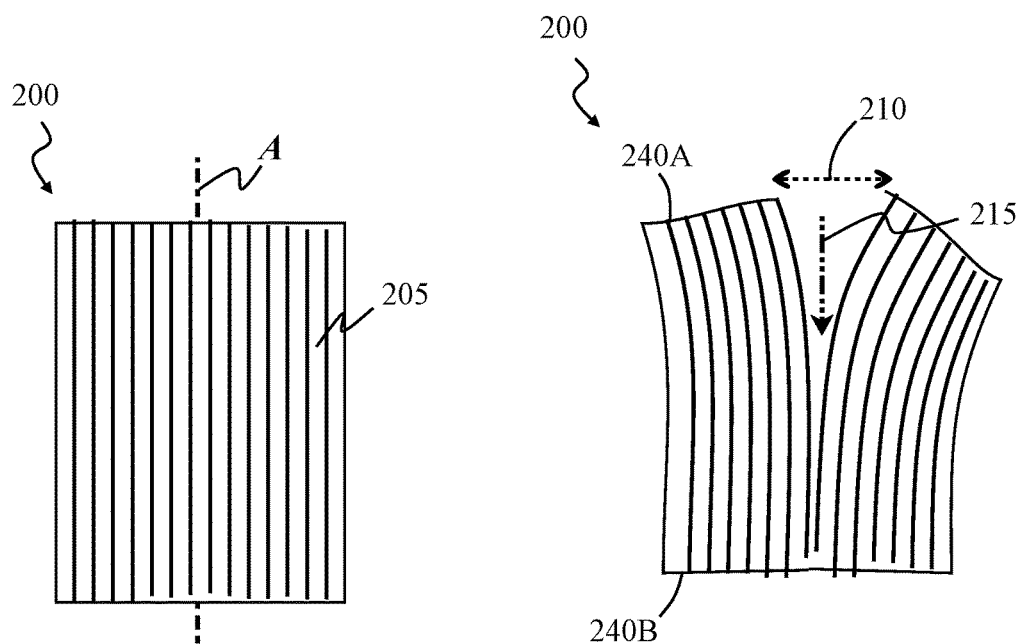
*FIGURE 2*            *FIGURE 3*

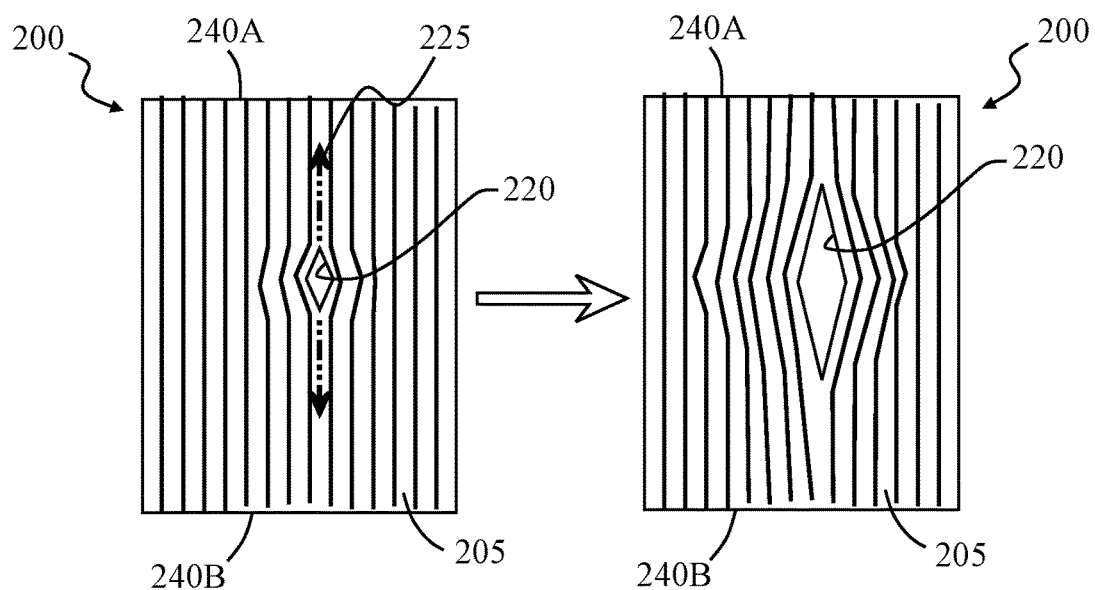
*FIGURE 4A*  *FIGURE 4B*
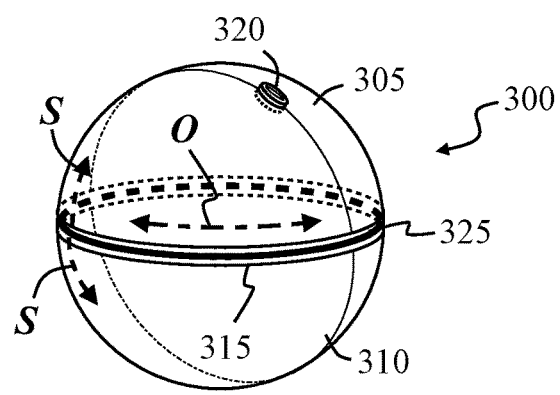
*FIGURE 5*

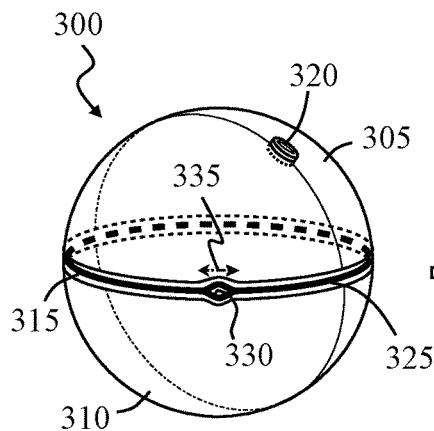
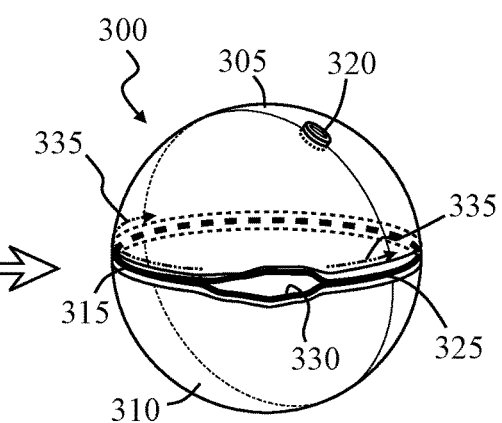
FIGURE 6A    FIGURE 6B
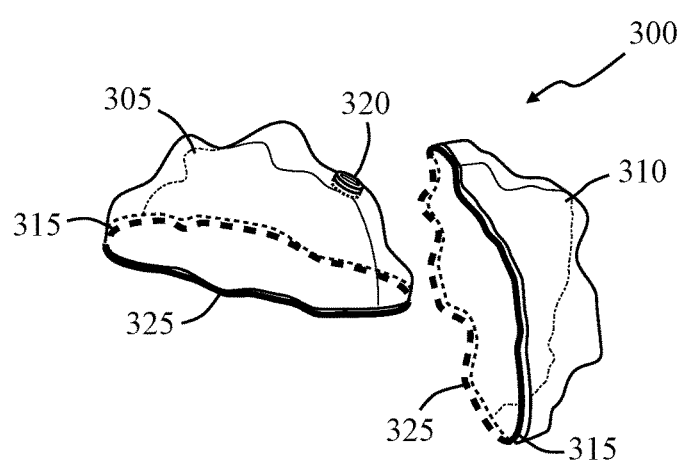
FIGURE 7

SYSTEMS AND METHODS FOR ENABLING PASSAGE OF AN INTRAGASTRIC DEVICE

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Application No. 62/355,806, filed Jun. 28, 2016. The aforementioned application is incorporated by reference herein in its entirety, and is hereby expressly made a part of this specification.

FIELD OF THE INVENTION

Devices and methods for treating obesity are provided. More particularly, apparatuses and methods for enabling volume-occupying intragastric devices to pass through the digestive system are provided.

BACKGROUND

Obesity is a major health problem in developed countries. Obesity puts you at greater risk of developing high blood pressure, diabetes and many other serious health problems. In the United States, the complications of being overweight or obese are estimated to affect nearly one in three American adults, with an annual medical cost of over $80 billion and, including indirect costs such as lost wages, a total annual economic cost of over $120 billion. Except for rare pathological conditions, weight gain is directly correlated to overeating.

Noninvasive methods for reducing weight include increasing metabolic activity to burn calories and/or reducing caloric intake, either by modifying behavior or with pharmacological intervention to reduce the desire to eat. Other methods include surgery to reduce the stomach's volume, banding to limit the size of the stoma, and intragastric devices that reduce the desire to eat by occupying space in the stomach.

Intragastric volume-occupying devices provide the patient a feeling of satiety after having eaten only small amounts of food. Thus, the caloric intake is diminished while the person is satisfied with a feeling of fullness. Currently available volume-occupying devices have many shortcomings. For example, complex gastric procedures are required to insert some devices.

U.S. Pat. No. 4,133,315, the contents of which are incorporated herein by reference in their entirety, discloses an apparatus for reducing obesity comprising an inflatable, elastomeric bag and tube combination. The bag can be inserted into the patient's stomach by swallowing. The end of the attached tube distal to the bag remains in the patient's mouth. A second tube is snaked through the nasal cavity and into the patient's mouth. The tube ends located in the patient's mouth are connected to form a continuous tube for fluid communication through the patient's nose to the bag. Alternatively, the bag can be implanted by a gastric procedure. The bag is inflated through the tube to a desired degree before the patient eats so that the desire for food is reduced. After the patient has eaten, the bag is deflated. The tube extends out of the patient's nose or abdominal cavity throughout the course of treatment.

U.S. Pat. Nos. 5,259,399, 5,234,454 and 6,454,785, the contents of which are incorporated herein by reference in their entirety, disclose intragastric volume-occupying devices for weight control that must be implanted surgically.

U.S. Pat. Nos. 4,416,267, 4,485,805, 4,607,618, 4,694,827, 4,723,547, 4,739,758, and 4,899,747 and European Pat. No. 246,999, the contents of which are incorporated herein by reference in their entirety, relate to intragastric, volume-occupying devices for weight control that can be inserted endoscopically. Of these, U.S. Pat. Nos. 4,416,267, 4,694,827, 4,739,758 and 4,899,747, the contents of which are incorporated herein by reference in their entirety relate to balloons whose surface is contoured in a certain way to achieve a desired end. In U.S. Pat. Nos. 4,416,267 and 4,694,827, the contents of which are incorporated herein by reference in their entirety, the balloon is torus-shaped with a flared central opening to facilitate passage of solids and liquids through the stomach cavity. The balloon of U.S. Pat. No. 4,694,827, the contents of which are incorporated herein by reference in their entirety, has a plurality of smooth-surfaced convex protrusions. The protrusions reduce the amount of surface area which contacts the stomach wall, thereby reducing the deleterious effects resulting from excessive contact with the gastric mucosa. The protrusions also define channels between the balloon and stomach wall through which solids and liquids may pass. The balloon of U.S. Pat. No. 4,739,758, the contents of which are incorporated herein by reference in their entirety, has blisters on its periphery that prevent it from seating tightly against the cardia or pylorus.

The balloons of U.S. Pat. Nos. 4,899,747 and 4,694,827, the contents of which are incorporated herein by reference in their entirety, are inserted by pushing the deflated balloon and releasably attached tubing down a gastric tube. U.S. Pat. No. 4,723,547, the contents of which are incorporated herein by reference in their entirety discloses a specially adapted insertion catheter for positioning its balloon. In U.S. Pat. No. 4,739,758, the contents of which are incorporated herein by reference in their entirety, the filler tube effects insertion of the balloon. In U.S. Pat. No. 4,485,805, the contents of which are incorporated herein by reference in their entirety, the balloon is inserted into a finger cot that is attached by string to the end of a conventional gastric tube that is inserted down the patient's throat. The balloon of European Pat. No. 246,999 is inserted using a gastroscope with integral forceps.

In U.S. Pat. Nos. 4,416,267, 4,485,805, 4,694,827, 4,739,758, and 4,899,747 and European Pat. No. 246,999, the contents of which are incorporated herein by reference in their entirety, the balloon is inflated with a fluid from a tube extending down from the patient's mouth. In these patents, the balloon also is provided with a self-sealing hole (U.S. Pat. No. 4,694,827, the contents of which are incorporated herein by reference in their entirety), injection site (U.S. Pat. Nos. 4,416,267 and 4,899,747, the contents of which are incorporated herein by reference in their entirety), self-sealing fill valve (U.S. Pat. No. 4,485,805, the contents of which are incorporated herein by reference in their entirety), self-closing valve (European Patent No. 246,999, the contents of which are incorporated herein by reference in their entirety) or duck-billed valve (U.S. Pat. No. 4,739,758, the contents of which are incorporated herein by reference in their entirety). U.S. Pat. No. 4,723,547, the contents of which are incorporated herein by reference in their entirety, uses an elongated thick plug and the balloon is filled by inserting a needle attached to an air source through the plug.

U.S. Pat. No. 4,607,618, the contents of which are incorporated herein by reference in their entirety, describes a collapsible appliance formed of semi-rigid skeleton members joined to form a collapsible hollow structure. The appliance is not inflatable. It is endoscopically inserted into the stomach using an especially adapted bougie having an ejector rod to release the collapsed appliance. Once released, the appliance returns to its greater relaxed size and shape.

U.S. Pat. No. 5,129,915, the contents of which are incorporated herein by reference in their entirety, relates to an intragastric balloon that is intended to be swallowed and that inflates automatically under the effect of temperature. Three ways that an intragastric balloon might be inflated by a change in temperature are discussed. A composition comprising a solid acid and non-toxic carbonate or bicarbonate is separated from water by a coating of chocolate, cocoa paste or cocoa butter that melts at body temperature. Alternatively, citric acid and an alkaline bicarbonate coated with non-toxic vegetable or animal fat melting at body temperature and which placed in the presence of water, can produce the same result. Lastly, the solid acid and non-toxic carbonate or bicarbonate are isolated from water by an isolation pouch of low-strength synthetic material which it will suffice to break immediately before swallowing the bladder. Breaking the isolation pouches causes the acid, carbonate or bicarbonate and water to mix and the balloon to begin to expand immediately. A drawback of thermal triggering of inflation is that it does not afford the degree of control and reproducibility of the timing of inflation that is desirable and necessary in a safe self-inflating intragastric balloon.

After swallowing, food and oral medicaments typically reach a patient's stomach in under a minute. Food is retained in the stomach on average from one to three hours. However, the residence time is highly variable and dependent upon such factors as the fasting or fed state of the patient. Accordingly, proper timing of inflation of an intragastric balloon is a factor in successful deployment of the intragastric devices of various embodiments. Timing is selected to avoid premature inflation in the esophagus that could lead to an esophageal obstruction or belated inflation that could lead to intestinal obstruction. Similarly, controlled deflation of intragastric balloons is desirable to avoid intestinal obstruction.

SUMMARY OF THE INVENTION

Intragastric volume-occupying devices may deflate or deteriorate, due to failure of the gastric volume-occupying device or as an intended mechanism to facilitate passage of the gastric volume-occupying device through the digestive system after use in the stomach. If an intragastric volume-occupying device is insufficiently deflated or if a quantity of liquid becomes trapped in a deflating or deflated intragastric volume-occupying device, the intragastric volume occupying device may cause an intestinal blockage requiring exploratory surgery. Accordingly, apparatuses and methods to facilitate passage of an intragastric volume-occupying device through the digestive system are provided.

A free-floating intragastric volume-occupying device that maintains its volume and/or internal pressure within a predetermined range over time, or which undergoes a predetermined adjustment in volume and/or internal pressure over time, is disclosed. By maintaining a predetermined volume and/or internal pressure, stresses on the device leading to a breach in structural integrity can be minimized, which prevents premature and/or uncontrolled deflation or other device failure. By undergoing a predetermined adjustment in volume and/or internal pressure over time, a preselected volume profile can be obtained to accommodate changes in stomach size over the course of treatment with the device.

The devices can be self-inflating (also referred to as automatic inflating) or inflatable (also referred to as manually inflating via a tether). The devices can also be self-deflating (also referred to as automatic deflating) or deflatable (also referred to as manually deflating).

Volume-occupying devices and methods for manufacturing, deploying, inflating, tracking, locating, deflating and retrieving of such devices are provided. The devices and methods of the preferred embodiments may be employed for treating over weight and obese individuals. Methods employing the device of the preferred embodiments need not utilize invasive procedures, but rather the device may simply be swallowed by a patient, with or without a catheter attached. Once in the stomach of the patient, the device is inflated with a preselected fluid, e.g., a gas, liquid, vapor or mixtures thereof, to a preselected volume. Therefore, the use of one fluid, such as a "gas", e.g., an initial fill gas, to describe the various embodiments herein, does not preclude the use of other fluids as well. Further, a "fluid," such as an initial fill fluid, also includes a material or materials in the solid, liquid, vapor, or gas phase that are incorporated within, mixed within, carried within or otherwise entrained in a fluid such as a gas or liquid. A fluid can comprise one substance, or mixtures of different substances, and may be or include saline, physiologically acceptable fluids or substances, etc. as further described herein. The wall of the device is preselected for its particular fluid, e.g. gas, diffusion properties. Once in the in vivo environment, the gas(es) within the device diffuse out through the wall of the device, and gases diffuse into the device from the in vivo environment. By preselecting the device wall and gas(es) initially employed to inflate the device, taking into account diffusion properties of gases into the device from the in vivo environment, the volume and/or internal pressure of the device can be maintained within a preselected range, or can follow a preselected profile of volume and/or pressure changes. After a predetermined time period, the device can be removed using endoscopic tools or will decrease in volume or deflate so as to pass through the remainder of the patient's digestive tract.

Inflation may be achieved by use of a removable catheter that initially remains in fluid contact with the device after it has been swallowed by the patient. Alternatively, inflation may be achieved by a self-inflation process, e.g., generation of gas in the device once it reaches the stomach by reaction of gas-generating components contained within the device upon swallowing, or by introduction of one or more components in the gas generating process into the device by use of a removable catheter.

The volume-occupying subcomponent of devices may be formed by injection, blow or rotational molding of a flexible, gas-impermeable, biocompatible material, such as, for example, polyurethane, nylon or polyethylene terephthalate. Materials that may be used to control the gas permeability/impermeability of the volume-occupying subcomponent include, but are not limited to, silicon oxide (SiOx), gold or any noble metal, saran, conformal coatings and the like, when it is desired to reduce permeability. To enhance gas-impermeable characteristics of the wall of the device, if desirable, the volume-occupying subcomponent may be further coated with one or more gas-barrier compounds, or be formed of a Mylar polyester film coating or kelvalite, silver or aluminum as a metalized surface to provide a gas impermeable barrier.

In further embodiments, the device employs a delivery state in which the device is packaged such that the device may be swallowed while producing minimal discomfort to the patient. In a delivery state, the device may be packaged into a capsule. Alternatively, the device may be coated with a material operable to confine the device and facilitate swallowing. Various techniques may also be employed to ease swallowing of the device including, for example, wetting, temperature treating, lubricating, and treating with pharmaceuticals such as anesthetics.

The gastric volume-occupying device incorporates a component or components that facilitate passage out of the stomach and through the digestive system. The component or components may facilitate one or both of rapid deflation of the volume-occupying device and breakage of the gastric volume-occupying device into a plurality of separate pieces. Deflation and/or breakage of the gastric volume-occupying device can be automatic or manually initiated, and may be triggered by a failure or partial failure of the gastric volume-occupying device. The component or components can be incorporated into the gastric volume-occupying device or a component thereof or therein, or can be provided as an additional component added to or affixed to the gastric volume-occupying device or a component thereof or therein.

In a generally applicable first aspect (i.e. independently combinable with any of the aspects or embodiments identified herein), an intragastric balloon system is provided, the system comprising: an intragastric balloon; at least two wires in communication with a surface of a wall of the intragastric balloon; and an electronics package configured to facilitate a supply of current to the at least two wires.

In an embodiment of the first aspect, which is generally applicable (i.e., independently combinable with any of the aspects or embodiments identified herein), the electronics package is configured to complete a circuit between the at least two wires.

In an embodiment of the first aspect, which is generally applicable (i.e., independently combinable with any of the aspects or embodiments identified herein), the electronics package comprises a switch, wherein the electronics package is configured to complete a circuit between the least two wires by activating the switch.

In an embodiment of the first aspect, which is generally applicable (i.e., independently combinable with any of the aspects or embodiments identified herein), the at least two wires comprise a copper wire and an aluminum wire, wherein the system further comprises a saline solution in communication with the at least two wires.

In an embodiment of the first aspect, which is generally applicable (i.e., independently combinable with any of the aspects or embodiments identified herein), the at least two wires are embedded within a weld of the balloon.

In an embodiment of the first aspect, which is generally applicable (i.e., independently combinable with any of the aspects or embodiments identified herein), the electronics package comprises a timer, wherein the electronics package is configured to facilitate the supply of current to the at least two wires at a predetermined time or after a predetermined amount of time.

In an embodiment of the first aspect, which is generally applicable (i.e., independently combinable with any of the aspects or embodiments identified herein), the electronics package further comprises a communications module, the communications module configured to receive data from an external device.

In an embodiment of the first aspect, which is generally applicable (i.e., independently combinable with any of the aspects or embodiments identified herein), the electronics package is configured to receive an instruction to initiate the supply of current to the at least two wires from the external device.

In an embodiment of the first aspect, which is generally applicable (i.e., independently combinable with any of the aspects or embodiments identified herein), the intragastric balloon comprises a uni-directional polymer film.

In a generally applicable second aspect (i.e. independently combinable with any of the aspects or embodiments identified herein), an intragastric balloon is provided, the intragastric balloon comprising: an intragastric balloon, the intragastric balloon comprising a uni-directional polymer film, the uni-directional polymer film comprising a plurality of polymer molecules oriented along a longitudinal axis.

In an embodiment of the second aspect, which is generally applicable (i.e., independently combinable with any of the aspects or embodiments identified herein), the uni-directional polymer film is embedded within a seam of the intragastric balloon.

In an embodiment of the second aspect, which is generally applicable (i.e., independently combinable with any of the aspects or embodiments identified herein), the intragastric balloon further comprises an erodible material in communication with the uni-directional polymer film, the erodible material configured to erode in the gastric environment over a period of time, wherein erosion of the erodible material is configured to form one or more holes in the uni-directional polymer film.

In an embodiment of the second aspect, which is generally applicable (i.e., independently combinable with any of the aspects or embodiments identified herein), the intragastric balloon further comprises an electronics package, the electronics package configured to initiate the formation of one or more holes in the uni-directional polymer film.

In an embodiment of the second aspect, which is generally applicable (i.e., independently combinable with any of the aspects or embodiments identified herein), the electronics package further comprises a timer, wherein the electronics package is configured to initiate the formation of one or more holes in the uni-directional polymer film at a predetermined time or after a predetermined amount of time.

In an embodiment of the second aspect, which is generally applicable (i.e., independently combinable with any of the aspects or embodiments identified herein), the electronics package further comprises a communications module, the communications module configured to receive data from an external device.

In an embodiment of the second aspect, which is generally applicable (i.e., independently combinable with any of the aspects or embodiments identified herein), the communications module is configured to receive an instruction to initiate the formation of one or more holes in the uni-directional film from the external device.

Any of the features of an embodiment of the first or second aspects, or any other feature herein disclosed, is applicable to all aspects and embodiments identified herein. Moreover, any of the features of an embodiment of the first or second aspects is independently combinable, partly or wholly with other embodiments described herein in any way, e.g., one, two, or three or more embodiments may be combinable in whole or in part. Further, any of the features of an embodiment of the first or second aspects may be made optional to other aspects or embodiments. Any aspect or embodiment of a method can be performed by a system or apparatus of another aspect or embodiment, and any aspect or embodiment of a system or apparatus can be configured to perform a method of another aspect or embodiment.

BRIEF DESCRIPTION OF THE DRAWINGS

FIG. 1 is a side view, showing several internal features in dotted lines, of an exemplary intragastric volume-occupying device equipped with a wire system for breaking one or more sections of the volume-occupying device, in accordance with a preferred embodiment.

FIG. 2 is a top view of a uni-directional polymer film, in accordance with a preferred embodiment.

FIG. 3 is an illustrative example of a tear forming in a uni-directional polymer film, in accordance with a preferred embodiment.

FIG. 4A is an illustrative example of a hole forming in a uni-directional polymer film, in accordance with a preferred embodiment FIG. 4B is an illustrative example of bi-directional spreading of the hole of FIG. 4A, in accordance with a preferred embodiment.

FIG. 5 is a perspective view, showing several internal features in dotted lines, of an exemplary intragastric volume-occupying device including a uni-directional polymer film, in accordance with a preferred embodiment.

FIG. 6A is an illustrative example of a hole forming in a uni-directional polymer film in an intragastric volume-occupying device, in accordance with a preferred embodiment.

FIG. 6B is an illustrative example of bi-directional spreading of the hole of FIG. 6A, in accordance with a preferred embodiment.

FIG. 7 is an illustrative example of a top half and a bottom half of an intragastric volume-occupying device including a uni-directional polymer film following separation of the unidirectional polymer film, in accordance with a preferred embodiment.

DETAILED DESCRIPTION OF THE PREFERRED EMBODIMENT

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

The term "degradable" as used herein is a broad term, and is to be given its ordinary and customary meaning to a person of ordinary skill in the art (and is not to be limited to a special or customized meaning), and refers without limitation to a process by which structural integrity of the balloon is compromised (e.g., by chemical, mechanical, or other means (e.g., light, radiation, heat, etc.) such that deflation occurs. The degradation process can include erosion, dissolution, separation, digestion, disintegration, delamination, comminution, and other such processes. Degradation after a predetermined time, or within a predetermined window of time, after ingestion is particularly preferred.

The term "CO2 barrier material" as used herein is a broad term, and is to be given its ordinary and customary meaning to a person of ordinary skill in the art (and is not to be limited to a special or customized meaning), and refers without limitation to a material having a permeability to $CO_2$ of 10 cc/m2/day or less under simulated in vivo conditions (100% humidity and body temperature of 37° C.). As used herein, the term "in vivo conditions" as used herein refers to both actual in vivo conditions, such as in vivo intragastric conditions, and simulated in vivo conditions. The permeability of a material to $CO_2$ may vary depending upon the conditions under which it is measured.

The term "swallowable" as used herein is a broad term, and is to be given its ordinary and customary meaning to a person of ordinary skill in the art (and is not to be limited to a special or customized meaning), and refers without limitation to ingestion of a balloon by a patient such that the outer capsule and its constituents are delivered to the stomach via normal peristalsis movement. While the systems of preferred embodiments are swallowable, they are also configured by ingestion by methods other than swallowing. The swallowability of the system is derived, at least in part, by the outer container size for the self-inflating system and the catheter and outer container size for the manual inflation system. For the self-inflating system, the outer capsule is sufficient to contain the inner container and its constituents, an amount of activation agent injected prior to administration, the balloon size, and the balloon material thickness. The system is preferably of a size less than the average normal esophagus diameter.

Described herein is a system for an orally ingestible device with one or more components configured to facilitate passage of the device through the digestive system. In preferred embodiments, the device is able to traverse the alimentary canal. The device may be useful, for example, as an intragastric volume-occupying device. The device overcomes one or more of the above-described problems and shortcomings found in current intragastric volume-occupying devices. While in certain embodiments specific devices are described, it is understood that the materials and methods can also be applied to other devices.

In order to more clearly describe the subject matter of the preferred embodiments, different embodiments of the same subcomponent will be described under a single relevantly-titled subheading. This organization is not intended to limit the manner in which embodiments of different subcomponents may be combined in accordance with the present invention. The various subcomponents used in the presently disclosed systems may be discussed under their respective subheaded sections or in any other section, including any section or sections discussing various tracking and visualization subcomponents.

Swallowable Intragastric Balloon System

A swallowable, self-inflating or inflatable intragastric balloon system according to selected preferred embodiments includes the following components: self-sealing valve system for addition of fluid to the lumen of the balloon or to the inner container ("valve system"), a balloon in a deflated and compacted state ("balloon") and an outer capsule, container, or coating ("outer container") that contains the balloon. For self-inflating balloons, an inner capsule or other container ("inner container") that contains one or more CO2 generating components is present inside the lumen of the balloon. The system may also include various components for facilitating delivery ("delivery components") of the balloon to the mouth and/or through the esophagus.

For inflatable balloons, an inflation fluid source, a catheter, and tubing ("inflation assembly") are provided for inflating the balloon after ingestion or placement in the stomach. In the self-inflating balloon configuration, the valve is preferably attached to the inner surface of the balloon by an adhesive or other means (e.g., welding), and provided with an inoculation spacer to prevent puncture of the wall of the balloon and inner container by a needle or other means for injecting an liquid activation agent into the lumen of the balloon via the self-sealing valve. A valve providing releasable attachment of the tubing to the balloon is provided in the inflatable balloon configuration. Preferably, the self-sealing valve system attached to the balloon (e.g., on its inside surface) in the inflatable configuration is "universal" or compatible with a swallowable catheter or a physician-assisted catheter. The valve system serves to allow for balloon inflation using a miniature catheter that includes a needle assembly and also provides a mechanism for detachment of the catheter after inflation has been completed.

The outer container preferably incorporates the balloon in a compacted state (e.g., folded and rolled), preferably with sufficient space to allow for activation liquid to be injected into the balloon in the self-inflating balloon configuration, wherein the liquid activation agent initiates separation, erosion, degradation, and/or dissolution of the inner container and generation of $CO_2$ upon contact with the inflation agent contained within the inner container, which subsequently causes outer container separation, erosion, degradation, and/or dissolution due to $CO_2$ gas pressure. In the inflatable balloon configuration, the outer container need only incorporate the balloon in a compacted state.

Selected components of a swallowable intragastric balloon system of a preferred embodiment can include a silicone head with radioopacity ring, trimmed 30 D silicone septum, Nylon 6 inoculation spacer, compacted balloon, inner container (if self-inflating), and outer container as constituents of the system in unassembled form. A fully assembled outer container can include a vent hole aligned with a septum for puncture to inject liquid activation agent (if self-inflating) or a port for connection of tubing (if inflatable). As discussed further below, the components of particularly preferred systems possess the attributes described herein; however, in certain embodiments systems can be employed which utilize components having other attributes and/or values.

Devices according to the preferred embodiments are intended for ingestion by a patient and deployment without the need to resort to invasive methods. It is therefore desirable that the device of the preferred embodiments be operable to conform to a compact delivery state which can be swallowed by a patient with minimal discomfort. Once in the stomach, it is desirable for the device to assume a substantially larger deployed state. In order to achieve the transition from a delivery state to a deployed state the device is subjected to inflation.

Inner Container

In order to initiate inflation in the self-inflating configuration, the inflation subcomponent may require outside inputs such as an activation agent. The activation agent is preferably injected using a syringe having a needle with a gauge diameter of from 25 to 32. The needle length is preferably from about 0.25 inches (0.6 cm) to 1 inches (2.54 cm) in length so as to create a flow rate that allows for delivery of the full volume of inflation agent within 30 seconds, but in a manner/stream/flow that does not physically damage the inner container, thereby causing premature $CO_2$ generation and inflation. The activation agent is preferably pure water, or a solution containing up to 50% concentration of anhydrous citric acid at 20° C., or the equivalent thereof at varying solution temperatures based on solubility of anhydrous citric acid. Preferably, the system is configured to have an occupyable void space in the central lumen of the balloon when in compacted form in the outer container of from about 0.3 ml to about 4.5 ml, such that a corresponding volume of activation agent can be injected into the void space.

In one embodiment, prior to folding, the free-floating inner container with inflation agent for $CO_2$ generation is preferably vertically aligned with the self-sealing valve system such that the septum/inoculation spacer is placed directly above the tip of the capsule. The balloon contains an inner container. A self-sealing valve system is adhesively adhered to the interior of the wall of the balloon, and the inverted configuration of the balloon is provided by inversion through a hole sealed with a patch. The top approximate ¼ of the balloon wall is folded over the inner capsule, and the pleats where the capsule is are creased similar to the pleats formed in the second step of making a paper airplane, then folded over to the left or to the right. The bottom approximate ¾ of the sphere is then accordioned using no more than 2 creases and folded over the capsule. The left half is then folded over the right half of the capsule or vice versa so that the wings touch. Then the material is rolled over until it creates a tight roll. The device is then placed inside the outer container.

In a self-inflating configuration, the balloon is folded so as to form a pocket around the inner capsule, to insure that the liquid injected through the self-sealing valve system is contained in an area less than 10% of the entire balloon surface area. It is not necessary to provide a pocket in the inflatable configuration, as no inner capsule is provided. The balloon is folded such that the number of total folds is minimized so as to minimize possible damage to the outer material or compromise of barrier properties. The number of total folds is preferably less than 10 folds. The balloon material is rolled when at all possible such that the number of creases required to fit the balloon in an outer container is minimized. This is done in effort to also to prevent lumen material damage. The self-sealing valve is also preferably constructed off-center of the balloon so as to minimize the number of folds that layer on top of each other.

In the self-inflating configuration, the material forming the wall of the balloon is processed and folded to maximize reaction efficiency by localizing the initiation agent injected into the balloon so that it is maintained proximal to the reactants within the inner container. The balloon is folded such that once the reaction initiates and the outer container separates, the balloon unfolds in a manner that creates the largest possible surface area, which prohibits the balloon from readily passing through the pyloric sphincter. The ratio of reactants in the inflation agent and activation agent are selected such that the pH of any remnant liquid inside the lumen of the balloon is acidic, with a pH of less than 6, such that any balloon leakage or breach that allows stomach acid to enter does not cause additional $CO_2$ generation and resulting unintentional re-inflation.

In a self-inflating configuration, an inflation agent is compressed, formed or otherwise held in a shape which provides good surface area availability for the reactants for $CO_2$ generation, while minimizing the space and/or volume sufficient to hold the inner container. Preferably, the inner container has a length (longest dimension) of from about 0.748 inches (1.9 cm) to 1.06 inches (2.7 cm) and a diameter or width of from about 0.239 inches (0.6 cm) to about 0.376 inches (1 cm). The volume of the inner container is preferably from about 0.41 ml to about 1.37 ml. The inner container is preferably in the form of a standard push-fit gelatin capsule but a gelatin tape may be used in lieu of a push-fit capsule. The container is preferably relied upon for containing the inflation agent; however, additional sealing or other encapsulation can be employed to control timing of inflation. Gelatin is particularly preferred for use as the inner container; however other materials can also be suitable for use, e.g., cellulose. In order to minimize the internal volume of the system, it is generally preferred to include only a single inner container; however, in certain embodiments two or more internal containers can advantageously be employed. Timing of self-inflation is selected based on a normal esophageal transit time and a normal time of gastric emptying of large food particles, such that the balloon does not inflate to a size that can block the esophageal passageway or prematurely pass through the pyloric sphincter. Timing is also controlled by compacting the balloon such that the activation agent is substantially localized in the balloon next to the inner capsule, creating an efficient $CO_2$ self-inflation method. Balloon inflation is initiated by the liquid activation agent causing degradation of the inner container, such that the inflation agent in the inner container contacts the liquid activation agent, thereby initiating the gas generation reaction.

Inflation Assembly

In certain preferred embodiments, the volume-occupying subcomponent is filled with a fluid using tubing which is subsequently detached and pulled away from the volume-occupying subcomponent. One end of the volume-occupying subcomponent has a port connected to tubing of sufficient length that when unwound can span the entire length of the esophagus, from mouth to stomach. This tubing is connected to the volume-occupying subcomponent with a self-sealable valve or septum that can tear away from the volume-occupying subcomponent and self-seal once the volume-occupying subcomponent is inflated. A physician or other health care professional secures one end of the tubing as the patient swallows the device. Once the device is residing within the stomach, the physician uses the tube to transmit a fluid, such as air, nitrogen, SF6, other gas(es), vapors, saline solution, pure water, a liquid or vapor under external ambient conditions (e.g., room temperature) that forms a vapor or gas, respectively, at in vivo temperatures (e.g., SF6), or the like, into the volume-occupying subcomponent and thereby inflate it. The fluid may be or include a variety of other fluid or non-fluid materials as well, including physiologically acceptable fluids, such as aqueous fluids, e.g., water, water with one or more additives (e.g., electrolytes, nutrients, flavorants, colorants, sodium chloride, glucose, etc.), saline solution, or the like. After the volume-occupying subcomponent is fully inflated, the tubing is released and can be pulled out from inside the patient.

The tube may be released in a number of manners. For example, the tubing may be detached by applying a gentle force, or tug, on the tubing. Alternatively, the tubing may be detached by actuating a remote release, such as a magnetic or electronic release. Additionally, the tubing may be released from the volume-occupying subcomponent by an automatic ejection mechanism. Such an ejection mechanism may be actuated by the internal pressure of the inflated volume-occupying subcomponent. For example, the ejection mechanism may be sensitive to a specific pressure beyond which it will open so as to release any excess pressure and simultaneously release the tube. This embodiment provides a desirable feature through combining release of the tubing with a safety valve that serves to avert accidental over inflation of the volume-occupying subcomponent in the patient's stomach.

This automatic release embodiment also provides the benefit that the device inflation step may be more closely monitored and controlled. Current technology allows for a self-inflating intragastric volume-occupying subcomponent which generally begins to inflate in a four minute timeframe after injection with an activation agent such as citric acid. In this approach, the volume-occupying subcomponent may, in some instances, begin to inflate prior to residing within the stomach (e.g., in the esophagus), or, in patients with gastric dumping syndrome or rapid gastric emptying, the volume-occupying subcomponent may end up in the small intestine prior to the time that inflation occurs. Accordingly, in certain embodiments it can be desirable to inflate the volume-occupying subcomponent on command, once it is ascertained that the volume-occupying subcomponent is residing in the correct location.

In certain embodiments, it may also be advantageous for the volume-occupying subcomponent to inflate gradually or in several steps over time, or for the volume-occupying subcomponent to maintain a volume and/or internal pressure within a preselected range. For example, if gas escapes the volume-occupying subcomponent prior to the desired deflation time, it can be beneficial for the device to re-inflate in order to preserve it in its expanded state.

Outer Container

The balloon is preferably provided in a deflated and folded state in a capsule or other retaining, containing or coating structure ("outer container"). The outer container is preferably in the form of a standard push-fit gelatin capsule, with the push-fit relied upon for containing the deflated/folded balloon; however, a gelatin wrap can advantageously be employed in certain embodiments. Gelatin is particularly preferred for use as the outer container; however other materials can also be suitable for use, e.g., cellulose, collagen, and the like. Preferably, the outer container has a length (longest dimension) of from about 0.95 inches (2.4 cm) to 2.5 inches (6.3 cm) and a diameter or width of from about 0.35 inches (0.9 cm) to about 0.9 inches (2.4 cm). The volume of the inner container is preferably from about 1.2 ml to about 8.25 ml. In the self-inflating configuration, the outer container is preferably configured with one or more holes, slits, passageways or other egresses, preferably on each end, which act as vents such that any gas created due to inflation agent exposure to condensation or other ambient moisture present during processing does not cause premature separation or degradation of the inner container prior to 30 seconds after inoculation of the liquid activation agent, which may have an undesirable effect on reaction efficiency. Such egresses can also expedite dissolution of the outer container to prepare the balloon for inflation in the inflatable configuration. The process of the outer capsule degrading (e.g., separates, dissolves, or otherwise opens) is expedited by pressure build up caused by inflation (self-inflation or inflation via catheter) of the balloon. The outer capsule can be dipped in water for a brief time to soften the materials but not release the balloon prior to swallowing to minimize the time lapse between swallowing and balloon inflation. In the inflatable configuration, the outer container is provided with a hole to house the inflation tube needle assembly, wherein the diameter of the catheter needle housing is mechanically compatible with the diameter of the outer container hole such that the needle can be inserted into the self-sealing valve while maintaining therein the housed balloon to facilitate pushing or swallowing of the balloon assembly. In a preferred embodiment, the outer container is a capsule. The distal half of the capsule may be flared to prevent abrasion of the balloon materials by the leading edge of the capsule as the compacted balloon is inserted into the capsule. The capsule can also comprise two parts held together with a gel band and encompassing the folded balloon that allows for quicker separation of the capsule so that inflation can take place more expeditiously. The outer capsule degrades (e.g., separates, dissolves, or otherwise opens) due to contact with ingested fluid ingestion (e.g., water intake) and preferably degrades within 5 minutes or less, more preferably within 2 minutes or less, so as not to cause discomfort to the patient while the balloon/catheter tube is in place.

In a preferred embodiment, the device is fitted into a standard sized gelatin capsule. The capsule may be formed of a material that has a known rate of degradation such that the device will not be released from the capsule or otherwise deployed prior to entry into the stomach. For example, the capsule materials may include one or more polysaccharide and/or one or more polyhydric alcohols.

Alternatively, the device, in its delivery state, may be coated in a substance that confines the device in its delivery state while also facilitating swallowing. The coating may be applied by a dipping, sputtering, vapor deposition, or spraying process which may be conducted at an ambient or positive pressure.

In certain preferred embodiments, the encapsulated or coated device is lubricated or otherwise treated so as to facilitate swallowing. For example, the encapsulated or coated device may be wetted, heated, or cooled, prior to swallowing by the patient. Alternatively, the encapsulated or coated device may be dipped in a viscous substance that will serve to lubricate the device's passage through the esophagus. Examples of possible coatings can be any substances with lubricious and/or hydrophilic properties and include glycerine, polyvinylpyrrolidone (PVP), petroleum jelly, aloe vera, silicon-based materials (e.g. Dow 360) and tetrafluoroethylene (TFE). The coating may also be applied by a sputtering, vapor deposition or spraying process.

In additional embodiments the coating or capsule is impregnated or treated with one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

In certain embodiments, the capsule may be weighted at a certain end in order for it to be oriented appropriately when it is administered, as it travels down the esophagus, and/or when it is in the stomach. The weighting components may include polymer materials or inflation reactants.

The swallowable, self-inflating intragastric balloon is provided with mechanisms to reliably control timing of self-inflation such that premature inflation while in the esophagus during swallowing is avoided and sufficient inflation once in the stomach so as to prevent passage through the pyloric sphincter is ensured. Normal esophageal transit time for large food particles has been documented as 4-8 seconds, and gastric emptying of large food particles through the pylorus does not occur for at least 15-20 minutes. The outer container is preferably configured to separate, dissolve, degrade, erode, and/or otherwise allow the deflated/folded balloon to begin unfolding not less than 60 seconds but not more than 15 minutes after inoculation with liquid activation agent. The inner container is preferably configured chemically, mechanically or a combination thereof to retard the initial $CO_2$ generating chemical reaction such that sufficient $CO_2$ to begin inflating the balloon is not available earlier than 30 seconds after inoculation with the liquid activation agent, but to permit generation of sufficient $CO_2$ such that at least 10% of the occupyable volume of the balloon is filled within 30 minutes, at least 60% of the occupyable volume of the balloon is filled within 12 hours, and at least 90% of the occupyable volume of the balloon is filled within 24 hours. This timing allows for injection of the activation agent into the outer container by the medical professional, passing the device to the patient, and swallowing by normal peristaltic means by the patient. This timing also prohibits potential passing of an uninflated balloon into the duodenum by the balloon being inflated to a sufficient size such that gastric emptying of the balloon cannot be easy, as objects more than 7 mm in diameter do not readily pass.

Delivery Components

It certain embodiments, it may advantageous for an administrator of the device to use a delivery tool for delivering the device to the mouth or facilitating its passage through the esophagus in the optimal orientation. A delivery tool may enable the device administrator to inject the device with one or more inflation agents or inflation gases as part of administering the device to the patient. In a preferred embodiment, such injection may be accomplished in the same mechanical action(s) of the administrator that are employed to release the device from the delivery tool into the mouth or esophagus. For example, the delivery tool may include a plunger, a reservoir containing a fluid, and an injection needle. The administrator pushes the plunger which, either in sequence or approximately simultaneously, forces the injection needle into the device and thereby injects the liquid contained in reservoir into the device. Subsequent application of force to the plunger pushes the device out of the delivery tool and into the desired location within the patient. Furthermore, the delivery tool may also include a subcomponent that administers an anesthetic or lubricant into the patient's mouth or esophagus to ease the swallowability of the device.

Balloon

The volume-occupying subcomponent ("balloon") of the preferred embodiments is generally formed of a flexible material forming a wall which defines an exterior surface and an interior cavity. Various of the above-described subcomponents may be either incorporated into the wall or interior cavity of the volume-occupying subcomponent. The, volume-occupying subcomponent can vary in size and shape according to the patient's internal dimensions and the desired outcome. The volume-occupying subcomponent may be engineered to be semi-compliant, allowing the volume-occupying subcomponent to stretch or expand with increases in pressure and/or temperature. For example, the volume-occupying subcomponent may be filled with a fluid that expands over time, such as $SF_6$, after the volume-occupying device is deployed into the patient's stomach and inflated with said fluid. Alternatively, in some embodiments, a compliant wall offering little resistance to increases in volume may be desirable. In some embodiments, the entirety of the volume-occupying subcomponent is expandable, meaning that the volume-occupying subcomponent can stretch in response to an increased volume of the fluid (liquid or gas) inside the volume-occupying subcomponent. In other embodiments, the volume-occupying subcomponent includes one or more expandable sections.

Spherical or elliptical volume-occupying subcomponents are preferred in certain embodiments. Alternatively, the volume-occupying subcomponent may be constructed to be donut-shaped, with a hole or through-channel in the middle of it, and may be weighted and shaped in such a way that it orients in the stomach to cover all or part of the pyloric sphincter, similar to a check valve. The hole in the middle of the volume-occupying subcomponent can then serve as the primary passage for the contents of the stomach to enter the small intestine, limiting the passage of food out of the stomach and inducing satiety by reducing gastric emptying. Volume-occupying subcomponent may be manufactured with different-sized donut-holes according to the degree that gastric emptying is desired to be reduced. Delivery, inflation and deflation of the volume-occupying subcomponent may be accomplished by any of the methods described above.

It is advantageous for the volume-occupying subcomponent wall to be both high in strength and thin, so as to minimize the compacted volume of the device as it travels the esophagus of the patient. In certain embodiments, the volume-occupying subcomponent wall materials are manufactured with a biaxial orientation that imparts a high modulus value to the volume-occupying subcomponent.

In one embodiment, the volume-occupying subcomponent is constructed of a polymeric substance such as polyurethane, polyethylene terephthalate, polyethylene naphthalate, polyvinyl chloride (PVC), Nylon 6, Nylon 12, or polyether block amide (PEBA). The volume-occupying subcomponent may be coated with one or more layers of substances that modify (increase, reduce, or change over time) gas-barrier characteristics, such as a thermoplastic substance.

Preferably, the gas-barrier materials have a low permeability to carbon dioxide or other fluids that may be used to inflate the volume-occupying subcomponent. The barrier layers should have good adherence to the base material. Preferred barrier coating materials include biocompatible poly(hydroxyamino ethers), polyethylene naphthalate, polyvinylidene chloride (PVDC), saran, ethylene vinyl alcohol copolymers, polyvinyl acetate, silicon oxide (SiOx), acrylonitrile copolymers or copolymers of terephthalic acid and isophthalic acid with ethylene glycol and at least one diol. Alternative gas-barrier materials may include polyamine-polyepoxides. These materials are commonly acquired as a solvent or aqueous based thermosetting composition and are generally spray-coated onto a preform and then heat-cured to form the finished barrier coating. Alternative gas-barrier materials which may be applied as coatings to the volume-occupying subcomponent include metals such as silver or aluminum. Other materials that may be used to improve the gas impermeability of the volume-occupying subcomponent include, but are not limited to, gold or any noble metal, PET coated with saran, conformal coatings and the like, as listed, for example, in Tables 1a-b.

In certain preferred embodiments, the volume-occupying subcomponent is injection, blow or rotational molded. Either immediately following such molding, or after a period of curing, the gas-barrier coating may be applied if not already applied within the composite wall.

In another embodiment, the intragastric volume-occupying subcomponent is formed using a Mylar polyester film coating silver, aluminum or kelvalite as a metalized surface, to improve the gas impermeability of the volume-occupying subcomponent.

In the event that the volume-occupying subcomponent's wall is composed of multiple layers of materials, it may be necessary to use certain substances or methods to connect, attach or hold together such multiple layers. Such substances can include a solvent or an ether-based adhesive. Such multiple layers may also be heat-bonded together. Once such layers are attached together to form (for example) a sheet of material to be made into a volume-occupying subcomponent, it may also be necessary to apply additional treatment steps to such material to allow it to seal together (for example, by application of a certain degree of heat and pressure) in order to be made into a volume-occupying subcomponent. Accordingly, it may be advantageous to include as an additional layer in the volume-occupying subcomponent certain materials that seal. For example, a volume-occupying subcomponent comprised of a combination of PET and SiOx layers, which impart favorable mechanical and gas impermeability characteristics to the volume-occupying subcomponent, may be sealed by including a layer of sealable polyethylene in such volume-occupying subcomponent.

According to another embodiment of the preferred embodiments, the functionality of the volume-occupying subcomponent and the deflation component is combined either in part or in whole. For example, the volume-occupying subcomponent may be formed of a substance that is degraded within the stomach over a desired period of time. Once the degradation process has formed a breach in the wall of the volume-occupying subcomponent, the volume-occupying subcomponent deflates, continues to degrade and passes through the remainder of the digestive tract.

Preferably, an automated process is employed that takes a fully constructed volume-occupying subcomponent, evacuates all of the air within the interior cavity and folds or compresses the volume-occupying subcomponent into the desired delivery state. For example, the evacuation of air from the volume-occupying subcomponent may be actuated by vacuum or mechanical pressure (e.g. rolling the volume-occupying subcomponent). In certain embodiments, it is desirable to minimize the number of creases produced in the volume-occupying subcomponent when in the delivery state.

Deflation and/or inflation of the volume-occupying subcomponent may be achieved through one or more injection sites within the wall of the volume-occupying subcomponent. For example, two self-sealing injection sites can be incorporated at opposite sides of the volume-occupying subcomponent. The volume-occupying subcomponent may be positioned within a fixture that employs two small-gauge needles to evacuate the air from the volume-occupying subcomponent.

In one embodiment, the self-sealing injection sites may further be used to insert chemical elements of the inflation subcomponent into the interior of the volume-occupying subcomponent. After injection of the chemical elements into the volume-occupying subcomponent, the same needles may be used to perform evacuation of the volume-occupying subcomponent.

It may be desirable that the volume-occupying subcomponent is packed into the delivery state under, for example, a negative vacuum pressure or under a positive external pressure.

The volume-occupying subcomponent wall materials may also be engineered to, once they are initially punctured or torn, tear relatively easily from the point of such puncture or tear. Such properties can, for example, be advantageous if deflation of the volume-occupying subcomponent were initiated by a tearing or puncturing of the volume-occupying subcomponent wall, since such initial tear or puncture may then increase in scope, hastening and/or maximizing the deflation process.

The volume-occupying subcomponent may also be coated by a lubricious substance that facilitates its passage out of the body following its deflation. Examples of possible coatings can be any substances with lubricious and/or hydrophilic properties and include glycerine, polyvinylpyrrolidone (PVP), petroleum jelly, aloe vera, silicon-based materials (e.g. Dow 360) and tetrafluoroethylene (TFE). The coating may be applied by a dipping, sputtering, vapor deposition or spraying process which may be conducted at an ambient or positive pressure.

The balloon composite wall materials can be of similar construction and composition as those described in U.S.

Patent Publication No. 2010-0100116-A1, the contents of which is hereby incorporated by reference in its entirety. The materials are able to contain a fluid, such as a liquid or a gas, preferably in compressed or non-compressed gas form, such as, e.g., N2, Ar, O2, CO2, SF6 or mixture(s) thereof, or atmospheric air (composed of a mixture of N2, O2, Ar, CO2, Ne, CH4, He, Kr, H2, and Xe) that simulate gastric space concentrations. In certain embodiments, the balloon is able to hold the fluid and maintain an acceptable volume for up to 6 months, preferably for at least 1 to 3 months after inflation. Particularly preferred fill gases include non-polar, large molecule gases that can be compressed for delivery.

Prior to placement in the outer container, the balloon is deflated and folded. In the inverted configuration in a deflated state, the balloon is flat, with the inverted seam extending around the perimeter of the balloon. The self-sealing valve system is affixed to the inner wall of the lumen close to the center of the deflated balloon, with the inner container positioned adjacent to the self-sealing valve system. The walls of the balloon are then folded. As part of the balloon design, the self-sealing valve system is manufactured in a manner such that it is placed "off center" to minimize the number of folds upon themselves (e.g., doubling or tripling up) required to fit the balloon in the outer container. For example, the self-sealing valve system can advantageously be placed ½ r±¼ r from the center of the balloon, wherein r is the radius of the balloon along a line extending from the center of the balloon through the septum.

Tracking and Visualization Subcomponent

It may also be beneficial to implement tracking and visualization functionality into devices according to the embodiments. Due to the non-invasive nature of the present device, physicians may desire to determine, or confirm, the location and orientation of the device prior to inflation or during the course of treatment.

Alternatively, the marker may be applied to the volume-occupying subcomponent when the volume-occupying subcomponent is in a creased or folded state such that when the volume-occupying subcomponent is in its deflated state the marker appears concentrated when viewed on visualization equipment, and when the volume-occupying subcomponent is inflated the marker appears less concentrated when viewed on visualization equipment. Alternatively, the marker may be applied or incorporated into the volume-occupying subcomponent so as to facilitate identification and location of the various subcomponents of the device, such as a valve, head, or weight. The marker may be printed or painted onto a surface of the volume-occupying subcomponent or between layers of the material forming the volume-occupying subcomponent. Alternatively, a metal coating as described below may be used as a marker to identify and/or locate the volume-occupying subcomponent. Metal coatings for visualizing the volume-occupying subcomponent may include silver, gold, tantalum or any noble metal. Alternatively, the marker may be applied to an elastomeric sleeve that covers all or part of the volume-occupying subcomponent.

In another embodiment, the volume-occupying subcomponent incorporates a subcomponent that changes mechanically upon inflation of the volume-occupying subcomponent, which mechanical change can be visualized using x-ray or other visualization equipment. For example, a mechanical portion of the volume-occupying subcomponent containing a visualization marker may elongate upon an increase in pressure in the volume-occupying subcomponent.

Alternatively, a marker may be formed using a metalized mesh located between layers of the material from which the volume-occupying subcomponent is constructed. The pattern or patterns formed by the imbedded marker will appear when the volume-occupying subcomponent is in an inflated, deployed state.

It is envisioned that marker materials may be incorporated into the volume-occupying subcomponent to facilitate various visualization techniques such as, for example, MRI, CT and ultrasound.

The volume-occupying subcomponent may also contain a dye or marker that is released upon deflation to indicate that the volume-occupying subcomponent cavity has been breached. Such dye or marker may, for example, be apparent in the patient's urine as an indication that the volume-occupying subcomponent has begun to deflate.

In yet further embodiments, microchips and other components employing electronic modalities may be used to locate and identify a device. Microchips analogous to those utilized for the identification of pets may be used to communicate device specific information and its approximate location. For example, a Wheatstone or other bridge circuit may be incorporated into the device and, together with RF "ping and listen" technology may be used as part of a system to determine the device's approximate location and measure and communicate device specific information. Such device specific information can include internal volume-occupying subcomponent pressure, which can indicate the degree of inflation of the volume-occupying subcomponent.

In yet further embodiments, mechanical, chemical, visual and other sensors may be included as part of the device to measure, record and/or transmit information relating to the device and/or the patient's internal environment. For example, the device may contain a camera or any of the other imaging and transmission components of a Pillcam device. As an additional example, the device may contain sensors that measure, record and/or transmit information relating to stomach pH, stomach pressure, hormone levels, organ health, and organ safety.

Valve System

In preferred embodiments, a self-sealing valve system which contains a self-sealing septum housed within a metallic concentric cylinder is provided. In the inflatable configuration, the self-sealing valve system is preferably adhered to the underside of the balloon material such that only a portion of the valve protrudes slightly outside of the balloon surface to ensure a smooth surface. The valve system for the inflatable configuration can utilize the same self-sealing septum designed for the self-inflating configuration. The septum preferably consists of a material possessing a durometer of 20 Shore A to 60 Shore D. The septum is inserted or otherwise fabricated into the smaller cylinder of the concentric metallic retaining structure that is preferably cylindrical in shape. The smaller cylinder within the larger cylinder controls alignment of the catheter needle sleeve/needle assembly with the septum, provides a hard barrier so that the catheter needle does not pierce the balloon material (needle stop mechanism), and provides compression such that the valve/septum re-seals after inflation and subsequent needle withdrawal.

The concentric valve system can also provide radio opacity during implantation and is preferably titanium, gold, stainless steel, MP35N (nonmagnetic, nickel-cobalt-chromium-molybdenum alloy) or the like. Non-metallic polymeric materials can also be used, e.g., an acrylic, epoxy, polycarbonate, nylon, polyethylene, PEEK, ABS, or PVC or any thermoplastic elastomer or thermoplastic polyurethane that is fabricated to be visible under x-ray (e.g., embedded with barium).

The septum is preferably cone shaped, so that the compressive forces are maximized for self-sealing after inflation. The self-sealing septum allows air to be evacuated from the balloon for processing/compacting and insertion into the outer container, and allows for piercing by an inflation agent syringe needle (self-inflating configuration) or inflation catheter needle (inflatable configuration), and then subsequent withdrawal of the inflation agent syringe needle or detachment of the inflation catheter and withdrawal of the catheter needle significantly limiting gas leakage outside of the balloon during the inflation process and needle withdrawal/catheter detachment. The septum is inserted into the valve using a mechanical fit mechanism to provide compression. An additional ring can be placed at the distal end of the inner cylinder to provide additional compression to ensure the septum material is dense enough to re-seal itself. The ring is preferably metallic in nature, but can also be a non-metallic polymeric material such as an acrylic, epoxy, or thermoplastic elastomer or thermoplastic polyurethane. The ring material is preferably the same material as the cylinder, titanium, but can also be gold, stainless steel, MP35N or the like.

In the inflatable configuration, a larger, outer cylinder of the concentric valve housing contains a slightly harder durometer material than the inner cylinder (50 Shore A or greater), but is also preferably silicone. The purpose of using a harder durometer material is to ensure sealing when connected to the needle sleeve for inflation. The silicone located in the outer ring of the concentric valve is adhered to the balloon from the inside surface. The entire outer cylinder is filled and a small circular lip of this same material is provided that is slightly larger than the diameter of the inner cylinder and extends to the outside surface of the balloon. The lip is compatible with the bell shaped needle sleeve and provides sealing to enhance connection of the valve to the catheter to withstand the inflation pressures applied and also increases the tensile force of the catheter. This silicone lip preferably does not protrude past the balloon surface more than 2 mm to ensure that the balloon surface remains relatively smooth and does not cause abrasion or ulcerations of the mucosa. It is designed to provide compressive forces against the needle sleeve of the catheter for inflation and detachment whereby when connected to the needle sleeve of the inflation catheters, the connection force during the inflation process can withstand up to 35 PSI. The seal is then broken during detachment using hydrostatic pressure that is more than 40 PSI less than 200 PSI to break the connection force. Two additional retaining rings, preferably made of the same material as concentric valve, are included in the valve system to further enhance the seal between the metal and the valve silicone and provide additional mechanical support to ensure proper mechanical fit and are intended to disrupt slippage of the silicone material from the hard (metallic) valve system (causing an increase in tensile force).

The valve structure for the inflatable configuration uses a mechanical fit mechanism to provide the functions of the self-sealable valve for inflation by the catheter and subsequent catheter detachment; however, primer and/or adhesive may be used to provide additional support in maintaining the assembly. The configuration can be modified by modifying the surfaces of the metal components, making them more sticky or slippery to provide the desired mechanical/interference fit. The interference fit between the valve and the catheter can be modified to change the pressure requirements for inflation and/or detachment. Additional assemblies can include overmolding the metallic portions or the concentric system in silicone such that additional support rings to ensure the mechanical fit and the tensile strength and forces required to sustain the assembly during catheter inflation and detachment can be omitted.

The total valve diameter in the inflatable configuration is designed to fit a miniature catheter system that does not exceed 8 French (2.7 mm, 0.105 inches) in diameter. The total diameter does not exceed 1 inch (2.54 cm) and is preferably less than 0.5 inches (1.27 cm), to facilitate swallowing. Additional valves can be added, if desired; however, it is generally preferred to employ a single valve so as to maintain the volume of the deflated/folded balloon (and thus the outer container dimensions) as small as possible. The valve system is preferably attached to the inner surface of the balloon such that a shear force greater than 9 lbs (40 N) is required to dislodge the valve system.

In a self-inflating configuration, the valve system can be attached to the balloon (e.g., on its inside surface) without the use of an opening, orifice, or other conduit in the wall of the balloon. The valve system can utilize a septum with a durometer of 20 Shore A to 60 Shore D. The valve can be inserted or otherwise fabricated into a retaining structure that has a higher durometer, e.g., 40 Shore D to 70 Shore D or more. The retaining structure can be fabricated from a silicone, rubber, soft plastic or any suitable non-metallic polymeric material such as an acrylic, an epoxy, a thermoplastic elastomer, or thermoplastic polyurethane. Preferably, a structure, such as a ring, that can be metallic or non-metallic but radioopaque (e.g., barium) and visible under X-ray, or magnetic or magnetizable and detectable by sensing of a magnetic field, can be embedded in the retaining structure. Using a mechanical fit mechanism of two structures of different durometers, one softer (septum) with a large diameter, can be inserted into a snug, more rigid durometer structure creates compressive forces in the once open orifice to enable CO2 retention and reduce susceptibility for CO2 gas leaks. The metallic ring for radio-opacity also helps to create compressive forces on the septum. The self-sealing septum allows air to be evacuated from the balloon for processing/compacting and inserting in the outer container, and also allows for the inflation agent to be injected into the outer container for inflation initiation. Additional septums can be provided, if desired; however, it is generally preferred to employ a single septum so as to maintain the volume of the deflated/folded balloon (and thus the outer capsule) as small as possible. The valve system is preferably attached to the inner surface of the balloon such that a shear force greater than 9 lbs (40 N) is required to dislodge the valve system. A silicone head and opacity ring of a self-sealing valve system can be employed, as can a wedge-shaped septum.

In the self-inflating configuration, an inoculation spacer is preferably incorporated to guide a needle into the self-sealing valve for injection of liquid activation agent into the lumen of the balloon and to prevent the needle from penetrating the wall of the deflated/folded balloon elsewhere such that pressure within the lumen of the balloon cannot be maintained. The inoculation spacer also facilitates preventing liquid activation agent from penetrating the inner container or the folded balloon material, thereby focusing the activation agent in an appropriate manner to properly mix the reactants for CO2 generation according to the criteria described above. The inoculation spacer is generally in the form of a tube or cylinder. The inoculation spacer is preferably attached to the inner container and/or the self-sealing valve system with an adhesive or other fixing means; however, in certain embodiments the inoculation spacer can be "free-floating" and maintained in position by the folding or rolling of the walls of the balloon. The inoculation spacer can comprise any suitable material that can be passed after separation, erosion, degradation, digestion, and/or dissolution of the outer container; however, preferable materials include non-metallic materials with a minimum Shore D durometer of 40 or more, any metallic material, or a combination thereof. A cupped needle stop (inoculation spacer) can be employed in preferred embodiments.

Balloon

In a preferred embodiment, a self-inflating balloon is fully sealed 360 degrees around. In the self-inflating configuration, with injection of an inflation agent by needle syringe, there are preferably no external openings or orifices to the central lumen. In the inflatable configuration, a valve structure (either protruding, recessed, or flush with the surface of the balloon) is provided for providing an inflation fluid to the central lumen. The balloon can have a "noninverted," "inverted," or "overlapped" configuration. In a "noninverted" configuration, the seams or welds and seam allowance, if any, are on the outside of the inflated balloon. In an "overlapped" configuration, layers are overlapped, optionally with one or more folds, and secured to each other via welds, a seam, adhesive, or the like, resulting in a smooth external surface. In an "inverted" configuration, the balloon has a smooth external surface with seams, welds, adhesive bead, or the like inside the inflated balloon. In order to create a balloon with an inverted configuration, e.g., a balloon with no external seam allowance (no wall material between the edge of the balloon and the weld, seam, or other feature joining the sides together), two balloon halves are joined together in some fashion (e.g., adhered using adhesive or heat or the like based on the balloon material used). One of the balloon halves encompasses an opening to allow for the balloon to be pulled through itself after adherence of the two halves and to have the seams of the balloon on the inside. The opening created is preferably circular but can be any similar shape, and the diameter of the opening preferably does not exceed 3.8 cm; however, in certain embodiments a larger diameter may be acceptable. A patch of material is adhered (adhesively, heat welded, or the like, based on the material used) to cover the original balloon-half opening. The inversion hole thus created that is subsequently patched is small enough that the forces exerted during inflation do not compromise the material used to maintain fluid in the balloon. The preferred shape for the inflated balloon in final assembly is ellipsoid, preferably spheroid or oblate spheroid, with nominal radii of from 1 inch (2.5 cm) to 3 inches (7.6 cm), a nominal height of from 0.25 inches (0.6 cm) to 3 inches (7.6 cm), a volume of from 90 cm3 to 350 cm3 (at 37° C. and at internal nominal pressure and/or full inflation), an internal nominal pressure (at 37° C.) of 0 psi (0 Pa) to 15 psi (103421 Pa), and a weight of less than 15 g. The self-inflating balloon is configured for self-inflation with CO2 and is configured to retain more than 75% of the original nominal volume for at least 25 days, preferably for at least 90 days when residing in the stomach. The inflatable balloon is configured for inflation with an appropriate mixture of gases so as to deliver a preselected volume profile over a preselected time period (including one or more of volume increase periods, volume decrease periods, or steady state volume periods).

In certain embodiments wherein a stable volume over the useful life of the device is preferred, the balloon is configured to maintain a volume of at least 90% to 110% of its original nominal volume. In other embodiments, it can be desirable for the balloon to increase and/or decrease in volume over its useful life (e.g., in a linear fashion, in a stepwise fashion, or in another non-linear fashion). In other embodiments, the balloon maintains a volume of 75% to 125% of its original nominal volume, or 75% to 150%. The intragastric device can be a single free-floating or tethered device. In some embodiments, it can be desirable to provide multiple devices (2, 3, 4, 5, 6, or more), either free-floating or tethered to each other, e.g., in a similar configuration to a cluster of grapes. The individual devices can be simultaneously inflated with one inflation system connected to all of the devices, or each device can be provided with a separate inflation system.

Inner Container

The inner container for the self-inflating balloon is contained within the lumen of the balloon and contains the CO2 generator for balloon self-inflation. The CO2 generator comprises an inflation agent mixture housed within the container. Preferably, from about 10% to about 80% of the total inflation agent used comprises powdered citric acid, with the remainder comprising powdered sodium bicarbonate. Sufficient inflation agent is provided such that upon completion of the CO2 generating reaction, the balloon achieves inflation at the nominal inflation pressure described above. Preferably, a total of from about 0.28 to 4 grams inflation agent mixture is employed, depending upon the balloon size to be inflated; preferably up to 1.15 grams of sodium bicarbonate is used with the remainder being powdered citric acid to generate 300 cm3 of CO2 at nominal pressure.

Inflation Assembly

An intragastric balloon system that is manually inflated by a miniature catheter can be employed in certain embodiments. The system preferably remains "swallowable." The balloon for delivery is in a compacted state and is attached to a flexible, miniature catheter, preferably no larger than 4 French (1.35 mm) in diameter. The catheter is designed such that a portion of the catheter can be bundled or wrapped upon itself for delivery with the encapsulated balloon, allowing the patient to swallow both catheter and balloon for delivery to the stomach. The balloon can contain a self-sealable valve system for attachment of the catheter and inflation of the balloon once it reaches the stomach cavity. The proximal end of the catheter can be left just outside of the patient's mouth, permitting connection to an inflation fluid container that can house the preferred inflation fluid (gas or liquid). After inflation the catheter can be detached from the balloon valve and pulled back through the mouth. This method allows for the intragastric balloon to maintain its swallowability but allow for inflation by a fluid source or a mixture of fluid sources via the catheter. Alternatively, a more rigid, pushable system can be employed wherein the balloon valve is compatible with either the swallowable, flexible catheter or the pushable, rigid catheter assembly.

The inflation catheters (swallowable or administrator-assisted pushable) described herein are configured to deliver the balloon device orally and without any additional tools. The administration procedure does not require conscious sedation or other similar sedation procedures or require endoscopy tools for delivery. However, other versions of the device can be used in conjunction with endoscopy tools for visualization or can be adapted such that the balloon device can be delivered nasogastrically as well.

In operation, the proximal end of the inflation catheter is connected to a valve or connector that allows for connection to the inflation source or the disconnect source, this is preferably a Y-arm connector or inflation valve. The connector materials may consist of polycarbonate or the like and can connect to a single or multi-lumen catheter tube. The distal end of the inflation catheter is connected to the universal balloon valve of the balloon that has been compacted and housed within a gelatin capsule or compacted using gelatin bands. The catheter tube is preferably from 1 French (0.33 mm) to 6 French (2 mm) in diameter. The catheter is preferably long enough to extend out past the mouth (connected to the inflation connector or valve) and transverse the esophagus down to at least the middle of the stomach—approximately 50-60 cm. Measurement ticks can be added to the tubing or catheter to aid in identifying where the end of the tube is located. Timing for inflation can be initiated by having the tube contain a pH sensor that determines a location difference between the esophagus (pH 5-7) and the stomach (pH 1-4) based on the different pH between the two anatomical sources, or can be derived or verified from the expected pressure in a contained (i.e., esophagus) versus a less-constrained space (i.e., stomach). The tube can also contain nitinol that has a tunable transmission to the body temperature, taking into account the timing for swallowing. The tube can also be connected to a series of encapsulated or compacted balloons on a single catheter. Each can be inflated and released separately. The number of balloons released can be tune-able to the patient's needs and desired weight loss. In certain embodiments, the intragastric balloon or catheter is located or tracked in the body by sensing a magnetic field of a magnetizable component of both or either devices, as discussed in detail below.

In certain embodiments, a catheter with the balloon at the distal end (inflated with air) is employed to temporarily and firmly hold the balloon in place. A small deflated balloon catheter can be positioned through the head of the gastric balloon (e.g., a "balloon within the balloon"), and then inflated with air during delivery to firmly hold the capsule and balloon in place and prevent spontaneous detachment of balloon from the catheter. This balloon catheter can incorporate a dual channel that can also allow the bigger gastric balloon to be inflated (by gas or liquid). Once the gastric balloon has been satisfactorily inflated, the small air balloon catheter can be deflated and pulled out of the valve (allowing the valve to self seal), and out of the body, leaving the inflated gastric balloon in the stomach.

In other embodiments, the catheter may be coated to enhance swallowability or is impregnated or treated with one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

Dual Lumen Catheter

In a preferred embodiment, a swallowable dual lumen catheter is provided. The dual lumen catheter has two lumens with a diameter of the complete assembly no larger than 5 French (1.67 mm), preferably no larger than 4 French (1.35 mm). The inner lumen preferably does not exceed 3 French (1 mm) and functions as the inflation tube, and the outer lumen preferably does not exceed 5 French (1.67 mm) and functions as the disconnection tube; the inner and outer lumen do not exceed 2 French (0.66 mm) and 4 French (1.35 mm), in diameter, respectively. The catheter assembly is connected to a needle assembly, described in more detail below, at the distal end and to a dual port inflation connector at the proximal end. The tubing that the catheter assembly employs is flexible for swallowability, is kink resistant, can withstand body temperature, is resistant to acid, and is biocompatible as the tube transverses the alimentary canal into the stomach cavity. The tube materials are preferably soft and flexible and have moderate tensile strength and a significant amount of hoop strength to handle applied pressures. The lumens are preferably round and co-axial and free-floating so as to provide flexibility. The dual lumen assembly also preferably requires no adhesive or glue. Alternative lumen configurations can include two D-lumens or a combination of a D-lumen and round lumen, and can be used in stiffer configurations of the final catheter assembly. Preferred materials for the tubing include a thermo-resistant polyethylene tubing such as PEBAX® or a thermo-resistant polyurethane tubing such as PELLETHANE™, PEEK or Nylon. The tubing can also be manufactured out of bioresorbable materials such as polylactic acid (PLA), poly-L-aspartic acid (PLAA), polylactic/glycolic acid (PLG), poly-caprolactone (PCL), DL-lactide-co-ε-caprolactone (DL-PLCL) or the like, wherein the tube can be released after inflation and detachment and swallowed as normal.

At the distal end of the catheter assembly, the inner lumen or inflation tube is attached to the needle assembly that is used to puncture the balloon's self-sealing valve, preferably located at one of the apexes of the balloon housed inside of a gelatin capsule as outer container. The outer lumen is connected to the needle sleeve and provides connection force between the catheter assembly and balloon providing the tensile strength to withstand balloon inflation pressures, e.g., pressures of up to 10 psi or higher, while maintaining the assembly together. The needle sleeve is configured to mechanically couple with the balloon valve assembly. The needle is preferably made of metal, preferably stainless steel or the like, with a maximum size of 25 gauge (0.455 mm), preferably no smaller than 30 gauge (0.255 mm) for inflation timing purposes. The needle sleeve is preferably a soft material such as nylon or the like, or can also be polycarbonate, polyethylene, PEEK, ABS or PVC. The needle sleeve covers the length of the needle in its entirety, such that the body is protected from the needle and the needle can only pierce the balloon septum. Preferably the needle sleeve is flush or extends out slightly more than the needle length. The needle is inserted into the balloon septum prior to swallowing and maintains a retention force of approximately 0.33 lb (0.15 kg) when coupled to the silicone area of the balloon valve. The needle sleeve is preferably slightly bell shaped or contains a circular relief or lip so that when inserted into the silicone area of the valve a lock and key mechanism is created to increase the tensile strength of the assembly and enhance the sealing for inflation.

At the proximal end, the catheter assembly is connected to a Y-adapter assembly preferably made of polycarbonate. The y-adapter is "keyed" so that the inflation gas and connection fluid are connected to the catheter assembly appropriately and travel down the correct lumen.

Prior to inflation, priming of the disconnection lumen may be employed using a liquid. For example, the outer lumen is first flushed with 2 cc of water, saline, DI water or the like prior to balloon inflation. Thereafter, the inflation source container is attached to the connector leading to the inner lumen. The inflation source container works on the premise of the ideal gas law and a pressure decay model. For a given compressed gas formulation, the device is designed to equalize such that a higher starting pressure is used to inflate the balloon than is the resulting end pressure of the balloon. The starting pressure and volume are dependent upon the gas formulation selected, as well as the length of the catheter and the starting temperature (typically ambient temperature) and ending temperature (typically body temperature).

After inflation, the balloon is detached from the catheter assembly using hydraulic pressure. A syringe filled with water, DI water, or preferably saline is attached to the female end of the Y-assembly. The syringe contains 2 cc of liquid and when the syringe plunger is pushed in, enough hydraulic pressure is exerted such that the needle is ejected from the balloon valve.

Single Lumen Catheter

To further reduce the diameter of the inflation catheter, thereby increasing swallowability comfort, a single lumen catheter can be employed that does not exceed 2 French (0.66 mm) in diameter.

The needle/needle sleeve assembly is similar in design to that of the dual lumen catheter described herein. However, with the single lumen system, the distal end of the catheter lumen connects to the needle sleeve only and there is no second catheter inside. Instead, a single thread attached to a needle hub runs co-axially the length of the catheter to aid in tensile strength for detachment and overall flexibility.

The needle sleeve is slightly bell shaped or contains a circular relief or lip so that when inserted into the silicone area of the valve a lock and key mechanism is created to increase the tensile strength of the assembly, enhance the sealing for inflation, and since this is a single lumen assembly, the lip increases the force required to remove the needle from the valve so this does not occur haphazardly during the inflation process.

The proximal end of the catheter is connected to a 3-way valve and uses a method of exclusion for inflation and detachment of the balloon. The distal end of the catheter contains the needle sleeve, which is made of nylon or other similar source. The needle is metallic and preferably stainless steel.

The tubing that the catheter assembly employs is flexible for swallowability, is kink resistant, can withstand body temperature, is resistant to acid, and is biocompatible as the tube transverses the alimentary canal into the stomach cavity. The tube materials are preferably soft and flexible, preferably co-axial, and resistant to necking or buckling or kinking. For a single lumen system, the catheter tubing is preferably made of PEBAX®, but can also comprise bioresorbable materials such as PLA, PLAA, PLG, PCL, DL-PLCL or the like, wherein the tube can be released after inflation and detachment and swallowed as normal. The wire inside the catheter tubing attached to the needle is preferably a nylon monofilament, but Kevlar or nitinol wire or other suitable materials can also be used.

To inflate the balloon, the distal end of the catheter is attached to the balloon capsule where the needle protrudes through the self-sealable valve. The container is swallowed and a portion of the inflation catheter remains outside of the mouth. The inflation source container is connected to the proximal 3-way valve, where the port for inflation gas is chosen by excluding the other ports. The inflation fluid (preferably compressed nitrogen gas or a mixture of gases) travels down the single catheter lumen, whereby the inflation gas selects the path of least resistance, or more specifically through the needle cavity and into the balloon. The balloon is preferably inflated in less than 3 minutes.

To detach and withdraw the needle from the balloon valve, 2 cc or other suitable volume of water or other liquid is injected into the catheter at a high pressure. Since water has a high surface tension and viscosity, it occludes the needle pathway and the pressure is transferred to the outside needle sleeve, thereby breaking the fit between the needle sleeve and the balloon valve.

If it is desired to place a substance inside the balloon, such as water or acid or any alternative liquid, it can be done by using a lower pressure to inject the liquid.

Miniature Stiff-Bodied Inflation Catheter

In certain embodiments, a stiff-bodied inflation catheter can be employed, which can be placed orally or transnasally. This system can be from 1 French (0.33 mm) to 10 French (3.3 mm), preferably 8 French (2.7 mm) in diameter. A larger diameter is typically preferred to enhance pushability, with wall thickness also contributing to pushability and kink resistance. The length of the tube can be approximately 50-60 cm. As discussed above, measurement ticks can be added to the tubing to identify where the end of the tube is located, or a pH or pressure sensor on the catheter can be employed to detect location of the balloon.

This system for inflation/detachment is similar to the dual lumen system described above, but with a larger needle sleeve to accommodate the larger diameter tube. Materials that can be used in the lumen include, e.g., expanded polytetrafluoroethylene (EPTFE) for the outer lumen and polyetheretherketone (PEEK) for the inner lumen. To also enhance pushability, a strain relief device can be added to the distal and proximal ends. It is particularly preferred to have strain relief at the distal end, e.g., 1 to 8 inches, preferably 6 inches, to ensure the catheter bypasses the larynx and follows into the esophagus. The proximal end can have strain relief as well, e.g., to ensure fit of the Y-arm. The preferred material for the strain relief is a polyolefin. The method for inflation/detachment is the same method as for the dual lumen configuration where the outer lumen connects to the needle sleeve and the inner lumen connects to the needle. As part of the procedure, the patient can swallow water or other suitable liquid so as to distend esophageal tissue for smooth passage down of the device. Patients can also be administered an anesthetic at the back of the throat to numb the area and lessen the gag reflex.

The tube can also be connected to a series of encapsulated or compacted balloons on a single catheter such that a total volume of up to 1000 cc or more can be administered, as necessary. Each can be inflated and released separately. The number of balloons released can be tunable to the patient's needs and desired weight loss.

In addition, a catheter can be used for administering a gastric balloon that is similar to balloon catheters used in angioplasty termed "over-the-wire" or rapid exchange catheters. In this case where the patients attempts to swallow the catheter but fails so the stiff catheter—or physician assisted catheter can slide over the flexible catheter and the balloon can be pushed down in the same manner as the physician-assisted catheter. Different materials can be used to provide the varying degrees of flexibility or one material that is fabricated with different diameters across the length to vary the degree of stiffness can be used.

The swallowable self-inflating balloon construction method and the swallowable inflation tube construction method both remove the requirement for endoscopy to place the balloon and make the balloon administration process less invasive. This also allows for the total volume to be placed in a patient to be "titratable," or adjustable. When a balloon is placed for 30 days, a patient may report that over time they lose their feeling of fullness without eating. To compensate, another balloon can be placed easily without sedation and endoscopy. When a non-deflatable balloon is to be removed endoscopically, it is desirable to color-code the balloon composite walls with different colors so that the physician has a visual marker for removing the balloon at the end of its useful life while keeping the balloon that has remaining useful life in the patient's stomach.

In addition, the balloon wall can be marked approximately 180° from the self-sealing valve such that when the balloon is punctured endoscopically it folds more efficiently on itself so as to facilitate removal of the thin-walled structure without causing esophageal perforations and/or other damage by the balloon due to its shape, stiffness, and/or thickness of the wall material.

Inflation Fluid Container

The inflation fluid container is employed to control the amount or volume of fluid placed inside of the balloon. This can be in the form of a canister of, e.g., PVC, stainless steel, or other suitable material. The container can also be in syringe form. The materials employed are able contain a fluid, preferably in gas form, e.g., compressed or non-compressed $N_2$, Ar, $O_2$, $CO_2$, or mixture(s) thereof, or compressed or non-compressed atmospheric air (a mixture of $N_2$, $O_2$, Ar, $CO_2$, Ne, $CH_4$, He, Kr, $H_2$, and Xe). The balloon composite wall materials and respective diffusion gradients and gas permeability characteristics are used to select a fluid for inflation of the intragastric balloon, so as to provide a desired volume profile over time for the inflated balloon. The inflation fluid container materials are selected to ensure no or minimal diffusion or leakage of the fluid before it is connected to the y-arm connector or valve of the inflation catheter. The inflation fluid container preferably incorporates a pressure gauge and a connector. It can also contain a smart chip that notifies the healthcare professional of whether inflation is successful or if the balloon should be detached due to an error in the system.

To maintain "swallowability" of the balloon and to ensure comfort of the patient during the procedure, it is preferred to minimize the amount of time the catheter is placed in the mouth/esophagus. Timing of inflation is can be selected so as to minimize time in place. The outer container-catheter assembly, once swallowed, takes approximately 4-8 seconds to reach the stomach. Once in the stomach, the Inflation source container can be attached to the valve or port of catheter system. Inflation timing can be controlled by selecting the length of catheter, diameter of the catheter tube, the starting temperature, and the starting pressure. Using the Ideal Gas Law for nitrogen and Boyle's Law ($P_1V_1=P_2V_2$) the amount of starting volume/pressure can be derived, where temperature is controlled inside the inflation source container to match that of the body. It is desired to have an inflation time after swallow of less than 5 minutes, and preferably 2-3 minutes, before balloon detachment and catheter withdrawal. The inputs use to derive inflation of the balloon (preferably in less than 3 minutes) include inflation container volume, type of inflation fluid (preferably a compressed gas or compressed gas mixture), starting pressure, catheter length and diameter, and desired end volume and pressure of the balloon. Thus, due to differences in diameter, a 2 French catheter system requires a higher starting pressure to achieve the same target balloon volume and pressure in the same time frame, assuming use of the same compressed gas formulation. In general, it is understood that starting with a higher pressure with the same flow rate/volume can decrease the inflation time.

The inflation source container provides feedback to the end user based on a pressure decay system. Where there is an expected starting pressure and expected ending pressure to indicate whether the balloon is inflated properly, there is no need for endoscopic visualization. Each scenario of expected pressure outputs can have its own tolerances around it to reduce possibilities of false positives, and the inflation fluid container can provide feedback based on these tolerances as to the status of balloon inflation and detachment. This is derived based on the Ideal Gas Law, where there is an expected end pressure based on the fixed volume of the balloon. If the pressure remains high and doesn't decay as expected, this can indicate a failure in the system (e.g., the balloon container did not dissolve, the balloon is expanding in the esophagus because there is, e.g., a kink in the tube or other failure in the catheter system). For example, for a successful decay using nitrogen only as the inflation fluid, the starting pressure is 22 PSI to inflate a balloon to 250 cc and 1.7 psi (0.120 kg/cm$^2$) for a nylon-based material. To indicate successful balloon inflation, a math chip can be added to the inflation source container that provides at least one of a visual, audible, or tactile notification, or otherwise transmits a notification to a healthcare professional or administrator of whether inflation is successful or if there is an error in the system based on the pressure curve and a set of predetermined pressure tolerances and expected timing of inflation.

Another method for detection of any degree of constraint that the balloon may be experiencing (e.g., capsule dissolved but balloon is in the esophagus or duodenum, or balloon is in the stomach and the capsule has not dissolved by reading the gauge output is to employ an inflation canister that has at least two reservoirs (one large and one small) and at least two gauges, with one or more valves that allow for selection of gas release into the second reservoir or into the balloon itself. With two reservoirs, the larger reservoir can contain the total amount of fluid required to fill the balloon. A small amount of fluid can be released from the larger reservoir into the smaller reservoir first to determine the location of the balloon and its readiness for full inflation. If the small amount of fluid in the smaller reservoir is released into the balloon catheter and the feedback on the gauge of the smaller reservoir indicates that the pressure is high, this indicates that the balloon is still contained in the capsule and it is not ready to be inflated. When the gauge reads back a medium pressure level (e.g., 1-4 psi), this indicates that the balloon is in a constrained space, such as the esophagus or duodenum, and should not be inflated. When the balloon catheter's feedback as read on the gauge is approximately 1 psi, this indicates that the balloon is in the stomach and ready to be inflated. If the feedback is at 0 psi, this indicates is a leak in the balloon valve catheter system and that the device should be retrieved. Once the balloon is detected in the stomach space, then the larger reservoir is opened and the balloon is inflated to its desired pressure.

Alternatively, the balloon can be filled based on a starting pressure by using a spring mechanism, a balloon-within-balloon mechanism, or other pressure source. These mechanisms can potentially result in more predictable/consistent pressure decay curves, and again can have accompanying, predetermined tolerances for feedback back to the end user.

Composite Wall

The materials selected for the composite wall of the balloon may be optimized to maintain the original inflation gas without significant diffusion, or may also allow for diffusion of the gases located in the gastric environment, e.g., CO2, O2, argon, or N2 to diffuse through the wall of the balloon to inflate, partially or wholly, once the balloon is placed in the stomach. A fluid (a liquid or gas) can also be added inside of the balloon using the inflation catheter(s) described herein to change diffusion direction of the balloon composite wall and when it reaches stasis based on the internal and external environment.

A gastric balloon inflated by nitrogen, CO2 gas, SF6, a single fluid (liquid or gas) or a mixture of fluids employs a composite wall that provides barrier properties (fluid retention), properties imparting resistance to pH and moisture conditions in the gastric environment or the environment within the central lumen of the balloon, and structural properties to resist gastric motility forces, abrasion of the balloon wall in vivo, and damage during manufacturing and folding of the balloon. Certain materials employed in the balloon materials are able to withstand a hostile gastric environment designed to break down foreign objects (e.g., food particles). Some of the variables that the gastric environment encompasses are as follows: gastric liquid pH of from 1.5-5; temperature of approx. 37° C.; a relative humidity of 90-100%; ingress of gastric space gas content; and constant gastric motility external pressures of from 0-4 psi at variable frequencies and cycle times based on the fed state of the stomach. The external pressure imparted by gastric motility can also cause abrasions on the surface of the balloon. The inside of the balloon lumen may contain moisture from a solution injected in the balloon for timing of auto-deflation or any moisture that has transferred across the membrane due to the external humid environment. In addition to these environmental stresses the wall materials meet biocompatibility requirements and are constructed such that the total thickness of the wall (barrier material) is thin enough to be compacted and placed inside of a swallowable-sized container ("outer container") without significant damage or lodging. The outer container is small enough to transcend the esophagus (which has a diameter of approximately 2.5 cm). The wall or barrier material is also heat formable and sealable for balloon construct and maintains a bond strength that can contain internal gas pressures of up to 10 psi generated by the initial inflation pressure as well as pressure due to the ingress of gas molecules from the stomach cavity until the system's gas environment reaches stasis. The film properties that are evaluated to determine suitability for use in the composite wall of the balloon include pH resistance, water vapor transmission rate, gas barrier properties, mechanical strength/abrasion properties, temperature resistance, formability, flex-crack (Gelbo) resistance, surface energy (wettability) compliance, and heat bond potential.

The various layers in the composite wall can impart one or more desirable properties to the balloon (e.g., CO2 retention, resistance to moisture, resistance to acidic environment, wettability for processing, and structural strength). A list of polymer resins and coatings that can be combined into a multi-layer preformed system ("composite wall") is provided in Tables 1a-b. These films can be adhesively bonded together, co-extruded, or adhered via tie layers or a combination thereof to obtain the desired combination of properties for the composite wall, as discussed below. The materials identified as film coatings in Tables 1a-b are provided as coatings applied to a base polymer film, e.g., PET, Nylon, or other structural layer.

TABLE 1a

Film Resins

| | Characteristics | | |
|---|---|---|---|
| | Good Structural/ Behavior/ Mechanical Strength/ Compliance | Good Fluid Retention Barrier Properties | Good Manufacturability/ Surface Energy Properties |
| FILM RESINS | | | |
| Polyethylene Terephthalate (PET) | X | X | |
| Polytrimethylene Terephthalate (PTT) | | | |
| Liquid Crystal Polymer (LCP) | X | X | |
| Polytrimethylene naphthalate (PTN) | X | X | |
| Polyethylene naphthalate (PEN) | X | X | |
| Polyimide (PI) | X | X | |
| Linear Low Density Polyethylene (LLDPE) | | | X |
| Ethylene Vinyl Alcohol (EVOH) | | X | |
| Polyamide: Nylon (PA) and Nylon-6 (PAG)/Nylon 12 | | X | X |
| High Density Polyethylene (HDPE) | | | X |
| Polypropylene (PP) | | | X |
| Polyurethane | | | X |
| PVDC (Saran) | | X | X |
| Polyether Block Amide (Pebax) | | | X |
| Polyvinyl Alcohol (PVOH) | | X | |
| Silicone | X | | X |

TABLE 1b

Film Coatings

| | Characteristics | | |
|---|---|---|---|
| | Good Structural/ Behavior/ Mechanical Strength/ Compliance | Good Fluid Retention Barrier Properties | Good Manufacturability/ Surface Energy Properties |
| FILM COATINGS | | | |
| Silicon Dioxide (SiO2) | | X | |
| Aluminum Oxide (Al$_2$O$_3$) | | X | |
| Nanopolymers (Nano/Clay) | | X | |
| External Organic Coatings (e.g., epoxy amine) | | X | |
| Inorganic Coatings (e.g., Amorphous Carbon) | | X | |
| Oxygen Scavengers | | X | |
| Parylene C | | X | |

Fluid Retention Layers

In preferred embodiments, a blended polymer resin using multiple layers is employed to maintain the inflated balloon's shape and volume by retaining the inflation fluid for the duration of the intended use. Certain barrier films, widely used in the food packaging and plastic bottling industries, can advantageously be employed for this purpose in the composite wall of the balloon. Preferably, the barrier materials have a low permeability to carbon dioxide (or other gases, liquids, or fluids that are alternatively or additionally used to inflate the volume-occupying subcomponent). These barrier layers preferably have good adherence to the base material. Preferred barrier coating materials and films include polyethylene terephthalate (PET), linear low density polyethylene (LLDPE), ethylene vinyl alcohol (EVOH), polyamides such as Nylon (PA) and Nylon-6 (PA-6), polyimide (PI), liquid crystal polymer (LCP), high density polyethylene (HDPE), polypropylene (PP), biocompatible poly(hydroxyamino ethers), polyethylene naphthalate, polyvinylidene chloride (PVDC), saran, ethylene vinyl alcohol copolymers, polyvinyl acetate, silicon oxide (SiOx), silicon dioxide (SiO2), aluminum oxide (Al2O3), polyvinyl alcohol (PVOH), nanopolymers (e.g., nanoclay), polyimide thermoset film, EVALCA EVAL EF-XL, Hostaphan GN, Hostaphan RHBY, RHB MI, Techbarrier HX (SiOx-coated PET), Triad Silver (silver metalized PET), Oxyshield 2454, Bicor 84 AOH, acrylonitrile copolymers, and copolymers of terephthalic acid and isophthalic acid with ethylene glycol and at least one diol. Alternative gas-barrier materials include polyamine-polyepoxides. These materials are typically provided as a solvent-based or aqueous-based thermosetting composition and are typically spray-coated onto a preform and then heat-cured to form the finished barrier coating. Alternative gas barrier materials that can be applied as coatings to the volume-occupying subcomponent include metals such as silver or aluminum. Other materials that may be used to improve the gas impermeability of the volume occupying subcomponent include, but are not limited to, gold or any noble metal, PET coated with saran, and conformal coatings.

One method that is used in the packaging industry to delay diffusion of the inflation fluid is to thicken the material. Thickening the material is generally not preferred, as the total composite wall thickness preferably does not exceed 0.004 inches (0.010 cm) in order for the balloon to be foldable into the desired delivery container size for swallowing by a patient.

A multilayer polymer film that is able to withstand the gastric environment over the course of the usable life of the balloon includes linear low density polyethylene (LLDPE) adhesively bonded to a Nylon 12 film. Alternatively, an additional film layer with barrier properties, such as PVDC can be added to the composite wall.

The layers providing gas barrier properties are preferably situated as inner layers in the composite wall as they are less mechanically robust than resins that are considered "structural" such as Nylon and the like.

Structural Layers

Layers such as polyurethane, Nylon, or polyethylene terephthalate (PET) can be added to the composite wall for structural purposes, and are preferably placed as outermost (proximal to the gastric environment or proximal to the central lumen of the balloon) layers, provided that the pH resistance of such layers can withstand the acidic environment of the stomach or the central lumen of the balloon. Other layers may in addition or alternatively be included.

Fabrication of the Composite Wall

The various layers of the composite wall, including the gas barrier layers, need not be situated in any particular order, but those of superior resistance to acidity, tempera- ture, mechanical abrasion, and superior biocompatibility profile are preferably employed as layers contacting the gastric environment. Those with superior resistance to, e.g., acidity and temperature, are preferably employed as layers contacting the central lumen of the balloon.

The various layers of the wall can include a single layer or up to 10 or more different monolayers; however, a film thickness of from 0.001 inches (0.0254 cm) to 0.004 inches (0.010 cm) thick is desirable such that the resulting balloon compacted to fit into a swallowable capsule. The resulting composite wall preferably has good performance specifications with respect to each category listed in Tables 1a-b.

Films that are co-extruded are advantageously employed, as some adhesives may contain leachables that are undesirable from a biocompatibility perspective. In addition, coextrusion allows for better blending such that the materials maintain their original properties when combined in this fashion and are less likely to be subject to delamination when exposed to gastric motility forces.

Combining films with similar properties, e.g., two film layers with excellent gas barrier properties, in a composite wall is advantageous for use in a gastric balloon containing nitrogen, oxygen, CO2 or a mixture thereof as the inflation gas or where the external environment the product is to be placed in, contains a mixture of gases including CO2, e.g., the stomach. A primary advantage of such composite films is that restrictions on film thickness can be observed without sacrifice of gas barrier properties. Such a configuration also contributes to reducing the effects of processing damage (e.g., manufacturing and compacting) and damage due to exposure to in vivo conditions (e.g., gastric motility forces).

In a particularly preferred embodiment, the composite wall includes a plurality of layers. The first layer is an outer protective layer that is configured for exposure to the gastric environment. This layer is resistant to mechanical forces, exposure to water (vapor), abrasion, and high acidity levels. Nylon or more specifically, Nylon 12 is particularly preferred for the layer exposed to the gastric environment, and is especially resistant to mechanical forces.

In an alternative embodiment, polyurethane is RF welded to saran to yield a 6-7 mil thick composite wall. In another embodiment, a five layer system is provided comprising a layer of saran sandwiched between two polyurethane layers. Between the saran layer and each of the polyurethane layers is a tie layer. The layers can be welded together, co-extruded or adhered using an adhesive. This tri-layer is then co-extruded to Nylon on each side, and then a final sealing layer (polyethylene or the like) is added to one of the nylon layers for the total composite wall. A representative example of material combinations that are commercially available or manufacturable is provided in Table 2. The orientation of the layers (innermost—in contact with the central balloon lumen, or outermost—in contact with the gastric environment) is also indicated if more than two layers are described to support a suggested composite wall.

Most of the film resins listed in Table 2 provide some degree of gas barrier properties. Therefore, many can be used solely to form the balloon wall as a monolayer film; however they can also be used in conjunction with other film resins to meet the desired gas retention and mechanical specifications for the useful life of the balloon based on the inflation gas and external environment the balloon is to be placed in. These film resins can also be coated with gas barrier coatings listed in Tables 1a-b. Additional film layers can be added to form the total composite wall. While such additional layers may not impart substantial barrier properties, they can provide structural and/or mechanical properties, protection for the other layers of the composite wall that are susceptible to water vapor, humidity, pH, or the like, or other desirable properties. The film layers can be assembled using various adhesives, via co-extrusion, via lamination, and/or using tie layers and such to create a composite wall that meets the requirements of an intragastric balloon suitable for use for at least 25 days, or up to 90 days or more, with the specified gas retention properties. Table 2 provides a list of layers and layer combinations suitable for use in composite walls for an intragastric balloon. The composite description, resin abbreviation, configuration (single layer, bilayer, trilayer, or the like) and trade name of commercially available combinations are listed. The number of layers indicated does not include any adhesive layers or tie layers used to fabricate the composite wall, such that a 6-layer composite wall may, for example, have two or three adhesive layers and/or tie layers that make up the total composite wall, and therefore the total number of layers can be eight or nine in final form. The term "layer" as used herein is a broad term, and is to be given its ordinary and customary meaning to a person of ordinary skill in the art (and is not to be limited to a special or customized meaning), and refers without limitation to a single thickness of a homogenous substance (e.g., a coating such as SiOx, or a layer such as PET, or a uniform polymeric blend), as well as to a supporting layer having a coating thereon (wherein a "coating" is, e.g., a material typically employed in conjunction with substrate that provides structural support to the coating layer). For example, a PET-SiOx "layer" is referred to herein, wherein a layer of SiOx is provided on a supporting PET layer. In the following table, as well as other tables referring to composite walls, a forward slash ("/") is used to indicate a boundary between layers of the specified chemistries. The boundary can be a discontinuity, or can be a tie layer, adhesive layer, or other layer separating the layers of recited chemistry.

TABLE 2

| Example Film Composite Walls* | Abbreviation | Trade name |
|---|---|---|
| polyethylene terephthalate | PET | Mylar |
| metalized oriented polyethylene terephthalate | metalized OPET | Custom |
| polyvinyl alcohol coated oriented polypropylene | PVOH coated OPP | Bicor |
| metalized biaxially oriented nylon 6 | metalized OPA6 | Custom |
| Biaxially oriented Nylon/ethylene vinyl alcohol/biaxially oriented Nylon | OPA/EVOH/OPA | Honeywell Oxyshield Plus |
| Nylon/ethylene vinyl alcohol/Low Density Polyethylene | Nylon/EVOH/LDPE | Custom |
| polyvinylidene chloride coated oriented polyethylene terephthalate | PVDC/OPET | Mylar |
| polyvinylidene chloride coated oriented polypropylene | PVCD/OPP | Custom |
| polyvinylidene chloride coated biaxially oriented Nylon 6 | PVCD/OPA6 | Honeywell Oxyshield |
| high density polyethylene/ethylene vinyl alcohol | HDPE/EVOH | Custom |
| polypropylene/ethylene vinyl alcohol laminate | PP/EVOH | Custom |
| polyethylene terephthalate/ethylene vinyl alcohol | PET/EVOH | Custom |
| metalized oriented polypropylene | metalized OPP | Custom |
| sealable PVDC coated oriented polypropylene | PVDC coated PP | Custom |
| polyvinylidene fluoride | PVDF | Custom |
| Polyvinyl chloride | PVC | Custom |
| polyvinyl fluoride | PVF | Tedlar |
| polychlorofluoroethylene | PCTFE | ACLAR UltRx, SupRx, Rx |
| amine-based epoxy coated Nylon | epoxy coated PA6 | Bairocade |
| polyvinyl chloride-polyvinylidene chloride copolymer | PVC-PVDC | Custom |
| medium density polyethylene | MDPE | Custom |
| Nylon/Polypropylene | Nylon/PP laminate | Custom |
| Nylon-High Density Polyethylene | Nylon-HDPE laminate | Custom |
| Nylon 12/Ethyl Methyl Acrylate/Polyvinylidene Chloride/Ethyl Methyl Acrylate/Nylon 12/Linear Low Density Polyethylene + Low Density Polyethylene | Co-extruded Nylon 12-encapsulated PVDC-Nylon 12-LLDPE + LDPE | Custom Co-extruded blend |
| Multi-layer Nylon 12/Linear Low Density Polyethylene + Low Density Polyethylene | Co-extruded multi-layer Nylon 12-LLDPE + LDPE | Custom Co-Extruded Blend |
| acetylene plasma coating on polyester | PET/A | Custom |
| difluoroethylene coating on polyethylene terephthalate | PET/DA | Custom |
| oriented polypropylene | OPP | Custom |
| cast propylene | CPP | Custom |
| high density polyethylene | HDPE | Custom |

TABLE 2-continued

| Example Film Composite Walls* | Abbreviation | Trade name |
|---|---|---|
| cyclic olefin copolymer | COC | Custom |
| oriented polystyrene | OPS | Custom |
| Fluorinated Ethylene Propylene | FEP | Custom |
| difluoroethylene coating on low density polyethylene | LDPE/D | Custom |
| difluoroethylene coating on polypropylene | PP/D | Custom |
| acetylene plasma coating on polypropylene | PP/A | Custom |
| acetylene plasma coating on low density polyethylene | LDPE/A | Custom |
| polybutylene terephthalate polyether glycol copolymer | TPC-ET | Hytrel |
| polyether block amide TPE | PEBA | Pebax |
| oxide coated biaxially oriented Nylon | oxide coated PA | Honeywell Oxyshield Ultra |
| Nanoclay/nylon | MXD6/Nanoclay | Imperm/Aegis OXCE |
| Polyethylene Terephthalate/Silicone Dioxide | PET/SiOx | BestPET/ TechBarrier |
| Polyethylene Terephthalate/Oxygen scavengers | PET + 02 Scavengers | MonoxBar |
| Modified Polyethylene Terephthalate | Modified PET | DiamondClear |
| Polyethylene Terephthalate/Nylon 6 | PET/MXD6 | HP867 |
| Amorphous polyvinyl alcohol | Amorphous PVOH | Nichigo G-Polymer |
| Nylon 6/Ethyl vinyl alcohol/Linear Low Density Polyethylene | Nylon 6/EVOH/LLDPE | Custom |
| Ethyl vinyl alcohol/Poly-Propylene/Ethyl vinyl alcohol | EVOH/PP/EVOH | Custom |
| Ethyl vinyl alcohol/Nylon | EVOH/Nylon | Custom |
| Polyethylene/Ethyl vinyl alcohol/Polyethylene | PE/EVOH/PE | Custom |
| Polyethylene/Ethyl vinyl alcohol/Polyethylene Terephthalate | PE/EVOH/PET | Custom |
| Silicon dioxide-coated Polyethylene Terephthalate/Linear Low Density Polyethylene/Ethyl vinyl alcohol/Linear Low Density Polyethylene | PET-SiOx/LLDPE/EVOH/LLDPE | Custom |
| Aluminum Oxide-coated Polyethylene Terephthalate/Polyethylene | PET-Al$_2$O$_3$/LLDPE | Custom |
| Polyethylene/Ethyl vinyl alcohol/Linear Low Density Polyethylene | PE/EVOH/LLDPE | Custom |
| Polyethylene Terephthalate/ Polyethylene/Polyethylene/Bi-axially oriented Ethyl vinyl alcohol | PET/PE/OEVOH/PE | Custom |
| Polyethylene Terephthalate/ Polyethylene/Ethyl vinyl alcohol/ Ethyl vinyl alcohol/Ethyl vinyl alcohol/Polyethylene | PET/PE/EVOH/EVOH/EVOH/PE | Custom |
| Polyethylene Terephthalate/ Polyethylene/Nylon 6/Ethyl vinyl alcohol/Nylon 6/Polyethylene | PET/PE/Nylon 6/EVOH/Nylon 6/PE | Custom |
| Silicone dioxide-coated Polyethylene Terephthalate/ Polyethylene/Ethyl vinyl alcohol/ Polyethylene | PET-SiOx/PE/EVOH/PE | Custom |
| Polyethylene/Ethyl vinyl alcohol/polyvinylchloride | PE/EVOH/PVDC | Custom |
| Polyethylene Terephthalate/ Linear Low Density Polyethylene/Ethyl vinyl alcohol/ Linear Low Density Polyethylene | PET/LLDPE/EVOH/LLDPE | Custom |
| Kurrarister C-coated Polyethylene Terephthalate/Polyethylene/Ethyl vinyl alcohol/Polyethylene | PET-Kurrarister-C/PE/EVOH/PE | Custom |
| Polyethylene Terephthalate/ Polyethylene/Nylon 6/Ethyl vinyl alcohol/Nylon 6/Polyethylene | PET/PE/Nylon 6/EVOH/Nylon 6/PE | Custom |
| Nylon 6/Ethyl vinyl alcohol/ Polyvinylchloride/Low Density Polyethylene | Nylon 6/EVOH/PVDC/Nylon 6/LDPE | Custom |

TABLE 2-continued

| Example Film Composite Walls* | Abbreviation | Trade name |
|---|---|---|
| Polyimide | PI | Custom |
| Polyimide/Linear Low Density Polyethylene | PI/LLDPE | Custom |
| Polyimide/Polyvinylchloride | PI/PVdC | Custom |
| Polyimide/Polyvinylchloride/ Linear Low Density Polyethylene | PI/PVdC/LLDPE | Custom |

In particularly preferred embodiments, the composite wall has a thickness of 0.005 inches or less (5.0 mil or less); however, in certain embodiments a thicker composite wall may be acceptable. Generally it is preferred that the composite wall have a thickness of no more than 0.004 inches (4.0 mil).

Fabrication of the Balloon

To ensure good mechanical strength of the balloon, the balloon is preferably thermoformed and sealed such that the edges of the pieces used to form the balloon are overlapping. This can be accomplished by any suitable method. For example, two flat sheets of material can be placed in a frame with magnetized edges to hold the two sheets in place. Slack can be added to the piece of film to orient the material such that it maintains its properties after the thermoforming process. The frame can be placed over a mold that represents a hemisphere the balloon. A heater (e.g., a 4520 watt infrared heater) can be used to form the material, and a vacuum can be pulled. The material, with slack put in it prior to vacuum being applied, re-orients the material such that it is more evenly distributed around the hemisphere shape. The material is preferably thickest in the middle and is made thinner on the sides where it will be welded to a second piece to create a sphere or ellipsoid having a substantially uniform wall thickness. For example, starting with a 0.0295" film, the middle of the film or subsequent apex has an ending film thickness of 0.0045" and the edges have an ending thickness of 0.0265" for subsequent overlapping during the welding process.

The valve can be adhered to the (e.g., polyethylene, PE) side of one of the hemispheres and protrude out of the opposite (e.g., nylon) side. One hemisphere typically consists of Nylon as the outermost layer and the second hemisphere typically has polyethylene (sealing web) as the outermost layer. The edges of the two hemispheres are preferably aligned such that they overlap by at least 1 mm and no more than 5 mm. Alignment and overlay of the two hemispheres is done to compensate for the thinning at the edges during the thermoforming process, which in turn inhibits seam bursts in vivo. Each half of the spheroid is placed on a fixture and the excess from the thermoforming process is trimmed. On a multi-layer film, the sealing layer, a PE or similar layer is bonded to the sealing layer of the second film half. To do this the film of the hemisphere that has the nylon exposed to the external environment is folded up along the edges of the sphere on one half such that it can be bonded to the hemisphere with the polyethylene on the outermost layer.

The two film pieces are then sealed using a roller bonder or a band heater. In the roller bonder, the air provides the compression, the heater provides the sealing heat, and a motor that moves the bonder around the area controls the time that is required to ensure proper sealing. In the band heater, there is a heating element, an expandable plug that provides the compression, and a timer. The band is a metal, preferably copper and a spool-like fixture provides the compression needed. Using film layers of different melt temperatures helps ensure integrity of the barrier layers of the final balloon configuration. If two similar materials are welded, then an insulator can be employed. In a preferred embodiment, one sphere is provided with the Nylon layer facing out and the second sphere has a PE layer facing out.

Balloons with Resistance to Spontaneous Deflation

The largest percentage of intragastric balloon malfunctions is due to spontaneous deflations. Spontaneous deflations can occur due to (1) external puncture of the intragastric balloon due to gastric motility forces, (2) over inflation of the balloon due to increased internal pressure of the balloon from uptake of the gastric environment of the gasses and water vapor and (3) under inflation of the balloon that leads to fatiguing of the excess material and subsequent puncture of the balloon. By managing these two variables and tuning these variables to withstand the dynamic gastric environment, the balloon system can be tailored to ensure it remains inflated throughout its useful life. Instances of spontaneous deflation in this intragastric balloon can be minimized by selection of the starting inflation gas in conjunction with selection of the composite wall materials and construction. Selection of the permeability characteristics with respect to water vapor transmission and gas permeability of the composite wall so as to take advantage of the properties of the gastric space contents can enable the rate of diffusion of gases into and out of the balloon to be controlled. This method allows for a tunable method for prevention of under inflation and over inflation.

Another phenomenon seen with gastric balloons and obesity in general is stomach accommodation. In the process of stomach accommodation, the stomach grows to accommodate the space occupying device or excess food that is ingested. In the process of stomach accommodation, the volume of a stomach containing an intragastric balloon grows over time, such that the patient becomes hungrier. However, by controlling gas diffusion and water vapor transmission across the balloon wall over time, the balloon size can also be increased over time by selecting the starting inflation gas(es) and water and other in vivo gas permeability characteristics of the film so as to maintain weight loss. In addition to spontaneous deflations, selecting the permeability characteristics of the composite wall in conjunction with the starting gases and utilizing the transfer of gases and water inside of the balloon from the gastric environment, the balloon can be designed to grow over its useful life in response to stomach accommodation.

Experiments were performed wherein various starting inflation gases were selected in conjunction with varying external gas environments that mimic the stomach gas and water environment in vivo. The stomach environment consists of water, acid (hydrochloric acid), a mixture of gases, and chyme (the semifluid mass of partly digested food expelled by the stomach into the duodenum). Stomach gas usually arises from swallowing air during eating. The composition of air is nitrogen ($N_2$) 78.084%; oxygen ($O_2$)

20.9476%; argon (Ar) 0.934%; carbon dioxide (CO2) 0.0314%; neon (Ne) 0.001818%; methane (CH4) 0.0002%; helium (He) 0.000524%; krypton (Kr) 0.000114%; hydrogen (H2) 0.00005%; and xenon (Xe) 0.0000087%.

Five gases constitute greater than 99% of the gases in gastrointestinal system: N2, O2, CO2, H2 and methane, with nitrogen predominating. Gastric pCO2 closely parallels local (splanchnic) arterial and draining venous blood pCO2 values. Neutralization of stomach acid can also generate gas. For example, when the stomach acid reacts with bicarbonates (e.g., as are present in certain antacids) in the digestive juices, the chemical process creates CO2, which is normally absorbed into the blood stream. Digestion of food in the intestines, mainly through fermentation by colonic bacteria, generates CO2, H2, and methane. Microbes appear to be the sole source of all of the hydrogen and methane produced in the intestine. These arise from fermentation and digestion of nutrients (polysaccharides from fruits and vegetables are not digested in the small intestines). Small quantities of a few other gases, including hydrogen sulfide, indoles, and ammonia can also be generated.

In certain embodiments, it is preferred that the composition of the initial fill gas is substantially characteristic of the composition of the mixture of gases in the in vivo gastric environment. Such an initial fill gas can include only N2 and CO2, or can include only N2, CO2, and O2, or can include N2 and CO2 as well as one or more other gases present in the in vivo environment (e.g., water vapor, H2, CH4, Ar, H2S, or NH3). Argon or another inert gas (or inert gases) can be substituted in part or in whole for N2, which is considered an inert gas in the context of the preferred embodiments. In those embodiments wherein the fill gas includes only N2 or CO2, it is preferred that the initial fill gas comprises from about 75% v/v to about 96% v/v N2, from about 5% v/v to about 15% (vol.) O2, and from about 1% v/v to about 10% v/v CO2, more preferably from about 80% (vol.) to about 85% (vol.) N2, from about 5% (vol.) to about 13% (vol.) O2, and from about 4% (vol.) to about 8% (vol.) CO2. In those embodiments wherein the fill gas includes only N2 or CO2, it is preferred that the initial fill gas comprises from about 4% (vol.) to about 8% (vol.) CO2, with the remainder N2 or another inert gas. In embodiments wherein the initial fill gas comprises other gases in addition to CO2 and the inert gas(es), it is preferred that the initial fill gas comprises from about 4% (vol.) to about 8% (vol.) CO2.

Controlled self-inflation of the intragastric balloon in the in vivo environment can be achieved by using a semipermeable or permeable composite wall in the balloon and initially filling the balloon with a preselected single gas, such as N2 or O2. The balloon utilizes differences in concentrations of gases and water concentration differences between the internal balloon environment and the external environment in vivo (GI/stomach) to increase and/or decrease the volume and/or pressure over time. To achieve a controlled decrease in volume and/or pressure, a wall can be employed that has a relatively higher permeability to the single gas used to inflate the balloon than to other gases present in the in vivo gastrointestinal environment. For example, if nitrogen gas is employed as the inflation gas, over time in the in vivo environment, the volume and/or pressure in the balloon will decrease as nitrogen diffuses out into the in vivo environment through the oxygen permeable wall. Similarly, if oxygen gas is employed as the inflation gas, over time in the in vivo environment, the volume and/or pressure in the balloon will decrease as oxygen diffuses out into the in vivo environment through the oxygen permeable wall. The differential in partial pressure of the single gas in the balloon (higher) versus the in vivo environment (lower) will drive the process until equilibrium or homeostasis is reached. To achieve a controlled increase in volume and/or pressure, a wall can be employed that has a relatively lower permeability to the single gas used to inflate the balloon than to other gases present in the in vivo gastrointestinal environment. For example, if nitrogen gas is employed as the inflation gas, over time in the in vivo environment, the volume and/or pressure in the balloon will increase as CO2, and all of the other gases present in the gastric environment, diffuse into the balloon through the CO2 permeable wall. The differential in partial pressure of the permeable gas in the balloon (lower) versus the in vivo environment (higher) will drive the process until equilibrium is reached.

In addition, maintaining and/or controlling inflation of the balloon can also be done using the differences in concentrations between the internal balloon environment and external gastric environment in which the balloon volume/pressure can be increased or decreased as needed to extend the useful life of the product. One reason to decrease the pressure can be to first inflate the balloon with a large, but highly diffusible/soluble gas molecule such as CO2 in addition to a more inert gas like nitrogen to pre-stretch the balloon, with the soluble gas diffusing out of the balloon and other gases not originally present in the balloon migrating in to fill the balloon.

Inflation gases can be selected to start with the majority of the gas in the balloon comprising a large, inert gas or a gas that has low diffusivity through the selected composite wall. Examples of inert gases include but are not limited to nitrogen, as well as SF6, C2F6, C3F8, C4F10, C4F8, C4F8, C3F6, CF4, and CCl F2-CF3. An inert gas in conjunction with a less inert gas(es) that are more soluble in the gastric environment, can be combined to comprise the starting balloon inflation gas composition where the inert gas would be in excess to the more soluble/diffusible gas. Patient diet and medications can also affect/control balloon inflation status—primarily by CO2 concentration effects produced in the gastric environment. In addition, gastric pH also affects CO2 concentration. This particular method can also allow for a greater degree of tuning of the device's useful life based on the composite wall material, e.g., barrier/non-barrier and whether the gas that diffuses in is maintained longer in the balloon if it has a barrier wall versus a non-barrier wall. This particular form of self-inflation can be employed using a self-inflating gastric balloon (e.g., initially inflated by a gas generating reaction in the balloon initiated after swallowing), or an inflatable gastric balloon (e.g., inflated using a catheter, with or without endoscopic assistance, delivered nasogastrically or any other delivery method). The method can be used with any gastric balloon, including swallowable balloons and balloons placed in the stomach by, e.g., endoscopic methods. The method is particularly preferred for use in connection with intragastric devices; however, it can also be applied to use in, e.g., pulmonary wedge catheters and urinary incontinence balloon devices. The advantages to this technology include the ability to compensate for stomach accommodation, allowing the balloon to adapt to a stomach that may increase in volume over time, thereby maintaining patient satiety. It also permits starting with a smaller amount of inflation gas constituents for a self-inflating balloon. It can prevent spontaneous deflations by utilizing diffusion gradients between gastric balloon systems and the in vivo gastric environment.

In some embodiments, one or more liquids are used as an inflation agent. Liquids suitable for use as an inflation agent include, but are not limited to pure water, saline solution, and liquid forms of the previously described inflation gases such as SF6, C2F6, C3F8, C4F10, C4F8, C4F8, C3F6, CF4, CCl F2-CF3, and combinations thereof. In some embodiments, the inflation agent can include a mixture of one or more inflation liquids and one or more inflation gases. The inflation agent can include between less than 10% and greater than 90% liquid. In some embodiments, the inflation agent can include between 10% and 30%, between 30% and 60%, or between 60% and 90% liquid. In some embodiments, the inflation agent can include 10%, 20%, 30%, 40%, 50%, 60%, 70%, 80%, and 90% liquid. In certain embodiments, it is preferred that the composition of the inflation agents is substantially characteristic of the composition of the mixture of gases in the in vivo gastric environment.

The volume-occupying subcomponent can be constructed of a polymeric substance such as polyurethane, polyethylene terephthalate, polyethylene naphthalate, polyvinyl chloride (PVC), Nylon 6, Nylon 12, or polyether block amide (PEBA). In some preferred embodiments used in connection with inflation agents including an inflation liquid, the volume-occupying subcomponent consists entirely or primarily of silicone. However, any suitable biocompatible material capable of withstanding the gastric environment and strong enough to hold the inflation agent may be used. Examples of such materials are listed in Tables 1a-b and 2. In some embodiments, the volume-occupying subcomponent includes materials that are expandable. In a particularly preferred embodiment having an expandable volume-occupying subcomponent SF6 is used as the inflation agent. SF6 expands at a defined rate, allowing for control over the rate of balloon expansion, the final expanded balloon size, and the length of time it takes to achieve the desired final size.

In a particularly preferred embodiment, used in connection with N2 (with or without CO2) as the inflation agent, a multi-layer co-extruded blend for the wall layers is employed. A particularly preferred configuration is Nylon 12/Ethyl Methyl Acrylate/Polyvinylidene Chloride/Ethyl Methyl Acrylate/Nylon 12/Linear Low Density Polyethylene+Low Density Polyethylene (also referred to as co-extruded Nylon 12-encapsulated PVDC-Nylon 12-LLDPE+ LDPE multilayer). Another particularly preferred configuration is a co-extruded multi-layer Nylon 12/Linear Low Density Polyethylene+Low Density Polyethylene. Selection of the resins for the composite wall construction (as well as selection of using a coextrusion method or adhesives) can be varied to control compliance (stretchiness), puncture resistance, thickness, adhesion, sealing bond strength, orientation, acid resistance, and permeability characteristics to gasses and water vapor to achieve a particular effect.

Deflation of Intragastric Balloon Systems

The self-inflating or inflatable intragastric balloon may deflate or deteriorate, due to failure of the balloon or as an intended mechanism to facilitate passage of the balloon through the digestive system at the end of its predetermined useful life. If an intragastric balloon is insufficiently deflated, the intragastric balloon may block the pylorus or may enter the patient's intestine and cause an intestinal blockage. Intestinal blockage can occur if the intragastric balloon device deflates too slowly and passes through the pylorus while not fully deflated. In some instances, a quantity of liquid can become trapped in a deflating or deflated intragastric volume-occupying device, causing the intragastric balloon to block the pylorus or may enter the patient's intestine and cause an intestinal blockage. This can occur, for example, as a result of normal grinding actions of the stomach, which can wring or otherwise manipulate a deflated or deflating balloon causing a quantity of liquid to be trapped therein. In some instances, an intragastric balloon may have a size such that even in a mostly deflated or entirely deflated configuration, the intragastric balloon risks causing a blockage in the digestive system if the intragastric balloon remains in a single piece.

The self-inflating (also referred to as automatic inflating) or inflatable (also referred to as manually inflating) intragastric balloon can be provided with mechanisms to initiate or facilitate deflation and/or to sever the intragastric balloon into a plurality of separate pieces. In some embodiments, the mechanisms can reliably control timing of deflation. In preferred embodiments, the balloon auto-deflates and passes through the stomach, through the lower gastrointestinal tract, and out of the body at the end of its pre-determined useful life (non-spontaneous), preferably between 30 and 90 days but can be timed to deflate within 6, 8, 10 or 12 months or longer. In some embodiments described below, the timing of deflation can be accomplished via the external gastric environment (by conditions of temperature, humidity, solubility, and/or pH, for example) or via the environment within the lumen of the inflated balloon. Controlling the initiation of the self-deflation process by manipulating the internal balloon environment can allow for consistency.

In other embodiments, timing of deflation can be controlled by an external signal. For example, deflation may be initiated in response to an external signal, such as, for example, an RF signal, a magnetic signal, an ultrasound signal, or any other suitable signal capable of passing through the body of an obese patient.

In some embodiments, the intragastric balloon can be provided with mechanisms to reliably control the duration and extent of deflation. An intragastric balloon that deflates over an extended period of time may enter the intestinal tract prior to complete deflation and may cause a blockage therein. In some embodiments, the intragastric balloon can be provided with mechanisms configured to cause rapid, instantaneous, or near instantaneous deflation. The mechanisms may be configured to cause complete or near complete deflation of the intragastric balloon.

The intragastric balloon can also be provided with mechanisms to reliably control fragmentation of the balloon into a plurality of separate pieces. Smaller pieces of an intragastric balloon may more readily pass through the digestive system. In some embodiments, the intragastric balloon can be provided with mechanism configured to cause fragmentation of the balloon into two separate halves. The intragastric balloon can also be provided with mechanisms configured to cause fragmentation along one or more seams, welds, folds, or the like, of the intragastric balloon.

A mechanism to facilitate passing of the intragastric balloon can include a mechanism for melting or burning one or more portions of the intragastric balloon to break, form a hole in, or otherwise damage the intragastric balloon. Melting or burning one or more portions of the intragastric balloon can be achieved by applying heat to those portions of the intragastric balloon. One or more conductive materials can be dispersed within the interior of the balloon or about the exterior of the balloon to facilitate the flow of electrical current to provide heat to one or more portions of the intragastric balloon to melt or burn those portions of the intragastric balloon. The conductive materials can be configured to melt or burn one or more holes in the outer layer of the intragastric balloon or to melt or burn along cross section of the intragastric balloon to fragment the intragastric balloon into two or more pieces. In some embodiments, formation of one or more holes in the outer layer of the intragastric balloon can weaken the structural integrity of at least a portion of the outer layer of the balloon so as to encourage additional breakage of the outer layer of the intragastric balloon.

The conductive materials can include any biocompatible conductive metal. The conductive materials can include, but are not limited to, silver, copper, gold, aluminum, nickel, iron, platinum, stainless steel, titanium, etc., and alloys of the same. The conductive materials can include any biocompatible conductive polymer. The conductive materials can include, but are not limited to, polythiophene, polyaniline, polypyrrole, any derivatives thereof, and any other conductive polymer suitable for implantation into the body. In some embodiments, the conductive materials can include one or more conductive metals in combination with one or more conductive polymers.

The conductive materials can include one or more wires or other elongated conductive materials or traces. The conductive material can be deposited or printed in a form of "wires" or "traces" on the interior of the balloon using various deposition techniques, such as electron beam deposition, screen printing techniques, or sputter deposition. Certain conductive polymers, or polymers mixed with a conductive metal component, can also be employed. The wires can be dispersed around the interior of the intragastric balloon, on the exterior of the intragastric balloon, or in a seam, weld, or fold of the intragastric balloon. In some embodiments, the intragastric balloon can include a scaffold of wires. The wires may be positioned about the outer layer of the intragastric balloon along a cross section or circumference of the intragastric balloon to melt or burn one or more holes in the intragastric balloon or to melt or burn through the entire cross section or circumference of the intragastric balloon to separate the balloon into two or more pieces. The wires can be embedded into a seam, weld, fold, or the like. The metals can also be embedded in a balloon having in an inverted, noninverted or overlapped balloon configuration as described herein. In some embodiments, one or more wires can be connected or selectively connected to each other via, for example, a switch, for forming a circuit to direct an electric current to one or more portions of the balloon.

The wires can be ultra-fine or hair thin to facilitate passage through the digestive system following deflation of the intragastric balloon. For example, the may have a size of less than 26-gauge, at least 26-gauge, at least 28-gauge, at least 30-gauge, at least 32 gauge, at least 34 gauge, at least 36 gauge, at least 38 gauge, or at least 40 gauge. In some embodiments, the wires 125 and 130 may have a size between 24-gauge and 26-gauge, between 26-gauge and 28-gauge, between 28-gauge and 30-gauge, between 30-gauge and 32-gauge, between 32-gauge and 34-gauge, between 34-gauge and 36-gauge, between 36-gauge and 38-gauge, between 38-gauge and 40-gauge, or greater that 40-gauge. The wires 125 and 130 may also be flexible to facilitate passage through the digestive system. In some embodiments, one or more of the wires 125 and 130 can be composed of a metal that readily dissolves in stomach acid.

In some embodiments, a layer of molecules of conductive material can be deposited over one or more sections of the interior of the balloon using various deposition techniques, such as, for example, electron beam deposition or sputter deposition. In some embodiments, one or more layers of molecules of conductive material can be deposited on the interior of the balloon in a wire-like arrangement. For example, one or more layers of molecules of conductive material can be arranged within the interior of the balloon in a similar configuration to a plurality of wires. Layers of molecules of conductive material deposited using any of the various deposition techniques can act in a similar manner to the conductive wires described herein.

The mechanism for melting or burning a hole in one or more sections of the balloon can further include a power source to provide a current to the conductive materials. In some embodiments, a power source can include one or more batteries. The one or more batteries can be connected or selectively connected to the conductive materials via, for example, a switch. In some embodiments a current can be provided through the use of a saline solution with a copper wire and an aluminum wire. A saline solution can be injected into the intragastric balloon during manufacture, during inflation, or at any other time prior to deflation. A current can be created by connecting the copper wire and aluminum wire in the presence of the saline solution. In some embodiments, the copper wire and aluminum wire can be connected via a switch or microswitch to form a circuit.

In some embodiments the power supply can include a module capable of supplying a current to a circuit inductively. In some embodiments, the source of power can be external to the intragastric balloon. For example, the circuit can derive power from an external electromagnetic radiofrequency (RF) source, as occurs with passive RF telemetry techniques, such as RF coupling, that are well known to those skilled in the art. The circuit can be energized by a time-varying RF wave that is transmitted by an external transceiver.

Other possible sources of power for the circuit include light, body heat, and the potential difference in voltage that can be generated in body fluids and detected by electrodes made of varying materials. The harnessing of such power sources for biotelemetry purposes is well described in R. Stuart Mackay: *Bio-Medical Telemetry, Sensing and Transmitting Biological Information from Animals and Man*, 2d ed., IEEE Press, N.Y., 1993, whose section entitled "Electronics: Power Sources" is hereby incorporated herein by reference in its entirety.

In some embodiments, the power source or switch can be part of an electronics package. An electronics package can include a processing unit, such as a processor, microprocessor, or microchip configured to perform logical operations to provide power to the conductive materials and/or or complete a circuit with the conductive materials. The electronics package can further include a memory, which may include both read only memory (ROM) and random access memory (RAM). The memory can provide instructions and data to processing unit.

The electronics package can also include a communications module for transmitting and/or receiving data from an external device. The communications module can include a receiver, a transmitter, and or a transceiver. The communications module can be configured to communicate with an external device via any communications medium capable of transmission through the body of a patient. For example, the communications module can be configured to receive an RF signal, a magnetic signal, an ultrasound signal, or any other suitable signal from an external device.

In some embodiments, the electronics package can further include a timer. The timer can be configured to measure or count down a length of time from an activation or initiation of the timer or can be a real-time clock configured to track the current time. The timer can be connected to the power source, processing unit, and/or switch to enable completion of a circuit and/or the delivery of current to the conducting materials at a predetermined time or after a predetermined amount of time from activation or initiation of the timer. In some embodiments, the time can be activated prior to swallowing the balloon. The timer may be electrically connected to a button, switch, trigger, or the like for initiation of the timer. Alternatively, the timer can be initiated in response to a signal from an external device in wired or wireless communication with electronics package. For example, the timer can be activated in response to an RF signal transmitted prior to swallowing, transmitted when the intragastric balloon reaches the stomach, or transmitted at a time after the intragastric balloon has been in the stomach.

The electronics package can further include one or more sensors. The one or more sensors can be configured to detect the presence of the intragastric balloon in a patient's stomach. For example, the sensors can be configured to detect a liquid or acidic environment. In some embodiments, the sensors can be configured to detect that the balloon has been inflated. For example, the sensors can be configured to detect balloon pressure. In some embodiments, the timer is configured to initiate or activate based on one or more readings from the sensors. For example, the timer can initiate or activate in response to a determination that the intragastric balloon is inside of the patient's stomach or that the intragastric balloon has been inflated.

In some embodiments, a mechanism can be provided for triggering completion of the circuit and/or the supply of power on demand. For example, in some embodiments, a signal can be transmitted from an external device to trigger completion of the circuit and/or the supply of power. In some embodiments, a capsule or pill can include a trigger device for actuating the electronics package to complete the circuit and/or supply power. The capsule can include a transmitter or transceiver for transmitting a signal to the electronics package. The capsule can be swallowed by the patient to cause completion of the circuit and/or the supply of power to the circuit. In some embodiments, the electronics package can be configured to complete the circuit and/or supply power in response to contact with stomach acid. In embodiments in which the electronics package is positioned in an interior section of the balloon, the electronics package can be configured to complete the circuit and/or supply power if the balloon receives a premature tear or puncture allowing stomach acid to enter the interior of the balloon.

A mechanism for burning or melting one or more portions of the intragastric balloon, as described herein, can be used in conjunction with one or more materials or surface alterations configured to more readily enable breakage, fracture, or dissolution of the intragastric balloon. As described with respect to various mechanisms below, the intragastric balloon can include one or more degradable sections or components. The intragastric balloon can also include one or more sections of materials that are designed to readily tear in response to particular forces and events, such as, for example, a highly oriented polymer film. The intragastric balloon may further include one or more surface alterations such as a scored area or weakened bonding area. These mechanisms, when used in conjunction with a mechanism for melting or burning one or more sections of the intragastric balloon can enhance the rate or extent of breakage of the intragastric balloon.

A mechanism to facilitate passing involves an erosion mechanism that allows for the balloon to be broken down into a size that has a higher probability of predictably passing through the lower gastrointestinal system. Preferably, the size of the balloon or each piece of the balloon as deflated is less than 5 cm long and 2 cm thick (similar to various foreign objects of similar size that have been shown to pass predictably and easily through the pyloric sphincter). This can be accomplished by providing the balloon with "erodible seams." One seam that breaks the balloon open into (at a minimum) two halves, or more seams are provided so that a plurality of smaller balloon pieces is produced in the dissociation reaction. The number of seams used can be selected based on the original surface area of the balloon and what is required to dissociate the balloon into pieces that are of a size that can predictably pass through the gastrointestinal tract more easily. The seams can be constructed using an erodible, disintegrable, degradable or other such material that is preferably tissue-compatible and degrades into non-toxic products or is a material that slowly hydrolyzes and/or dissolves over time (e.g., poly(lactic-co-glycolic acid) (PLGA), poly(lactide-co-glycolide) (PLG), polyglycolic acid (PGA), polycaprolactone (PCL), polyesteramide (PEA), polyhydroxyalkanoate (PHBV), polybutylene succinate adipate (PBSA), aromatic copolyesters (PBAT), poly(lactide-co-caprolactone) (PLCL), polyvinyl alcohol (PVOH), polylactic acid (PLA), poly-L-lactic acid PLAA, pullulan, polyethylene glycol (PEG), polyanhydrides, polyorthoesters, polyaryletherketones (PEEK), multi-block polyetheresters, poliglecaprone, polydioxanone, polytrimethylene carbonate, and other similar materials). These erodible, disintegrable, or degradable materials can be used alone, or in combination with other materials, or can be cast into/co-extruded, laminated, and/or dip coated in conjunction with non-erodible polymers (e.g., PET or the like) and employed in the construction of the balloon. The rate of seam erosion can be controlled by using a material affected by, e.g., the external gastric environment pH, liquid, humidity, temperature, or a combination thereof. Seams can be single layer consisting of only erodible material, or multi-layer. The timing of self-deflation can be further controlled by the design of the seam layers, e.g., making the reaction and/or degradation of the seam material dependent on the internal environment of the balloon instead of the external environment. By manipulating the reaction, such that erosion or degradation is initiated by the balloon's internal environment (e.g., the balloon's internal pH, humidity, or other factors), any impact of person-to-person gastric variability (pH, etc.) on erosion timing is minimized. The internal balloon environment can be manipulated by adding excess water at injection to create a more humid internal environment, or the amount of constituents added can be varied to manipulate the pH, etc. Degradation timing can also be facilitated by the thickness of the polymer wall and exposure time. Degradation/erosion are timed such that they occur once a pre-determined balloon useful life is completed (e.g., inflation is maintained for from 25 to 90 days, for up to 6, 8, 10 or 12 months, or more than 12 months, in vivo in the stomach before degradation/erosion results in formation of an opening permitting deflation). The mechanism of using an erodible material or a material that mechanically fails after a pre-specified time is similar for all embodiments for deflation mechanisms described below as well. The timing of degradation or erosion can be controlled using the external gastric environment (e.g., by conditions of temperature, humidity, solubility, and/or pH, for example) and/or can be controlled by conditions within the lumen of the balloon (e.g., by conditions of humidity and/or pH of residual liquid in the balloon).

Another mechanism to facilitate passing can include a polymer film tearing mechanism that allows for the balloon to be broken down into a size that has a higher probability of predictably passing through the lower gastrointestinal system. Preferably, the size of the balloon or size of each piece of the balloon as deflated is less than 5 cm long and 2 cm wide (similar to various foreign objects of similar size that have been shown to pass predictably and easily through the pyloric sphincter). This can be accomplished by providing the balloon with a section of highly oriented, or uni-directional, polymer film. The polymer film can include a plurality of polymer molecules, all or substantially all of which are aligned parallel to a single longitudinal axis. The uni-directional orientation of the polymer molecules within the polymer film can allow the polymer film to readily tear along the longitudinal axis while substantially preventing tearing perpendicular to the longitudinal axis. A pulling force or a break in polymer film in combination with shear stress on the polymer film can cause the polymer film to tear along the longitudinal axis. In some embodiments, a break in the polymer film in the presence of shear stress can expand rapidly, instantaneously, or semi-instantaneously to sever or "un-zip" the balloon along the length of the polymer film. Tension of the outer layer of the intragastric balloon due to inflation can provide sufficient shear stress to sever the polymer film following formation of a break or hole in the polymer film. In embodiments in which the polymer film wraps around a section of the balloon, a break in the polymer film can expand to sever the balloon into at least two pieces. One or more bands of polymer film wrapping around a section of the balloon can be provided so that a plurality of smaller balloon pieces can be produced in response to breaks in the polymer film. The number of bands of polymer film used can be selected based on the original surface area of the balloon and what is required to fragment the balloon into pieces that are of a size that can predictably pass through the gastrointestinal tract more easily. In some embodiments, the polymer film can be incorporated into a seam or weld of the intragastric balloon. Polymer molecules running in parallel with the seam or weld can allow for tearing or un-zipping of the balloon along the seam or weld to fracture the balloon into two pieces, or more pieces if multiple seams or welds having containing the polymer film are used.

The polymer film can be constructed with one or more preferably tissue-compatible polymers, such as, e.g., polyolefins, such as polyethylene (PE), linear low-density polyethylene (LLDPE), high density polyethylene (HDPE), polypropylene (PP), low density ethylene/vinyl acetate copolymer, ethylene/vinyl alcohol copolymer, polyamide resin, polystyrene, cyclic olefin copolymers, and co-polymers and grafted polymers thereof, or any other suitable polymer known in the art. In some embodiments, the highly oriented polymer film includes polyethylene terephthalate (PET).

Some embodiments may include a mechanism for facilitating formation of a hole in the polymer film. In some embodiments, the polymer film can be constructed in combination with an erodible, disintegrable, degradable or other such material that is preferably tissue-compatible and degrades into non-toxic products or is a material that slowly hydrolyzes and/or dissolves over time, such as those described above with respect to the erodible seam. Erosion of the erodible disintegrable, degradable or other such material can cause the formation of the breakages or holes in the polymer film, allowing for the break to expand along the longitudinal axis of the polymer film in the presence of shear stress.

In some embodiments, an electronics package including a processing unit configured to perform logical operations to initiate or facilitate formation of one or more holes in the polymer film can be functionally connected to the polymer film. The electronics package can further include one or more of a communications module, a memory, a timer, which can function in a similar manner to that described with respect to the processing circuit of the mechanism for burning or melting one or more portions of the intragastric balloon.

The processing unit can be a processor, microprocessor, or microchip configured to perform logical operations to initiate or facilitate formation of one or more holes in the polymer film. The memory may include both read only memory (ROM) and random access memory (RAM) and can provide instructions and data to processing unit.

The communications module can be configured to transmit and/or receive data from an external device. The communications module can include a receiver, a transmitter, and or a transceiver. The communications module can be configured to communicate with an external device via any communications medium capable of transmission through the body of a patient. For example, the communications module can be configured to receive an RF signal, a magnetic signal, an ultrasound signal, or any other suitable signal from an external device.

The timer can be configured to measure or count down a length of time from an activation or initiation of the timer or can be a real-time clock configured to track the current time. The timer can be connected to the processing unit to enable formation of one or more holes in the polymer film at a predetermined time or after a predetermined amount of time from activation or initiation of the timer. In some embodiments, the timer can be activated prior to swallowing the balloon. The timer may be electrically connected to a button, switch, trigger, or the like for initiation of the timer. Alternatively, the timer can be initiated in response to a signal from an external device in wired or wireless communication with electronics package. For example, the timer can be activated in response to an RF signal transmitted prior to swallowing, transmitted when the intragastric balloon reaches the stomach, or transmitted at a time after the intragastric balloon has been in the stomach.

The electronics package can further include one or more sensors. The one or more sensors can be configured to detect the presence of the intragastric balloon in a patient's stomach. For example, the sensors can be configured to detect a liquid or acidic environment. In some embodiments, the sensors can be configured to detect that the balloon has been inflated. For example, the sensors can be configured to detect balloon pressure. In some embodiments, the timer is configured to initiate or activate based on one or more readings from the sensors. For example, the timer can initiate or activate in response to a determination that the intragastric balloon is inside of the patient's stomach or that the intragastric balloon has been inflated.

A mechanism can be provided for triggering the processing unit to cause formation of a hole in the polymer film. For example, in some embodiments, a signal can be transmitted from an external device to formation of a hole. In some embodiments, a capsule can include a trigger device for actuating the electronics package to form a hole in the polymer film. The capsule can include a transmitter or transceiver for transmitting a signal to the electronics package. The capsule can be swallowed by the patient to cause initiation of formation of a hole in the polymer film. In some embodiments, the electronics package can be configured to cause hole formation in response to contact with stomach acid. In embodiments in which the electronics package is positioned in an interior section of the balloon, the electronics package can be configured to cause hole formation in the polymer film if the intragastric balloon receives a premature tear or puncture allowing stomach acid to enter the interior of the balloon.

In some embodiments, the mechanism for burning or melting one or more portions of the intragastric balloon can be incorporated into the mechanism for forming one or more holes in the polymer film. The conductive materials of the mechanism for burning or melting one or more portions of the intragastric balloon can be positioned along one or more sections of the polymer film to cause hole formation therein.

The mechanism of using a highly oriented polymer film that severs in response to the formation of a hole therein when under shear stress can be incorporated into the embodiments for deflation mechanisms described below as well.

In other embodiments, the patch applied to allow for inverted seams as described above and/or one or more additional patches or other structures added to the balloon construction are made out of an erodible, degradable, or dissolvable material (natural or synthetic) and are incorporated into the wall of the balloon. The patch(s) are of sufficient size to ensure opening of a sufficient surface area to cause rapid deflation, and to prevent re-inflation by seepage of stomach fluid into the balloon. The balloon patch(s) comprise materials that can be applied to the balloon such that a substantially smooth surface is maintained, and preferably comprise a single layer or multi-layered material. The patch(s) are constructed using an erodible, disintegrable, degradable or other such material that is preferably tissue-compatible and degrades into non-toxic products or is a material that slowly hydrolyzes and/or dissolves over time (e.g., poly(lactic-co-glycolic acid) (PLGA), poly(lactide-co-glycolide) (PLG), polyglycolic acid (PGA), polycaprolactone (PCL), polyesteramide (PEA), polyhydroxyalkanoate (PHBV), polybutylene succinate adipate (PBSA), aromatic copolyesters (PBAT), poly (lactide-co-caprolactone) (PLCL), polyvinyl alcohol (PVOH), polylactic acid (PLA), poly-L-lactic acid PLAA, pullulan, polyethylene glycol (PEG), polyanhydrides, polyorthoesters, polyaryletherketones (PEEK), multi-block polyetheresters, poliglecaprone, polydioxanone, polytrimethylene carbonate, and other similar materials). These erodible, disintegrable, or degradable materials can be used alone, or in combination with other materials, or can be cast into/co-extruded, laminated, and/or dip coated in conjunction with non-erodible polymers (e.g., PET or the like) and employed in the construction of the balloon. Degradation/erosion occurs, is initiated by, and/or is controlled by the gastric environment (e.g., by conditions of temperature, humidity, solubility, and/or pH, for example), or is controlled within the lumen of the balloon (e.g., by conditions of humidity and/or derived pH, for example) based on what the patch is exposed to. Thickness of the polymer as well as environment which affects degradation and time of exposure can also facilitate degradation timing. Degradation/erosion are timed such that they occur once the pre-determined balloon useful life is completed (e.g., inflation is maintained for from 25 to 90 days in vivo in the stomach before degradation/erosion results in formation of an opening permitting deflation). As an alternative to (or in connection with) using an degradable material for the patch, the patch can comprise a similar fluid retention barrier film or the same film as the remaining wall of the balloon which is adhered to the balloon using a weak adhesive, or welded or adhered such that after a specified amount of time the patch delaminates from the applied area and allows for an opening for inflation fluid release for deflation. Or if deemed necessary for rapid deflation the entire balloon composite wall can be made of the erodible material. As another alternative to (or in connection with) using a degradable material for the patch, the patch can comprise a highly oriented polymer material configured to sever in response to shear stress when a hole is formed therein.

In other embodiments, a plug or plugs (optionally in conjunction another degradable retaining structure) can be incorporated into the balloon construction and can consist, all or in part, of an erodible, disintegrable, or otherwise degradable synthetic or natural polymer similar to those described above (e.g., PLGA, PLAA, PEG, or the like). The plug can be formed into various shapes (e.g., cylinder shape) to achieve various surface-to-volume ratios so as to provide a preselected and predictable bulk degradation pattern for the erodible polymer. The plug can incorporate a releasing mechanism that can be chemically initiated after degradation/erosion begins, such that the septum or plug material pops out of the balloon or falls inside of the balloon, thereby creating a passageway for fluid release and subsequent deflation of the balloon. Mechanical additions that can be used in conjunction with a plug include a degradable/erodible/disintegrable material that holds a plug (e.g., of a non-degradable or degradable material) in place or a compressed spring housed within the retaining structure or plug structure. More specifically one preferred embodiment to achieve deflation can comprise a housing, a radial seal, a solid eroding core, and a protective film attached to the external surface of the eroding core. The inside of the eroding core is exposed to the internal balloon liquid. The core creates a compressive force that holds the seal against the housing. As the core erodes, the compression between the housing and the radial seal is reduced until there is clearance between the housing and the seal. Once there is clearance, gas can move freely from the inside of the balloon to the outside environment. The seal can fall out of the housing and into the balloon. The diameter, length, and material types can be adjusted in order to create the deflation at a desired time point. Example materials for each component used to achieve this deflation mechanism can be as follows: Housing: Biocompatible structural material, capable of withstanding enough radial force to form an air tight seal. Possible materials include: polyethylene, polypropylene, polyurethane, UHMWPE, titanium, stainless steel, cobalt chrome, PEEK, or nylon; Radial Seal: The radial seal needs to be composed of a biocompatible elastic material, capable of providing liquid and gas barrier to acidic environments. Possible materials include: silicon, polyurethane, and latex; Eroding Core: The eroding core needs to be a material capable of breaking down at a predictable rate at given environmental conditions. Possible materials include: PLGA, PLA, or other polyanhydrides that are capable of losing integrity over time or any materials listed above that provide erodible characteristics.

For the spring mechanism, once the material degrades, the spring is released and/or the plug/septum is pulled into the balloon or pushed out of the balloon, thus releasing fluid once an orifice has been created by release of the spring mechanism and pushing out or pulling in of the plug.

Another preferred embodiment is comprised of a septum, moisture eroding material inside an inlet port, and moisture absorbing expansion material. The eroding materials slowly erode away when exposed to moisture, eventually exposing the moisture absorbing expansion material. When the moisture expanding material begins to absorb moisture, the expansion pulls the septum out of position in the head by pushing against a septum lip or a ring attached to the septum.

Pulling the septum out of position causes an immediate deflation of the balloon. In order to protect the expanding material from moisture until a desired timepoint, the expanding material can be sheathed in water blocking materials, such as parylene, as well as slowly water degrading materials. The moisture contact can be controlled by small inlet ports. The inlet ports can be small holes, or a wick material that draws moisture in a controlled manner. The desired deflation time is achieved through a combination of eroding materials, blocking materials, and inlet port sizing.

In certain embodiments, the balloon can incorporate one or more plugs in the wall of the balloon that contain a compressed pellet or gas releasing pellet. The pellet can be comprised of any combination of constituents that, when activated, emit CO2 gas (e.g., sodium bicarbonate and citric acid, or potassium bicarbonate and citric acid, or the like). The pellet can be in tablet or rod form protected by an erodible, disintegrable, or degradable material that is preferably tissue-compatible and degrades into non-toxic products or that slowly hydrolyzes and/or dissolves similarly to the plugs and patches described above (e.g., poly(lactic-co-glycolic acid) (PLGA), polyvinyl alcohol (PVOH), polylactic acid (PLA), poly-L-lactic acid PLAA, Pullulan, Polyethylene Glycol, polyanhydrides, polyorthoesters, polyaryletherketones (PEEK), multi-block polyetheresters, poliglecaprone, polydioxanone, polytrimethylene carbonate, and other like materials). Degradation/erosion of the plug initiates the reaction of the two chemicals in the pellet and subsequently leads to formation of gas (e.g., CO2). As sufficient gas is trapped or built up, sufficient pressure is eventually generated to push out the softened polymer material and create a larger channel for the CO2 gas in the balloon to escape. External pressure applied by the stomach to the balloon (e.g., squeezing) can contribute to the process of creating a larger channel. Dimensions and properties of the plug (diameter, thickness, composition, molecular weight, etc.) comprised of the polymer drives the timing of degradation.

In other embodiments, plugs or patches of different shapes or sizes similar to those of the plugs described above can be employed within the balloon lumen in a multi-layer configuration including a semi-permeable membrane to facilitate balloon deflation. The plug or patch is made of similar degradable/erodible/dissolvable material as described above (e.g., poly(lactic-co-glycolic acid) (PLGA), polyvinyl alcohol (PVOH), polylactic acid (PLA), PLAA, pullulan, and other like materials), optionally in combination with a highly oriented polymer film, and contains a compartment enclosed by a semi-permeable membrane (impermeable to an osmolyte) that contains a concentrated solution of a solute or osmolyte (such as glucose, sucrose, other sugars, salts, or combination thereof). Once the plug or patch begins to degrade or erode, the water molecules move by osmosis down the water gradient from the region of greater water concentration to the region of lower water concentration across the semi-permeable membrane into the hypertonic solution in the compartment. The compartment containing the osmolyte swells and eventually bursts, pushing the membranes and the degraded plug or patch out, thereby allowing rapid gas loss through the newly created channels or areas.

In certain embodiments, a balloon composed of a septum, moisture eroding material inside an inlet port, and moisture absorbing expansion material is employed. The eroding materials slowly erode away when exposed to moisture, eventually exposing the moisture absorbing expansion material. When the moisture expanding material begins to absorb moisture, the expansion pulls the septum out of position in the head by pushing against a septum lip or a ring attached to the septum. Pulling the septum out of position causes an immediate deflation of the balloon. In order to protect the expanding material from moisture until a desired time point has been reached, the expanding material can be sheathed in water blocking materials, such as parylene, as well as slowly water degrading materials. The moisture contact can be controlled by small inlet ports. The inlet ports can be small holes, or a wick material that draws moisture in a controlled manner. The desired deflation time is achieved through a combination of eroding materials, blocking materials, and inlet port sizing.

Another mechanism for self-deflation is to create a forced de-lamination scheme, which can provide a larger surface area to ensure rapid deflation. In, e.g., a balloon having a tri-layer wall, the outermost layer is substantially strong enough to hold the inflation fluid (e.g., polyethylene terephthalate (PET) or the like), the middle layer is comprised entirely of an erodible material (e.g., PVOH or the like) while the inner layer is comprised of a weaker material (e.g., polyethylene (PE) or the like). The PET or outermost layer is "scored" or hatched with erodible material to create small channels that erode over time. This creates channels such that the gastric fluid seeps into the balloon layers and starts degrading the fully erodible material. In some embodiments, the PET or outermost layer can include a highly oriented polymer film. When the erodible layer degrades or dissolves, the material that composes the innermost layer also erodes, degrades or dissolves since it is not strong enough to withstand the gastric forces/environment on its own. The balloon then collapses on itself and eventually passes through the lower gastrointestinal tract. Having an erodible layer sandwiched between a strong and weak layer facilitates timing of erosion by creating a longer path length than an erodible plug or patch affected by the gastric environment. The distance between scores or openings can also be selected so as to provide a desired deflation rate.

In another embodiment providing abrupt deflation of the balloon after a desired period of time has elapsed, the composite wall of the entire balloon or a section of the composite wall (patch) includes several material layers that are slowly penetrated by water that has been injected inside the balloon during the manufacturing process or during the inflation process. This water penetrates through the layers, eventually reaching a material that substantially expands, rupturing a thin external protective later, and creating a large hole for gas to escape and the balloon to deflate. The water expanding material is protected from liquid via a coating or sheath, such as parylene, which allows a controllable amount of moisture exposure. Once water reaches the expansion material, it exerts a force on the protective outer layer, causing it to rupture. The outer layer may be created with a weakened bonding area, a partially scored area, or other methods of ensuring a desired rupture location and to facilitate desired timing for auto-deflation to take place. There can be any number of layers between the moist environment and the moisture expanding center. Each material layer can have different erosion rates (e.g., fast or slow) and can be selected by the predetermined time deflation is desired to occur (e.g., after 30 days, 60 days, or more). By varying the number, thickness, and rate of each of the circumferential layers, the time to deflation can be accurately controlled.

Alternatively a pressure sealing button that is adhesively bonded over a perforation in the balloon material can be provided for deflation. The adhesive bonding the button erodes over time when it comes into contact with moisture derived from the gastric fluid or that has been injected inside the balloon. Once the adhesive can no longer bond and create an airtight seal between the adhesive and the button, the balloon will rapidly deflate. By controlling the hole size and moisture exposure of the adhesive, the erosion time can be accurately predicted.

Deflation can also be facilitated by creating a series of connecting ports within the septum or on another similar structure attached to the balloon composite wall. The ports can be constructed using a water- or acid-dissolving, biologically compatible, low permeability substance, such as gelatin. The diameter of the hole, number of holes, channel width, and channel length can all be adjusted to control the dissolving parameters. Once the material in the ports and channel is dissolved, there is a clear path for gas trapped in the balloon to escape, eventually resulting in a deflated balloon. The water can be gastric fluid or controlled internally by including water inside the balloon at assembly or during the inflation process. There can be a plurality of port openings to guarantee gas transmits. Additionally, there are several variables that can be adjusted to control dissolution time: size of the port openings; number of port openings; the length of the internal channel; the width of the internal channel; and the rate of material dissolution. The port/channel layout design can ensure that only a small amount of surface area is exposed to moisture at any particular time, thereby controlling the rate of erosion and ultimately deflation.

Preferred embodiments of deflation mechanisms are described below with reference to FIGS. 1-7.

Electrical Deflation Mechanism

FIG. 1 shows an embodiment of an intragastric balloon 100 having a top half 105, a bottom half 110, a seam 115, and a head 120. The head 120 can function in generally the same manner as any of the heads described herein. The top half 105 and bottom half 110 are connected by the seam 115. The balloon 100 is shown in a deflated configuration prior to insertion into a patient and inflation of the balloon. The bottom half 110 is shown inverted within the top half 105. A first wire 125 and a second wire 130 are embedded in the seam 115. The first wire 125 and second wire 130 can be embedded in the seam 115 during manufacturing of the balloon 100, for example, when the two halves of the balloon are inverted onto a seam welder fixture. The first wire 125 and the second wire 130 can be connected to an electronics package 135. The electronics package 135 can also be positioned within the seam 115.

An electric current can be generated in the first wire 125 and second wire 130 to cause a voltage to be produced in the wires 125 and 130 that is sufficient to rupture, burn through, or otherwise damage the seam 115. The wires 125 and 130 can burn through several portions of the seam 115, causing formation of a plurality of holes in the balloon 100. The holes can allow for rapid, instantaneous, or near instantaneous deflation of the balloon. The wires 125 and 130 can also be configured to burn through all of substantially all of a longitudinal segment of the seam 115, causing the balloon 100 to break into at least two separate pieces. For example, the voltage produced in the wires 125 and 130 can cause a rupture of the seam that severs the top half 105 and bottom half 110 of the balloon. Separation of the balloon 100 into at least two separate pieces can cause deflation of each separate piece, allowing for the balloon to pass through the digestive system. Further, the separate pieces can be sized to be readily passable through the digestive system.

As show in FIG. 1, the wires 125 and 130 and seam 115 runs across the X-Y plane of the balloon 100. However, the wires 125 and 130 and seam 115 can run across any plane of the balloon 100, such as for example, the Y-Z plane. In alternative embodiments, the intragastric balloon 100 can include any number of additional wires and can break the intragastric balloon into any number of smaller balloon pieces. The intragastric balloon 100 can further include any number of seams in which the wires are embedded. Although an inverted configuration is shown in FIG. 1, the intragastric balloon 100 can alternatively have a noninverted or overlapped configuration as described above. While the wires 125 and 130 are embedded in the seam 115 of the balloon 100, it is envisioned that the wires can be incorporated into any section an intragastric balloon as described herein. For example, the wires 125 and 130 can be embedded in one or more folds, welds or the like.

The wires 125 and 130 can be formed of any metal or metals sufficient to conduct an electric current capable of rupturing a portion of the intragastric balloon 100, such as the seam 115. For example, the wires 125 and 130 can include, but are not limited to, silver, copper, gold, aluminum, nickel, iron, platinum, stainless steel, titanium, etc., and alloys of the same. The wires 125 and 130 can be formed of the same metal or metals or may be formed of a different metal or metals. In a preferred embodiment, one of the wires 125 and 130 is formed at least partially of copper and the other of the wires 125 and 130 is formed at least partially of aluminum.

The wires 125 and 130 can be ultra-fine or hair thin to facilitate passage through the digestive system following rupture of the balloon 100. For example, the wires 125 and 130 may have a size of less than 26-gauge, at least 26-gauge, at least 28-gauge, at least 30-gauge, at least 32-gauge, at least 34-gauge, at least 36-gauge, at least 38-gauge, or at least 40-gauge. In some embodiments, the wires 125 and 130 may have a size between 24-gauge and 26-gauge, between 26-gauge and 28-gauge, between 28-gauge and 30-gauge, between 30-gauge and 32-gauge, between 32-gauge and 34-gauge, between 34-gauge and 36-gauge, between 36-gauge and 38-gauge, between 38-gauge and 40-gauge, or greater that 40-gauge. The wires 125 and 130 may also be flexible to facilitate passage through the digestive system. In some embodiments, one or more of the wires 125 and 130 can be composed of a metal that readily dissolves in stomach acid.

In some embodiments, the electronics package 135 can be configured to introduce or facilitate introduction of a current to the wires 125 and 130. The electronics package 135 can include a processing unit, such as a processor, microprocessor, or microchip configured to perform logical operations to provide power to the conductive materials and/or or complete a circuit with the conductive materials. The electronics package can further include a memory, which can provide instructions and data to processing unit.

In a preferred embodiment, the electronics package 135 can be configured to complete a circuit between the wire 125 and a wire 130 in order to cause the generation of a current in the wires 125 and 130 at a predetermined time or in response to a trigger. For example the electronics package 135 can include a switch that can be configured to complete the circuit at a predetermined time or in response to a trigger.

The gastric balloon 100 can further include one or more power sources for supplying a current to a closed circuit including wires 125 and 130. As described above, a saline solution can be injected in the interior of the balloon 100 during manufacture or during inflation, or at any time prior to deflation. In a preferred embodiment, in which one of the wires 125 and 130 includes copper and the other of the wires 125 and 130 includes aluminum, a current can be created by connecting the copper wire and the aluminum wire in the presence of the saline solution, for example, by connecting the circuit via electronics package 135.

Alternatively, the electronics package 135 can include one more power sources, such as for example, a battery, that can supply power to wires 125 and 130. For example, the one or more power sources can supply power to the circuit when the circuit is connected via the switch of the electronics package 135.

In some embodiments, a power source can include a module capable of supplying a current to the circuit inductively. In some embodiments, the source of power can be external to the balloon 100. For example, the circuit can derive power from an external electromagnetic radiofrequency (RF) source, as occurs with passive RF telemetry techniques, such as RF coupling, that are well known to those skilled in the art. The circuit can be energized by a time-varying RF wave that is transmitted by an external transceiver.

Other possible sources of power for the circuit include light, body heat, and the potential difference in voltage that can be generated in body fluids and detected by electrodes made of varying materials. The harnessing of such power sources for biotelemetry purposes is well described in R. Stuart Mackay: *Bio-Medical Telemetry, Sensing and Transmitting Biological Information from Animals and Man*, 2d ed., IEEE Press, N.Y., 1993, whose section entitled "Electronics: Power Sources" is hereby incorporated herein by reference in its entirety.

In some embodiments, the electronics package 135 may further include a timer. The electronics package 135 can be configured to complete the circuit including wires 125 and 130, or to otherwise initiate generation of current in the wires 125 and 130, at a predetermined time. For example, the electronics package 135 can be configured to complete the circuit or to otherwise initiate generation of current in the wires 125 and 130, following a particular length of time after activation of the timer, such as for example, after 3 months, after 30 days, after 45 days, after 60 days, after 75 days, after 90 days, after one month, after 2 months, after 6 months, after 8 months, after 10 months or after 12 months. Similarly, the electronics chip can be configured to supply current, via a power source, to the wires 125 and 130 at a predetermined time or following a particular length of time after activation of the timer. The timer can be initiated prior to swallowing of the intragastric balloon 100 or at a time when the intragastric balloon 100 is positioned within the stomach. The timer may be electrically connected to a button, switch, trigger, or the like for initiation of the timer. Alternatively, the timer can be initiated in response to a signal from an external device in wired or wireless communication with the electronics package 135. For example, the timer can be activated in response to an RF signal transmitted prior to swallowing, transmitted when the intragastric balloon reaches the stomach, or transmitted at a time after the intragastric balloon has been in the stomach.

The electronics package 135 can further include a communications module, such as a receiver, a transmitter, a transceiver, or the like for communicating with an external device. In some embodiments, the communications module can be configured to receive instructions for activating the timer, connecting the wires 125 and 130 via, for example, a switch, and/or for supplying power to the wires 125 and 130. The electronics package 135 can be configured to activate the timer, connect the wires 125 and 130, and/or supply power to the wires 125 and 130 in response to receiving a signal at the communications module. The communications module can be configured to receive an RF signal, a magnetic signal, an ultrasound signal, or any other suitable signal from an external device.

In some embodiments, a mechanism can be provided for triggering completion of the circuit by connecting wires 125 and 130 or the supply of power to the wires 125 and 130 on demand. For example, as described above, a signal can be transmitted from an external device to trigger completion of the circuit or the supply of power. In some embodiments, a capsule can include a trigger device for actuating the electronics package 135 to complete the circuit. The capsule can be swallowed by the patient to cause completion of the circuit or the supply of power to the wires 125 and 130. In some embodiments, the capsule includes a transmitter or transceiver transmitting a signal that, when received by the electronics package 135, can trigger the electronics package 135 to connect the wires 125 and 130 and/or supply power to the wires 125 and 130.

In some embodiments, the electronics package 135 can be configured to connect the wires 125 and 130 and/or supply power to the wires 125 and 130 in response to contact with stomach acid. For example, the electronics package 135 can be configured to activate a switch and/or power source if the balloon 100 receives a premature tear or puncture allowing stomach acid to enter the interior of the balloon 100.

Highly Oriented Polymer Film Deflation Mechanism

In some embodiments the intragastric balloon device can consist at least partially of a highly oriented, or uni-directionally oriented, polymer film. FIG. 2 shows a highly oriented polymer film 200 comprises a plurality of polymer molecules 205 and having a longitudinal axis A. Polymer film 200 can be configured to be substantially parallel with the direction of extrusion during fabrication. As shown in FIG. 2, all or substantially all the polymer molecules 205 can be oriented to be parallel with the longitudinal axis A. The uni-directional orientation of the polymer molecules 205 within the polymer film 200 can allow the film 200 to readily tear along the axis A but not perpendicularly to the axis A. Accordingly, when the film 200 is broken or pulled apart, the film 200 can tear parallel with the axis A, but will not tear perpendicularly to the axis A. In some embodiments, the film 200 can tear rapidly, instantaneously, or semi-instantaneously when the film 200 is broken or pulled apart.

FIG. 3 shows an example of the film 200 tearing in parallel with the axis A from a first end 240A of the polymer film 200 towards a second end 240B of the polymer film 200. In the example of FIG. 3, a pulling force applied to the first end 240A of the polymer film in a direction generally perpendicular to the longitudinal axis A is represented by arrows 210. The force results in a tear in the film 200, the direction of which is represented by arrow 215. As shown, the polymer film 200 tears along the edges of a pair of the polymer molecules 205 from the first end 240A to the second end 240B of the polymer film 200.

FIGS. 4A and 4B show an example of a break in the polymer film 200. FIG. 4A shows a hole 220 that has formed in one of the polymer molecules 205 of the polymer film 200. A hole in one of the polymer molecules 205 can tend to enlarge along the length of the polymer molecules 205, in parallel with the axis A, such that a bi-directionally enlarging tear or un-zipping is created in the polymer film 200. Arrows 225 show the direction of enlargement of the hole 220. FIG. 4B shows the hole 220 after undergoing limited bi-directional enlargement. The hole 220 can continue to grow until the film 200 is torn into separate pieces. In some embodiments, formation of the hole 220 in the polymer molecule will result in rapid bi-directional enlargement resulting in a rapid, instantaneous, or semi-instantaneous separation of the film 200 into multiple separate pieces, in response to application of a shear force, as will be discussed in further detail below.

Examples of polymers that may be part of a highly oriented polymer film include, but are not limited to, polyolefins, such as polyethylene (PE), linear low-density polyethylene (LLDPE), high density polyethylene (HDPE), polypropylene (PP), low density ethylene/vinyl acetate copolymer, ethylene/vinyl alcohol copolymer, polyamide resin, polystyrene, cyclic olefin copolymers, and co-polymers and grafted polymers thereof, or any other suitable polymer known in the art. In some embodiments, the highly oriented polymer film comprises polyethylene terephthalate (PET).

A highly oriented polymer film, such as film 200 shown in FIGS. 2-4B can be incorporated into an intragastric balloon to facilitate separation of the balloon into multiple pieces. In some embodiments, the highly oriented polymer film can be incorporated into a seam or weld of an intragastric balloon.

FIG. 5 depicts an embodiment of a balloon 300 having a top half 305, a bottom half 310, a weld 315 and a valve 320. The valve 320 can function in generally the same manner as any of the valves described herein. The weld 315 can include a highly-oriented polymer film 325 having a plurality of polymer molecules that are oriented substantially parallel with the length of the weld, or parallel with line O of FIG. 5. In FIG. 5, the weld 315, and consequently the molecules of the polymer film 325, run parallel with the equator of the balloon 300. In FIG. 5, the balloon 300 is shown in an inflated configuration. When the balloon 300 is inflated, the weld 315 is placed under shear stress. The shear stress on the weld 315 is represented by line S of FIG. 5. Shear stress is a component of stress that is coplanar with a cross-section of a material and arises from a force vector component parallel to the cross-section. In contrast, normal stress arises from a force vector component perpendicular to the material cross section on which it acts. As shown in FIG. 5, the shear stress represented by line S pulls on the polymer film 325 in a direction perpendicular to the orientation of the polymer molecules of the polymer film 325. Due to the uni-directional orientation of the polymer molecules, the polymer film 325 will not tear easily in response to the shear stress denoted by line S. However, a break in the highly oriented polymer film 325 can allow a shear force, such as the force denoted by line S to rapidly, instantaneously, or semi-instantaneously pull one or more polymer strands apart, starting at the position of the break, which acts as a stress riser.

FIGS. 6A and 6B show an illustrative example of a break forming in the balloon 300 and the separation of the polymer film 325 in response to shear stress acting on the weld. FIG. 6A shows a hole 330 in the polymer film 325. FIG. 6A also shows arrows 335 that represents the direction of an enlargement of the hole 330 resulting from the shear stress acting on the weld 315 due to the inflated configuration of the balloon. As indicated by the arrows 335, the hole 300 will enlarge along the length of the weld 315. FIG. 6B shows the hole 330 at a time after that shown in FIG. 6A, depicting an enlargement of the hole 330 along the length of the weld 315.

The shear force resulting from inflated state of the balloon can cause the polymer molecules of the film 325 to rapidly, instantaneously, or semi-instantaneously tear or pull apart around the entire circumference of the balloon 300, which can act to sever or un-zip the weld 315 and separate the balloon 300 into two pieces, the top half 305 and the bottom half 320. FIG. 7 shows the top half 305 and bottom half 310 after the separation of the balloon along the entire length of the weld 315. The separated pieces, top half 305 and bottom half 310, can be substantially smaller than the size of a fully formed deflated balloon. For example, each piece can be less than 5 cm long and 2 cm thick. The separated pieces, top half 305 and bottom half 310, can also have a reduced capacity or no capacity to trap liquid in comparison to a fully formed deflated balloon.

As described with reference to FIGS. 5-7, the intragastric balloon 300 can be separated by shear forces acting on a break in the polymer film 325 extending around the circumference of the balloon 300. This can allow for the rapid, instantaneous, or semi-instantaneous deflation of the balloon in response to inadvertent damage to the weld of the balloon.

In some embodiments, it may also be preferable to induce separation of the balloon 300 by initiating or creating a hole, such as hole 330, in the film 325 of the balloon 300. Some embodiments can include an electronics package that is functionally connected to the polymer film 325. The electronics package can be incorporated into the weld 315 of the balloon 325. The electronics package can include a processing unit, such as a processor, microprocessor, or microchip configured to perform logical operations to initiate or facilitate formation of one or more holes in the polymer film. The electronics package can also include a memory that can provide instructions and data to processing unit.

The electronics package can further include a communications module, such as a receiver, a transmitter, a transceiver, or the like for communicating with an external device. The communications module can be configured to receive instructions for initiating or creating a break in the film 325. The electronics package can be configured to initiate or create a break upon receiving instructions from an external device or following a predefined amount of time after receiving instructions from an external device. The communications module can be configured to receive an RF signal, a magnetic signal, an ultrasound signal, or any other suitable signal from an external device.

The electronics package can further include a timer. The timer can be configured to measure or count down a length of time from an activation or initiation of the timer or can be a real-time clock configured to track the current time. The timer can be connected to the processing unit to enable formation of one or more holes in the polymer film 325 at a predetermined time or after a predetermined amount of time from activation or initiation of the timer. In some embodiments, the timer can be activated prior to swallowing the balloon 300. The timer may be electrically connected to a button, switch, trigger, or the like for initiation of the timer. Alternatively, the timer can be initiated in response to a signal from an external device in wired or wireless communication with electronics package. For example, the timer can be activated in response to an RF signal transmitted prior to swallowing, transmitted when the intragastric balloon 300 reaches the stomach, or transmitted at a time after the intragastric balloon 300 has been in the stomach.

The electronics package can also include one or more sensors. The one or more sensors can be configured to detect the presence of the balloon 300 in a patient's stomach. For example, the sensors can be configured to detect a liquid or acidic environment. In some embodiments, the sensors can be configured to detect that the balloon 300 has been inflated. For example, the sensors can be configured to detect balloon pressure. In some embodiments, the timer is configured to initiate or activate based on one or more readings from the sensors. For example, the timer can initiate or activate in response to a determination that the intragastric balloon is inside of the patient's stomach or that the intragastric balloon has been inflated.

In some embodiments, the electronics package can be configured to create a break in the film 325 by melting or burning a section the film 325. In some embodiments, the gastric balloon 300 can include a mechanism similar to that described above with respect to FIG. 1 for melting or burning a section of the film 325. For example, melting or burning of the film 325 can be performed using one or more wires, such as the first wire 125 and second wire 130 described above with reference to FIG. 1. In some embodiments, a current can be generated using a first wire containing copper and a second wire containing aluminum in the presence of salt water by closing a switch to connect the first wire and the second wire in the create a circuit. The wires can positioned within the weld 315 of the balloon 300 and in parallel with the polymer film 325 to contact and burn multiple sections of the polymer film 325. Alternatively, the wires may extend over one or more particular sections of the polymer film 325 to generate a break in the particular sections of the film 325.

A mechanism can be provided for triggering the processing unit to cause formation of a hole in the polymer film 325. For example, in some embodiments, a signal can be transmitted from an external device to the processing unit, as described above, to initiate formation of a hole. In some embodiments, a capsule can include a trigger device for actuating the electronics package to form a hole in the polymer film 325. The capsule can include a transmitter or transceiver for transmitting a signal to the electronics package. The capsule can be swallowed by the patient to trigger the electronics package to cause formation of a hole in the polymer film. In some embodiments, the electronics package can be configured to cause hole formation in response to contact with stomach acid. In embodiments in which the electronics package is positioned in an interior section of the balloon, the electronics package can be configured to cause hole formation in the polymer film if the intragastric balloon receives a premature tear or puncture allowing stomach acid to enter the interior of the balloon.

In some embodiments, the polymer film 325 can include a biodegradable component configured to degrade over a period of time. For example, the biodegradable component can be configured to degrade over 2 months, 3 months, 6 months, or 12 months. Over time, degradation of the biodegradable component can cause a break in the polymer film 325, which can cause the balloon 300 to sever or separate along the length of the polymer film under shear stress, as described above, to result in a separate top half 305 and bottom half 310.

Although FIGS. 2-7 show the polymer film extending around the equator of the balloon, one of skill in the art would recognize that a polymer film as described above could be positioned at any segment of an intragastric balloon. In some embodiments, an intragastric balloon can include multiple segments or bands of highly oriented polymer film extending around the circumference of the balloon to facilitate separation of the balloon into any number of pieces.

EXAMPLES

Film Permeability

A variety of different composite films were tested for permeability of gases as measured by $CO_2$ diffusion at 37° C. As shown in the data of Table 3, the permeability of varying composite wall constructions were evaluated and determined by their resistance to $CO_2$ diffusion rates, where the smaller the permeability test result, the higher barrier to gas diffusion the film provides. As noted, the permeability of the film and degree of barrier the film provides to gas diffusion was derived using $CO_2$ at 37° C., one of the most permeable gasses. This can be used as a surrogate to other gas diffusion rates where generally $CO_2$ is 3 to 5 times faster in diffusion across a membrane than oxygen, and nitrogen is 0.2 to 0.4 times faster than the oxygen transmission rate when these are evaluated at 25° C. As Table 3 indicates, permeability of the film is also affected by orientation of the film (which layer is exposed to the $CO_2$ gas first), and Relative Humidity. The walls were tested under conditions of low relative humidity (0%, representative of conditions inside the balloon upon fill) and high relative humidity (100%, representative of in vivo conditions). In certain embodiments, a composite wall having a permeability of <10 cc/m2/day is generally preferred; however, depending upon the desired effect of inflation and re-inflation by in vivo gasses such as $CO_2$, a higher permeability of >10 cc/m2/day in in vivo conditions can be desirable. For example, each of the films in the table can be suitable for use in various selected embodiments, such that the resulting balloon wall has a permeability to $CO_2$ of even greater than >10 cc/m2/day, e.g., >50 cc/m2/day, >100 cc/m2/day, >200 cc/m2/day, >300 cc/m2/day, >400 cc/m2/day, >500 cc/m2/day, >750 cc/m2/day, >1000 cc/m2/day, >1500 cc/m2/day, >2000 cc/m2/day, >2500 cc/m2/day, >3000 cc/m2/day, >3500 cc/m2/day, or even >4000 cc/m2/day. In selected embodiments, it is generally preferred to have a permeability of from about 1, 2, 3, 4, 5, 6, 7, 8, 9, or 10 cc/m2/day to about 15, 20, 25, 30, 35, 40, 45, 50, 60, 70, 80, 90, 100, 110, 120, 130, 140 or 150 cc/m2/day.

TABLE 3

| Film | Film Thickness (in) | Innermost Layer ($CO_2$ Exposed Layer) | RH % | Permeability Test Results (cc/m2/day) (1 ATM/37° C.) |
| --- | --- | --- | --- | --- |
| PE/EVOH/PE | 0.002 ± 0.001 | PE | 0 | 10.8 |
| 70% Nylon 6,66, 30% MXD6/ EVOH/PVDC/ 70% Nylon 6,66, 30% MXD6/ LLDPE + LDPE | 0.003 | Nylon 6,66 | 0 | 2.4 |

TABLE 3-continued

| Film | Film Thickness (in) | Innermost Layer ($CO_2$ Exposed Layer) | RH % | Permeability Test Results (cc/m2/day) (1 ATM/37° C.) |
|---|---|---|---|---|
| 70% Nylon 6,66, 30% MXD6/ EVOH/PVDC/ 70% Nylon 6,66, 30% MXD6/ LLDPE + LDPE | 0.003 | Nylon 6,66 | 95 ± 5 | 51.0 |
| 70% Nylon 6,66, 30% MXD6/ EVOH/PVDC/ 70% Nylon 6,66, 30% MXD6/ LLDPE + LDPE | 0.003 | LDPE | 95 ± 5 | 3.3 |
| 70% Nylon 6,66, 30% MXD6/PVDC/ 70% Nylon 6,66, 30% MXD6/ LLDPE + LDPE | 0.002 | LDPE | 0 | 43.0 |
| 70% Nylon 6,66, 30% MXD6/PVDC/ 70% Nylon 6,66, 30% MXD6/ LLDPE + LDPE | 0.003 | LDPE | 0 | 50.0 |
| 70% Nylon 6,66, 30% MXD6/PVDC/ 70% Nylon 6,66, 30% MXD6/ LLDPE + LDPE | 0.002 | LDPE | 95 ± 5 | 41.0 |
| 70% Nylon 6,66, 30% MXD6/PVDC/70% Nylon 6,66, 30% MXD6/LLDPE + LDPE | 0.003 | LDPE | 95 ± 5 | 49.0 |
| Bi-axially Oriented PP/EVOH/PE | 0.00125 | LDPE | 0 | 15.4 |
| Bi-axially Oriented PP/EVOH/PE | 0.00175 | PE | 0 | 8.2 |
| Bi-axially Oriented PP/EVOH/PE | 0.00125 | PE | 95 ± 5 | 282.6 |
| Bi-axially Oriented PP/EVOH/PE | 0.00125 | PE | 95 ± 5 | 1088.0 |
| Bi-axially Oriented PP/EVOH/PE | 0.00175 | PE | 95 ± 5 | 235.4 |
| Cast PP | 0.002 ± 0.001 | NA | 0 | 772.0 |
| Cast PP/PE/EVOH/PE | 0.0025 | PE | 0 | 7.2 |
| Cast PP/PE/EVOH/PE | 0.0025 | PE | 0 | 10.1 |
| Cast PP/PE/EVOH/PE | 0.0025 | PE | 95 ± 5 | 169.3 |
| Cast PP/PE/EVOH/PE | 0.0025 | PE | 95 ± 5 | 18.5 |
| Coextruded PE/EVOH/PE | 0.00125 | PE | 0 | 8.1 |
| Coextruded PE/EVOH/PE | 0.0015 | PE | 0 | 4.9 |
| Coextruded PET/SiOx/PE | 0.002 ± 0.001 | PE | 0 | 12.4 |
| CoExtrude-LLDPE/HDPE/EVOH/HDPE | 0.0025 | HDPE | 0 | 1.7 |
| HDPE/HDPE/PVdC/ EVOH/HDPE/ LLDPE + LDPE | 0.003 | HDPE | 0 | 5.0 |
| HDPE/HDPE/PVdC/ EVOH/HDPE/ LLDPE + LDPE | 0.003 | HDPE | 95 ± 5 | 6.8 |
| HDPE/HDPE/PVdC/ EVOH/HDPE/ LLDPE + LDPE | 0.003 | LDPE | 0 | 4.4 |
| HDPE/HDPE/PVdC/ EVOH/HDPE/ LLDPE + LDPE | 0.003 | LDPE | 95 ± 5 | 52.0 |
| HDPE/HDPE/PVdC/ HDPE/HDPE/ LLDPE + LDPE | 0.003 | LDPE | 0 | 74.0 |
| HDPE/HDPE/PVdC/ HDPE/HDPE/ LLDPE + LDPE | 0.003 | LDPE | 0 | 47.0 |

TABLE 3-continued

| Film | Film Thickness (in) | Innermost Layer ($CO_2$ Exposed Layer) | RH % | Permeability Test Results (cc/m2/day) (1 ATM/37° C.) |
|---|---|---|---|---|
| HDPE/HDPE/PVdC/ HDPE/HDPE/ LLDPE + LDPE | 0.003 | LDPE | 95 ± 5 | 68.0 |
| HDPE/HDPE/PVdC/ HDPE/HDPE/ LLDPE + LDPE | 0.003 | LDPE | 95 ± 5 | 44.0 |
| Kurarister ™ C, 3 mil | 0.003 | UNK | 0 | 3.2 |
| Nylon12/ PvDC/Nylon 12/LLDPE + LDPE | 0.003 | LLDPE + LDPE | 0 | 52.0 |
| Nylon12/ PvDC/Nylon 12/LLDPE + LDPE | 0.003 | LLDPE + LDPE | 95 ± 5 | 56.0 |
| MPI Supernyl LLDPE 40 μm | 0.0022 | LLDPE | 0 | 3.3 |
| MPI Supernyl LLDPE 40 μm | 0.0022 | LLDPE | 95 ± 5 | 5.8 |
| MPI Supernyl LLDPE 50 μm | 0.0026 | LLDPE | 0 | 4.2 |
| MPI Supernyl LLDPE 50 μm | 0.0026 | LLDPE | 95 ± 5 | 7.5 |
| Nylon12/ PvDC/Nylon 12/LLDPE + LDPE | 0.003 | LLDPE + LDPE | 0 | 59.3 |
| Nylon12/PVDC/ Nylon12/ LLDPE + LDPE | 0.003 | LLDPE + LDPE | 95 ± 5 | 29.5 |
| Nylon12/PVDC/ Nylon12/ LLDPE + LDPE- Thermoformed | 0.003 | LLDPE + LDPE | 0 | 73.2 |
| Nylon12/PVDC/ Nylon12/ LLDPE + LDPE | 0.0024 | LLDPE + LDPE | 0 | 77.0 |
| Nylon12/PVDC/ Nylon12/ LLDPE + LDPE | 0.0024 | LLDPE + LDPE | 95 ± 5 | 68.0 |
| Nylon12/PVdC/ Nylon12/LDPE-Cast | 0.003 | LDPE | 0 | 58.0 |
| Nylon12/Nylon Tie/ EVA/PVdC/Adhesive/ Nylon12/Nylon Tie/ LDPE-Cast | 0.003 | LDPE | 95 ± 5 | 54.0 |
| Nylon12/PVdC/ Nylon12/LDPE | 0.0035 | LDPE | 0 | 14.9 |
| Nylon12/ PVdC/Nylon12/ LDPE | 0.004 | LDPE | 0 | 34.0 |
| Nylon12/ PVdC/Nylon12/ LDPE | 0.0035 | LDPE | 95 ± 5 | 24.9 |
| Nylon12/ PVdC/Nylon12/ LDPE | 0.0035 | LDPE | 95 ± 5 | 41.3 |
| Nylon12/ PVdC/Nylon12/ LDPE | 0.004 | LDPE | 95 ± 5 | 31.7 |
| Nylon 6,66/ PVDC/Nylon6,66/ LLDPE + LDPE | 0.0024 | LDPE | 0 | 54.0 |
| Nylon 6,66/ PVDC/Nylon6,66/ LLDPE + LDPE | 0.0024 | LDPE | 95 ± 5 | 56.0 |
| Nylon 6,66/ EVOH/PVDC/ Nylon 6,66/LDPE | 0.0032 | LDPE | 0 | 5.5 |
| Nylon 6,66/ EVOH/PVDC/ Nylon 6,66/LDPE | 0.0032 | LDPE | 95 ± 5 | 6.4 |
| Nylon 6,66/ EVOH/PVDC/ Nylon 6,66/LDPE | 0.0032 | Nylon 6,66 | 95 ± 5 | 49.9 |

TABLE 3-continued

| Film | Film Thickness (in) | Innermost Layer ($CO_2$ Exposed Layer) | RH % | Permeability Test Results (cc/m2/day) (1 ATM/37° C.) |
|---|---|---|---|---|
| Nylon 6,66/PVDC/Nylon6,66/LLDPE + LDPE | 0.0027 | LDPE | 0 | 57.0 |
| Nylon 6,66/PVDC/Nylon6,66/LLDPE + LDPE | 0.003 | LDPE | 0 | 41.0 |
| Nylon 6,66/PVDC/Nylon6,66/LLDPE + LDPE | 0.0027 | LDPE | 95 ± 5 | 55.0 |
| Nylon 6,66/PVDC/Nylon6,66/LLDPE + LDPE | 0.003 | LDPE | 95 ± 5 | 46.0 |
| Multi-layer Nylon 12/LLDPE + LDPE | 0.0035 | LDPE | 0 | 3203.5 |
| Multi-layer Nylon 12/LLDPE + LDPE | 0.004 | LDPE | 0 | 2725.5 |
| Multi-layer Nylon 12/LLDPE + LDPE | 0.0045 | LDPE | 0 | 2553.6 |
| Multi-layer Nylon 12/LLDPE + LDPE | 0.0035 | LDPE | 95 ± 5 | 2539.3 |
| Multi-layer Nylon 12/LLDPE + LDPE | 0.004 | LDPE | 95 ± 5 | 2527.8 |
| Multi-layer Nylon 12/LLDPE + LDPE + Parylene | 0.0045 | LDPE | 0 | 1522.6 |
| Multi-layer Nylon 12/LLDPE + LDPE + Parylene | 0.0045 | LDPE | 95 ± 5 | 1275.5 |
| NYLON-SIOX/HDPE/LLDPE | 0.003 | LLDPE | 95 ± 5 | 83.0 |
| NYLON-SIOX/HDPE/LLDPE | 0.003 | LLDPE | 0 | 70.0 |
| Nylon-SIOX/LLDPE | 0.0015 | LLDPE | 0 | 134.0 |
| Nylon-SIOX/LLDPE | 0.0015 | LLDPE | 95 ± 5 | 82.0 |
| OPP Co-extrude with mPE/EVOH/mPE | 0.002 | mPE | 0 | 5.9 |
| OPP Laminated to mPE/EVOH/mPE | 0.0025 | mPE | 0 | 4.7 |
| OPP Laminated to mPE/EVOH/mPE | 0.003 | mPE | 0 | 3.4 |
| OPP Laminated to mPE/EVOH/mPE | 0.0025 | mPE | 95 ± 5 | 294.3 |
| OPP SIOX/LLDPE | 0.002 | LLDPE | 0 | 540.5 |
| OPP SIOX/LLDPE | 0.002 | LLDPE | 0 | 1081.0 |
| OPP SIOX/LLDPE | 0.002 | LLDPE | 95 ± 5 | 565.0 |
| OPP SIOX/LLDPE | 0.002 | LLDPE | 95 ± 5 | 594.5 |
| OPP/mPE/EVOH/mPE | 0.0021 | mPE | 0 | 5.0 |
| OPP/mPE/EVOH/mPE | 0.0021 | mPE | 95 ± 5 | 437.1 |
| OPP/PE/EVOH/PE | 0.0025 | OPP | 0 | 8.5 |
| OPP/PE/EVOH/PE | 0.0025 | OPP | 95 ± 5 | 11.6 |
| OPP/PE/EVOH/PE | 0.00175 | PE | 0 | 8.1 |
| OPP/PE/EVOH/PE | 0.0025 | PE | 0 | 8.9 |
| OPP/PE/EVOH/PE | 0.0025 | PE | 0 | 18.6 |
| OPP/PE/EVOH/PE | 0.0025 | PE | 95 ± 5 | 259.0 |
| OPP/PE/EVOH/PE | 0.0025 | PE | 95 ± 5 | 556.1 |
| OPP/PVDC/mPE | 0.0017 | mPE | 0 | 74.2 |
| OPP/PVDC/mPE | 0.0017 | mPE | 95 ± 5 | 84.6 |
| OPP-SIOX/LLDPE | 0.002 ± 0.001 | LLDPE | 95 ± 5 | 1159.7 |
| Oriented PA | 0.002 ± 0.001 | NA | 0 | 750.9 |
| Oriented PP | 0.002 ± 0.001 | NA | 0 | 726.0 |
| PA/EVOH/PA/LLDPE | 0.0022 | LLDPE | 0 | 5.0 |
| PA/EVOH/PA/LLDPE | 0.0022 | LLDPE | 0 | 3.1 |

TABLE 3-continued

| Film | Film Thickness (in) | Innermost Layer ($CO_2$ Exposed Layer) | RH % | Permeability Test Results (cc/m2/day) (1 ATM/37° C.) |
|---|---|---|---|---|
| PA/EVOH/PA/LLDPE | 0.0022 | LLDPE | 95 ± 5 | 10.8 |
| PE/EVOH/PE | 0.002 ± 0.001 | PE | 0 | 9.2 |
| PET | 0.001 | PE | 0 | 524.7 |
| SiOx-PET/EVOH/PE | 0.002 | PE | 0 | 1.4 |
| SiOx-PET/MPE/EVOH/mPE | 0.0016 | mPE | 0 | 1.0 |
| Si-Ox-PET/PE/EVOH/PE | 0.00125 | PE | 0 | 1.7 |
| Si-Ox-PET/PE/EVOH/PE | 0.0015 | PE | 0 | 1.6 |
| Si-Ox-PET/PE/EVOH/PE | 0.0015 | PE | 0 | 5.4 |
| Si-Ox-PET/PE/EVOH/PE | 0.002 | PE | 0 | 1.5 |
| Si-Ox-PET/PE/EVOH/PE | 0.002 | PE | 0 | 1.8 |
| Si-Ox-PET/PE/EVOH/PE | 0.002 | PE | 95 ± 5 | 22.6 |

Animal Studies

Two different composite walls were tested: a material (Nylon12/PvDC/Nylon 12/LLDPE+LDPE) with high barrier material characteristics and a material with low barrier characteristics (multi-layer Nylon12/LLDPE+LDPE). A series of experiments were performed using a mixture of 75% N2 and 25% CO2 as the balloon initial fill. As shown in the data of Table 4, each of the balloons maintained pressure over the duration tested, but gained substantially in volume. Considering the composite walls studied are not a metal canister (volume and pressure change due to material stretch) there was a significant change in the number of overall gas molecules inside the balloon from the initial gas fill. Since the internal balloon environment started with CO2 and nitrogen, most likely additional CO2 entered due to the environment the balloon was subjected to (N2 and CO2 headspace) but also most likely other gases available in the air as well as water vapor also diffused within the balloon wall.

Volume gains were higher for the barrier material composite walls than for the non-barrier walls. An analysis of gas in the balloons after explants (Tables 5a and 5b) showed gains in oxygen, hydrogen, and argon in addition to the nitrogen and carbon dioxide that was already present in the balloon at initial inflation. The balloons, both with a good barrier composite wall (table 5a) and a poor barrier composite wall (table 5b) both gained in overall volume while maintaining pressure after 30 days in vivo. Explant results of the balloon with a composite wall containing a good barrier material (#2, table 5a) showed a slightly higher increase in carbon dioxide than the wall without a barrier material (#3, table 5b). It is unlikely that nitrogen diffused in or out of the balloon due to its inertness as well as the external gastric environment most likely matched the internal concentration of nitrogen such that there was no (or an insignificant) diffusion gradient for the nitrogen gas.

TABLE 4

| Pig # | Balloon #, Wall Composition | Starting implant pressure (PSI) | Estd. Volume at implant | Explant Volume (cc) | Explant Pressure (PSI) | % $CO_2$ in balloon (meas. w/ $CO_2$ meter) | Measured % $CO_2$ in stomach gas (%) | Final Vol. | % gas gain (calc.) |
|---|---|---|---|---|---|---|---|---|---|
| 1 | 1, Barrier Material (Nylon/Saran) | 1.0 | 277 | 360 | 1.1 | 22% | 10% | 385 | 23.5 |
| 1 | 2, Barrier Material (Nylon/Saran) | 1.09 | 282 | 340 | 0.7 | 19.63% | 10% | 358 | 15 |
| 2 | 3, Non-Barrier Material (Nylon) | 1.15 | 283 | 330 | 1.2 | 26.57% | 8% | 320 | 14.5 |
| 2 | 4, Non-Barrier Material (Nylon) | 1.07 | 281 | 323 | 0.96 | 31% | 8% | 316 | 12.4 |

TABLE 5a

| Gas | % v/v, by MS | Detection Limit |
|---|---|---|
| Nitrogen | 64.04 | 0.01 |
| Oxygen | 7.63 | 0.01 |
| Argon | 0.60 | 0.01 |
| Carbon Dioxide | 19.63 | 0.01 |
| Hydrogen | 8.10 | 0.01 |
| Helium | not detected | 0.01 |
| Methane | not detected | 0.01 |

TABLE 5b

| Gas | % v/v, by MS | Detection Limit |
|---|---|---|
| Nitrogen | 62.33 | 0.01 |
| Oxygen | 9.27 | 0.01 |
| Argon | 0.7 | 0.01 |
| Carbon Dioxide | 26.57 | 0.01 |
| Hydrogen | 1.13 | 0.01 |
| Helium | not detected | 0.01 |
| Methane | not detected | 0.01 |

The data show that when it is desirable to minimize volume gain over the useful life of the device, a non-barrier composite wall material may be more desirable than a barrier wall. This observation is contrary to conventional wisdom that seeks to maintain the initial fill of gas in the balloon by maximizing barrier properties of the intragastric balloon wall.

Simulated Gastric Environment

Balloons constructed with non-barrier film composite walls were tested (multi-layer Nylon 12/LLDPE+LDPE) in a simulated gastric environment (tank containing a 1.2 pH HCl solution with NaCl and pepsin at 40° C. with a variable $N_2/CO_2$ headspace; samples were taken at peak $CO_2$ at 50% and trough $CO_2$ at 0% in the tank). The balloons were initially filled with either pure $N_2$ or a mixture of $N_2$ (75%) and $CO_2$ (25%), and pressure, volume, and gas gain were monitored over time. The balloon filled with pure nitrogen exhibited significantly higher gain of $CO_2$ when compared to the balloon filled with the $N_2/CO_2$ mixture. When a volume gain (as manifested in a gain of $CO_2$ gas) is desired, pure nitrogen as the initial fill gas in connection with a non-barrier film is desirable. Data for the experiments is provided in Table 6.

TABLE 6

| Expt. # | Material OGB # | Sample # | Balloon Internal Gas N2 or N2/CO2 | Pressure (Day 0) (psi) | Volume (Day 0) (cc) | Volume (Day 1) (cc) | Volume (Day 2) (cc) | Pressure (Day 2) (psi) |
|---|---|---|---|---|---|---|---|---|
| | | | End of Cycle → | | | | 50% $CO_2$ | 50% $CO_2$ |
| | | | | T = 0 | T = 0 | T = 1 | T = 2 | T = 2 |
| 1 | Non-Barrier Film | 1 | N2 | 1.12 | 304 | 312 | 314 | 1.84 |
| | | 3 | | 1.12 | 300 | 310 | 313 | 1.81 |
| | | 4 | | 1.09 | 294 | 309 | 311 | 1.79 |
| | | 5 | | 1.10 | 300 | 312 | 314 | 1.82 |
| | | 6 | | 1.10 | 309 | 317 | 320 | 1.68 |
| | | avg. | | 1.11 | 301 | 312 | 314 | 1.79 |
| 2 | | 1B | N2/CO2 (75%/25%) | 1.10 | 318 | 328 | 326 | 1.15 |
| | | 2B | | 1.00 | 295 | 301 | 299 | 1.04 |
| | | 4B | | 1.10 | 292 | 300 | 295 | 1.18 |
| | | 5B | | 1.08 | 294 | 306 | 303 | 1.22 |
| | | 6B | | 1.07 | 293 | 300 | 293 | 1.18 |
| | | avg. | | 1.07 | 298 | 307 | 303 | 1.15 |

| Expt. # | Material OGB # | Sample # | Balloon Internal Gas N2 or N2/CO2 | (Day 2) 9:00 AM (%) | Volume (Day 5) 9:00 am (cc) | Volume (Day 5) 7:00 PM (cc) | Pressure (Day 5) 7:00 PM (psi) | (Day 5) 7:00 PM (%) |
|---|---|---|---|---|---|---|---|---|
| | | | End of Cycle → | % Gas Gain | 50% $CO_2$ | 0% $CO_2$ | 0% $CO_2$ | % Gas Gain |
| | | | | T = 2 | T = 5 | T = 5 | T = 5 | T = 5 |
| 1 | Non-Barrier Film | 1 | N2 | 7.4% | 323 | 319 | 2.50 | 12.3% |
| | | 3 | | 8.2% | 319 | 314 | 2.53 | 12.3% |
| | | 4 | | 9.5% | 321 | 313 | 2.56 | 14.1% |
| | | 5 | | 8.6% | 324 | 318 | 2.70 | 14.3% |
| | | 6 | | 6.9% | 329 | 328 | 2.58 | 13.9% |
| | | avg. | | 8.1% | 323 | 318 | 2.57 | 13.4% |
| 2 | | 1B | N2/CO2 (75%/25%) | 2.1% | 329 | 324 | 1.37 | 2.6% |
| | | 2B | | 1.2% | 302 | 297 | 1.28 | 1.8% |
| | | 4B | | 1.1% | 299 | 293 | 1.25 | 1.0% |
| | | 5B | | 2.9% | 305 | 302 | 1.16 | 2.4% |
| | | 6B | | 0.5% | 298 | 295 | 1.26 | 1.4% |
| | | avg. | | 1.6% | 307 | 302 | 1.26 | 1.8% |

TABLE 6-continued

| Expt. # | Material | Sample # | Balloon Internal Gas | Volume (Day 6) 8:00 AM | Pressure (Day 6) 8:00 AM | (Day 6) 8:00 AM | Volume (Day 6) 7:00 PM | Pressure (Day 6) 7:00 PM |
|---|---|---|---|---|---|---|---|---|
| | | | End of Cycle → | 50% $CO_2$ | 50% $CO_2$ | % Gas Gain* | 0% $CO_2$ | 0% $CO_2$ |
| | | | | T = 6 (cc) | T = 6 (psi) | T = 6 (%) | T = 6 (cc) | T = 6 (psi) |
| 1 | Non-Barrier Film | 1 | $N_2$ | 323 | 3.03 | 16.0% | balloon cut during test | |
| | | 3 | | 320 | 3.01 | 16.3% | 318 | 2.84 |
| | | 4 | | 322 | 3.04 | 18.7% | 321 | 2.87 |
| | | 5 | | 322 | 3.19 | 17.7% | 322 | 2.98 |
| | | 6 | | 330 | 3.12 | 17.0% | 329 | 2.89 |
| | | avg. | | 323 | 3.08 | 17.1% | 323 | 2.90 |
| 2 | | 1B | $N_2/CO_2$ (75%/25%) | 329 | 1.82 | 5.7% | 329 | 1.48 |
| | | 2B | | 300 | 1.61 | 4.0% | 301 | 1.38 |
| | | 4B | | 299 | 1.64 | 4.2% | 298 | 1.46 |
| | | 5B | | 304 | 1.55 | 4.6% | 306 | 1.33 |
| | | 6B | | 299 | 1.62 | 4.0% | 298 | 1.41 |
| | | avg. | | 306 | 1.65 | 4.5% | 306 | 1.41 |

| Expt. # | Material | Sample # | Balloon Internal Gas | Volume (Day 6) 7:00 PM | Volume (Day 7) 8:00 AM | Pressure (Day 7) 8:00 AM | $CO_2$ % (Day 7) 8:00 AM | Volume (Day 7) 7:00 PM |
|---|---|---|---|---|---|---|---|---|
| | | | End of Cycle → | % Gas Gain | 50% $CO_2$ | 50% $CO_2$ | % Gas Gain* | 0% $CO_2$ |
| | | | | T = 6 (%) | T = 7 (cc) | T = 7 (psi) | T = 7 (%) | T = 7 (cc) |
| 1 | Non-Barrier Film | 1 | $N_2$ | balloon cut during test | | | | |
| | | 3 | | 14.9% | 322 | 3.02 | 16.8% | 319 |
| | | 4 | | 17.7% | 322 | 3.05 | 18.8% | 320 |
| | | 5 | | 16.7% | 325 | 3.15 | 18.3% | 323 |
| | | 6 | | 15.6% | 331 | 3.08 | 17.0% | 329 |
| | | avg. | | 16.2% | 325 | 3.08 | 17.7% | 323 |
| 2 | | 1B | $N_2/CO_2$ (75%/25%) | 4.2% | 327 | 1.63 | 4.4% | 326 |
| | | 2B | | 3.2% | 300 | 1.57 | 3.8% | 299 |
| | | 4B | | 3.1% | 299 | 1.61 | 4.0% | 296 |
| | | 5B | | 4.1% | 303 | 1.45 | 3.9% | 303 |
| | | 6B | | 2.8% | 300 | 1.60 | 4.1% | 297 |
| | | avg. | | 3.5% | 306 | 1.57 | 4.1% | 304 |

| Expt. # | Material | Sample # | Balloon Internal Gas | Pressure (Day 7) 7:00 PM | $CO_2$ % (Day 7) 7:00 PM | Volume (Day 8) 8:00 AM | Pressure (Day 8) 8:00 AM | $CO_2$ % (Day 8) 8:00 AM |
|---|---|---|---|---|---|---|---|---|
| | | | End of Cycle → | | | | 50% $CO_2$ | % Gas Gain |
| | | | | T = 7 | T = 7 (%) | T = 8 (cc) | T = 8 (psi) | T = 8 (%) |
| 1 | Non-Barrier Film | 1 | $N_2$ | 2.90 | 15.5% | balloon cut during test | | |
| | | 3 | | 2.92 | 17.7% | 322 | 3.01 | 16.8% |
| | | 4 | | 2.91 | 16.7% | 323 | 2.99 | 18.8% |
| | | 5 | | 2.88 | 15.6% | 325 | 3.07 | 17.9% |
| | | 6 | | 2.90 | 16.3% | 332 | 3.03 | 17.1% |
| | | avg. | | | | 326 | 3.03 | 17.6% |
| 2 | | 1B | $N_2/CO_2$ (75%/25%) | 1.42 | 3.3% | 329 | 1.43 | 4.0% |
| | | 2B | | 1.37 | 2.7% | 301 | 1.42 | 3.4% |
| | | 4B | | 1.37 | 2.3% | 299 | 1.29 | 2.6% |
| | | 5B | | 1.23 | 2.9% | 306 | 1.32 | 4.0% |
| | | 6B | | 1.42 | 2.6% | 299 | 1.43 | 3.1% |
| | | avg. | | 1.36 | 2.8% | 307 | 1.38 | 3.4% |

| Expt. # | Material | Sample # | Balloon Internal Gas | Volume (Day 8) 7:00 PM | Pressure (Day 8) 7:00 PM | $CO_2$ % (Day 8) 7:00 PM | Volume (Day 9) 8:00 AM | Pressure (Day 9) 8:00 AM |
|---|---|---|---|---|---|---|---|---|
| | | | End of Cycle → | 0% $CO_2$ | 0% $CO_2$ | % Gas Gain | 50% $CO_2$ | 50% $CO_2$ |
| | | | | T = 8 (cc) | T = 8 (psi) | T = 8 (%) | T = 9 (cc) | T = 9 (psi) |
| 1 | Non-Barrier | 1 | $N_2$ | balloon cut during test | | | | |
| | | 3 | | 318 | 2.88 | 15.1% | 323 | 2.96 |

TABLE 6-continued

| | | | | | | | | |
|---|---|---|---|---|---|---|---|---|
| | Film | 4 | | 322 | 2.87 | 17.9% | 323 | 3.00 |
| | | 5 | | 325 | 2.96 | 17.4% | 323 | 3.01 |
| | | 6 | | 330 | 2.88 | 15.8% | 332 | 2.91 |
| | | avg. | | 324 | 2.90 | 16.6% | 325 | 2.97 |
| 2 | | 1B | $N_2/CO_2$ | 325 | 1.30 | 2.5% | 327 | 1.28 |
| | | 2B | (75%/25%) | 314 | 1.28 | 5.8% | 301 | 1.35 |
| | | 4B | | 300 | 1.32 | 3.0% | 298 | 1.45 |
| | | 5B | | 304 | 1.23 | 3.2% | 307 | 1.35 |
| | | 6B | | 299 | 1.34 | 2.7% | 299 | 1.39 |
| | | avg. | | 308 | 1.29 | 3.4% | 306 | 1.36 |

| Expt. # | Material | Sample # | Balloon Internal Gas | $CO_2$ % (Day 9) 8:00 AM | Volume (Day 12) 8:00 AM | Pressure (Day 12) 8:00 AM | $CO_2$ % (Day 12) 8:00 AM | Volume (Day 13) 8:00 AM |
|---|---|---|---|---|---|---|---|---|
| End of Cycle → | | | | | | | % Gas Gain* | 50% CO2 |
| | | | | T = 9 (%) | T = 8 (cc) | T = 8 (psi) | T = 8 (%) | T = 9 (cc) |
| 1 | Non-Barrier Film | 1 | $N_2$ | | | balloon cut during test | | |
| | | 3 | | 16.8% | 323 | 3.00 | 17.0% | 325 |
| | | 4 | | 18.8% | 322 | 3.25 | 19.7% | 326 |
| | | 5 | | 17.1% | 325 | 3.27 | 18.8% | 327 |
| | | 6 | | 16.5% | 330 | 3.25 | 17.6% | 333 |
| | | avg. | | 17.3% | 325 | 3.19 | 18.3% | 328 |
| 2 | | 1B | $N_2/CO_2$ | 2.9% | 326 | 1.62 | 4.2% | 330 |
| | | 2B | (75%/25%) | 3.1% | 302 | 1.62 | 4.5% | 304 |
| | | 4B | | 3.1% | 298 | 1.42 | 3.0% | 300 |
| | | 5B | | 4.4% | 305 | 1.66 | 5.3% | 309 |
| | | 6B | | 3.0% | 298 | 1.58 | 3.6% | 298 |
| | | avg. | | 3.3% | 306 | 1.58 | 4.1% | 308 |

| Expt. # | Material | Sample # | Balloon Internal Gas | Pressure (Day 13) 8:00 AM | $CO_2$ % (Day 13) 8:00 AM | Volume (Day 14) 8:00 AM | Pressure (Day 14) 8:00 AM | $CO_2$ % (Day 14) 8:00 AM |
|---|---|---|---|---|---|---|---|---|
| End of Cycle → | | | | 50% CO2 | % Gas Gain* | 50% CO2 | 50% CO2 | % Gas Gain* |
| | | | | T = 9 (psi) | T = 9 (%) | T = 10 (cc) | T = 10 (psi) | T = 10 (%) |
| 1 | Non-Barrier Film | 1 | $N_2$ | | | | | |
| | | 3 | | 3.37 | 19.2% | 323 | 3.25 | 18.1% |
| | | 4 | | 3.36 | 21.2% | 327 | 3.21 | 20.7% |
| | | 5 | | 3.38 | 19.8% | 326 | 3.36 | 19.5% |
| | | 6 | | 3.30 | 18.5% | 334 | 3.30 | 18.8% |
| | | avg. | | 3.35 | 19.7% | 328 | 3.28 | 19.3% |
| 2 | | 1B | $N_2/CO_2$ | 1.68 | 5.3% | 329 | 1.68 | 5.1% |
| | | 2B | (75%/25%) | 1.69 | 5.3% | 302 | 1.48 | 3.9% |
| | | 4B | | 1.56 | 4.1% | 299 | 1.43 | 3.3% |
| | | 5B | | 1.69 | 6.3% | 307 | 1.57 | 5.3% |
| | | 6B | | 1.70 | 4.1% | 300 | 1.66 | 4.4% |
| | | avg. | | 1.66 | 5.0% | 307 | 1.56 | 4.4% |

Balloons constructed with various composite walls, a barrier material Nylon12/PvDC/Nylon12/LLDPE+LDPE) and a non-barrier material (multi-layer Nylon12/LLDPE+LDPE) were tested in a simulated gastric environment (tank containing a 1.2 pH HCl solution with NaCl and pepsin at 40° C. with a variable $N_2/CO_2$ headspace (75%/25% to 100%/0%)). The balloons were initially filled with a mixture of $N_2$ (75%) and $CO_2$ (25%). Pressure for the balloons fabricated from $CO_2$ barrier materials maintained pressure and volume over the time period tested, whereas the balloons fabricated from $CO_2$ non-barrier materials exhibited substantial pressure gain over the same time period, with a smaller volume gain. Results are presented in Table 7.

TABLE 7

| Exp. | Material | Sample | Balloon Internal Gas | Volume (Day 0) (cc) | Pressure (Day 0) (psi) | Volume (Day 1) (cc) | Pressure (Day 1) (psi) |
|---|---|---|---|---|---|---|---|
| 1 | Barrier | 1 | $N_2/CO_2$ (75%/25%) | | | 280 | 1.05 |
| | | 2 | | | | 279 | 1.03 |
| | | avg. | | | | 280 | 1.04 |

TABLE 7-continued

| Exp. | Material | Sample | Balloon Internal Gas | | | Volume (Day 1) (cc) | Pressure (Day 1) (psi) |
|---|---|---|---|---|---|---|---|
| 2 | Barrier | 1 | $N_2/CO_2$ (75%/25%) | | | 279 | 1.06 |
| | | 2 | | | | 278 | 1.07 |
| | | avg. | | | | 279 | 1.07 |
| 3 | Barrier | 1 | $N_2/CO_2$ (75%/25%) | | | 280 | 1.05 |
| | | 2 | | | | 278 | 1.02 |
| | | avg. | | | | 279 | 1.04 |
| 4 | Barrier | 1 | $N_2/CO_2$ (75%/25%) | | | 296 | 1.14 |
| | | 2 | | | | 295 | 1.05 |
| | | avg. | | | | 296 | 1.10 |
| 5 | Non-Barrier | 1 | $N_2/CO_2$ (75%/25%) | | | 304 | 1.12 |
| | | 2 | | | | 292 | 1.11 |
| | | avg. | | | | 298 | 1.12 |
| 6 | Non-Barrier | 1 | $N_2/CO_2$ (75%/25%) | | | 298 | 1.15 |
| | | 2 | | | | 294 | 1.14 |
| | | avg. | | | | 296 | 1.15 |
| 7 | Non-Barrier | 1 | $N_2/CO_2$ (75%/25%) | | | 297 | 1.14 |
| | | 2 | | | | 302 | 1.15 |
| | | avg. | | | | 300 | 1.15 |
| 8 | Barrier | 1 | $N_2/CO_2$ (75%/25%) | | | 298 | 1.11 |
| | | 2 | | | | 302 | 1.12 |
| | | avg. | | | | 300 | 1.12 |
| 9 | Barrier | 1 | $N_2/CO_2$ (75%/25%) | | | 294 | 1.18 |
| | | 2 | | | | 291 | 1.13 |
| | | avg. | | | | 293 | 1.16 |

| Exp. | Material | Sample | Balloon Internal Gas | Volume (Day 2) (cc) | Pressure (Day 2) (psi) | Volume (Day 3) (cc) | Pressure (Day 3) (psi) |
|---|---|---|---|---|---|---|---|
| 1 | Barrier | 1 | $N_2/CO_2$ (75%/25%) | | | 286 | 1.05 |
| | | 2 | | | | 284 | 1.01 |
| | | avg. | | | | 285 | 1.03 |
| 2 | Barrier | 1 | $N_2/CO_2$ (75%/25%) | | | 283 | 0.97 |
| | | 2 | | | | 282 | 1.04 |
| | | avg. | | | | 283 | 1.01 |
| 3 | Barrier | 1 | $N_2/CO_2$ (75%/25%) | | | 287 | 1.05 |
| | | 2 | | | | 280 | 0.97 |
| | | avg. | | | | 284 | 1.01 |
| 4 | Barrier | 1 | $N_2/CO_2$ (75%/25%) | | | 303 | 1.28 |
| | | 2 | | | | 303 | 1.18 |
| | | avg. | | | | 303 | 1.23 |
| 5 | Non-Barrier | 1 | $N_2/CO_2$ (75%/25%) | | | 313 | 2.26 |
| | | 2 | | | | 312 | 2.37 |
| | | avg. | | | | 313 | 2.32 |
| 6 | Non-Barrier | 1 | $N_2/CO_2$ (75%/25%) | | | 308 | 2.34 |
| | | 2 | | | | 301 | 2.15 |
| | | avg. | | | | 305 | 2.25 |
| 7 | Non-Barrier | 1 | $N_2/CO_2$ (75%/25%) | | | 307 | 2.17 |
| | | 2 | | | | 312 | 2.22 |
| | | avg. | | | | 310 | 2.20 |
| 8 | Barrier | 1 | $N_2/CO_2$ (75%/25%) | | | 303 | 1.28 |
| | | 2 | | | | 303 | 1.28 |
| | | avg. | | | | 303 | 1.28 |
| 9 | Barrier | 1 | $N_2/CO_2$ (75%/25%) | | | 301 | 1.24 |
| | | 2 | | | | 298 | 1.24 |
| | | avg. | | | | 300 | 1.24 |

| Exp. | Material | Sample | Balloon Internal Gas | Volume (Day 4) (cc) | Pressure (Day 4) (psi) | Volume (Day 5) (cc) | Pressure (Day 5) (psi) |
|---|---|---|---|---|---|---|---|
| 1 | Barrier | 1 | $N_2/CO_2$ (75%/25%) | 289 | 1.08 | 292 | 1.07 |
| | | 2 | | 287 | 1.03 | 292 | 1.04 |
| | | avg. | | 288 | 1.06 | 292 | 1.06 |
| 2 | Barrier | 1 | $N_2/CO_2$ (75%/25%) | 284 | 1.14 | 287 | 1.01 |
| | | 2 | | 286 | 1.13 | 287 | 1.02 |
| | | avg. | | 285 | 1.14 | 287 | 1.02 |
| 3 | Barrier | 1 | $N_2/CO_2$ (75%/25%) | 285 | 1.09 | 287 | 1.05 |
| | | 2 | | 285 | 1.05 | 286 | 1.00 |
| | | avg. | | 285 | 1.07 | 287 | 1.03 |
| 4 | Barrier | 1 | $N_2/CO_2$ (75%/25%) | 308 | 1.35 | 309 | 1.36 |
| | | 2 | | 306 | 1.39 | 306 | 1.29 |
| | | avg. | | 307 | 1.37 | 308 | 1.33 |
| 5 | Non-Barrier | 1 | $N_2/CO_2$ (75%/25%) | 320 | 2.44 | 322 | 2.51 |
| | | 2 | | 315 | 2.59 | 315 | 2.58 |
| | | avg. | | 318 | 2.52 | 319 | 2.55 |
| 6 | Non-Barrier | 1 | $N_2/CO_2$ (75%/25%) | 311 | 2.48 | 312 | 2.59 |
| | | 2 | | 306 | 2.39 | 308 | 2.51 |
| | | avg. | | 309 | 2.44 | 310 | 2.55 |

TABLE 7-continued

| | | | | | | | |
|---|---|---|---|---|---|---|---|
| 7 | Non-Barrier | 1 | $N_2/CO_2$ (75%/25%) | 310 | 2.43 | 308 | 2.45 |
| | | 2 | | 315 | 2.43 | 316 | 2.54 |
| | | avg. | | 313 | 2.43 | 312 | 2.50 |
| 8 | Barrier | 1 | $N_2/CO_2$ (75%/25%) | 305 | 1.39 | 305 | 1.36 |
| | | 2 | | 303 | 1.34 | 306 | 1.31 |
| | | avg. | | 304 | 1.37 | 306 | 1.34 |
| 9 | Barrier | 1 | $N_2/CO_2$ (75%/25%) | 303 | 1.30 | 304 | 1.29 |
| | | 2 | | 298 | 1.35 | 299 | 1.33 |
| | | avg. | | 301 | 1.33 | 302 | 1.31 |

Balloons constructed with composite walls with high $CO_2$ barrier properties (Experiments 1, 2, and 3) (Nylon12/PvDC/Nylon 12/LLDPE+LDPE) and walls having a higher permeability to $CO_2$ (Experiments 4, 5, and 6) consisting of multi-layer Nylon12/LLDPE+LDPE were exposed to a stimulated gastric environment. The simulated gastric environment comprised a tank containing a 1.2 pH HCl solution with NaCl and pepsin at 40° C. The headspace in the tank was cycled from a gas mixture comprising 75% $N_2$/25% $CO_2$ headspace to one comprising 100% $N_2$/0% $CO_2$. The balloons were initially filled with various mixtures of $N_2$ and $CO_2$, and volume was monitored. Data regarding volume changes are provided in Table 8. The balloons constructed using walls having a higher permeability to $CO_2$ gained substantially in volume compared to those with high $CO_2$ barrier properties. For the balloons constructed using walls having a higher permeability to $CO_2$, those with higher ratios of $N_2$ to $CO_2$ as initial fill gas gained less volume than those with lower ratios of $N_2$ to $CO_2$. The data demonstrate that permeation of $CO_2$ into balloons fabricated with walls having a higher permeability to $CO_2$ occurs quickly in the gastric environment, and that this process can be employed to assist with inflation in the early stages of implant.

TABLE 8

| Experiment | Material | Sample | Balloon Internal Gas | Volume (Day 1) 5:00 PM (cc) | Pressure (Day 1) 5:00 PM (psi) | Volume (Day 2) 8:00 AM (cc) | Pressure (Day 2) 8:00 AM (psi) |
|---|---|---|---|---|---|---|---|
| 1 | Barrier | 1 | N2/CO2 | 298 | 1.07 | 301 | 1.08 |
| | | 2 | (92%/8%) | 293 | 1.02 | 293 | 1.06 |
| | | 3 | | 285 | 1.00 | 287 | 1.05 |
| | | avg. | | 296 | 1.05 | 297 | 1.07 |
| 2 | Barrier | 1 | N2/CO2 | 286 | 1.09 | 287 | 1.09 |
| | | 2 | (90%/10%) | 291 | 1.09 | 294 | 1.14 |
| | | 3 | | 293 | 1.08 | 298 | 1.13 |
| | | avg. | | 290 | 1.09 | 304 | 1.20 |
| 3 | Barrier | 1 | N2/CO2 | 290 | 1.10 | 295 | 1.15 |
| | | 2 | (85%/15%) | 290 | 1.02 | 290 | 1.03 |
| | | 3 | | 299 | 1.16 | 304 | 1.20 |
| | | avg. | | 293 | 1.09 | 293 | 1.09 |
| 4 | Non-Barrier | 1 | N2/CO2 | 290 | 1.04 | 298 | 1.54 |
| | | 2 | (92%/8%) | 292 | 1.07 | 300 | 1.60 |
| | | 3 | | 291 | 1.09 | 301 | 1.68 |
| | | avg. | | 291 | 1.07 | 299 | 1.57 |
| 5 | Non-Barrier | 1 | N2/CO2 | 283 | 1.07 | 293 | 1.64 |
| | | 2 | (90%/10%) | 287 | 1.05 | 295 | 1.60 |
| | | 3 | | 290 | 1.00 | 300 | 1.48 |
| | | avg. | | 287 | 1.04 | 294 | 1.62 |
| 6 | Non-Barrier | 1 | N2/CO2 | 287 | 1.06 | 297 | 1.76 |
| | | 2 | (85%/15%) | 298 | 1.07 | 307 | 1.66 |
| | | 3 | | 290 | 1.13 | 304 | 1.78 |
| | | avg. | | 292 | 1.09 | 302 | 1.71 |

| Experiment | Material | Sample | Balloon Internal Gas | Volume (Day 2) 8:30 PM (cc) | Pressure (Day 2) 8:30 PM (psi) | Volume (Day 3) 8 AM (cc) | Pressure (Day 3) 8 AM (psi) |
|---|---|---|---|---|---|---|---|
| 1 | Barrier | 1 | N2/CO2 | 301 | 1.11 | 301 | 1.13 |
| | | 2 | (92%/8%) | 295 | 1.06 | 302 | 1.10 |
| | | 3 | | 284 | 1.03 | 289 | 1.07 |
| | | avg. | | 298 | 1.09 | 302 | 1.12 |
| 2 | Barrier | 1 | N2/CO2 | 287 | 1.13 | 287 | 1.12 |
| | | 2 | (90%/10%) | 294 | 1.13 | 296 | 1.17 |
| | | 3 | | 297 | 1.15 | 300 | 1.19 |
| | | avg. | | 293 | 1.14 | 294 | 1.16 |
| 3 | Barrier | 1 | N2/CO2 | 294 | 1.17 | 297 | 1.21 |
| | | 2 | (85%/15%) | 290 | 1.08 | 294 | 1.10 |
| | | 3 | | 302 | 1.27 | 308 | 1.27 |
| | | avg. | | 295 | 1.17 | 300 | 1.19 |

TABLE 8-continued

| | | | | | | | |
|---|---|---|---|---|---|---|---|
| 4 | Non-Barrier | 1 | N2/CO2 (92%/8%) | 296 | 1.48 | 297 | 1.72 |
| | | 2 | | 298 | 1.55 | 302 | 1.81 |
| | | 3 | | 296 | 1.65 | 301 | 1.80 |
| | | avg. | | 297 | 1.56 | 300 | 1.78 |
| 5 | Non-Barrier | 1 | N2/CO2 (90%/10%) | 291 | 1.56 | 294 | 1.80 |
| | | 2 | | 295 | 1.50 | 295 | 1.67 |
| | | 3 | | 298 | 1.44 | 301 | 1.65 |
| | | avg. | | 293 | 1.53 | 297 | 1.71 |
| 6 | Non-Barrier | 1 | N2/CO2 (85%/15%) | 295 | 1.76 | 300 | 1.99 |

Human Gastric Environment

Balloons constructed with non-barrier film composite walls were tested in vivo in 10 patients in a clinical study for 30 days. The balloon wall comprised multi-layer Nylon 12/LLDPE+LDPE. One balloon per patient was administered. Balloons were filled with a mixed gas to approximately 245 cc with an average starting balloon pressure of 1.01 psi above atmosphere. The initial fill gas was 95% Nitrogen and 5% $CO_2$. At the end of 30 days, balloons remained full and firm, although ending pressure and volumes could not be discerned visually/endoscopically. Of the 10 balloons retrieved, 10 balloons had internal gas samples obtained, and 8 provided meaningful data. Table 9 provides the data retrieved from the balloons. The end gas samples are reflective of the gastric environment and are averaged as follows: 82.4% $N_2$, 10.6% $O_2$, 5.9% $CO_2$, and 0.84% Ar. Thus, the internal balloon environment reflects that of the average gastric environment gas concentrations. Data for the experiments is provided in Table 9.

TABLE 9

| Patient # | Starting Balloon Gas Concentration | | Ending Balloon Gas Concentration (% v/v, by MS) | | | |
|---|---|---|---|---|---|---|
| Patient # | [N2] | [CO$_2$] | [N2] | [O$_2$] | [CO$_2$] | [Ar] |
| 1 | 95.00 | 5.00 | 81.19 | 10.20 | 7.60 | 0.86 |
| 2 | 95.00 | 5.00 | 81.24 | 12.90 | 4.85 | 0.86 |
| 3 | 95.00 | 5.00 | 82.41 | 10.80 | 5.65 | 0.85 |
| 4 | 95.00 | 5.00 | 82.07 | 11.20 | 5.70 | 0.82 |
| 5 | 95.00 | 5.00 | 82.87 | 10.05 | 6.00 | 0.82 |
| 6 | 95.00 | 5.00 | 82.54 | 11.50 | 4.80 | 0.88 |
| 7 | 95.00 | 5.00 | | Erroneous Sample | | |
| 8 | 95.00 | 5.00 | 81.76 | 10.20 | 7.00 | 0.82 |
| 9 | 95.00 | 5.00 | | Erroneous Sample | | |
| 10 | 95.00 | 5.00 | 84.95 | 8.20 | 5.80 | 0.81 |
| Avg. | | | 82.38 | 10.63 | 5.93 | 0.84 |
| Std Dev | | | 1.20 | 1.36 | 0.97 | 0.03 |
| Max | | | 84.95 | 12.90 | 7.60 | 0.88 |
| Min | | | 81.19 | 8.20 | 4.80 | 0.81 |

In certain embodiments wherein it is desirable to maintain the starting pressure and volume of the device, this can be accomplished by matching the internal balloon environment at implant (i.e., the fill gases) closely to the gastric environment. In such embodiments, the balloon can be inflated with an initial gas fill gas comprising approximately 80-85% nitrogen, 8-12% oxygen, and 4-8% carbon dioxide. The concentration of argon and other in vivo gases can be considered inconsequential to the total volume/pressure, and may be omitted for convenience or included as desirable. To encourage inflation of the balloon in vivo, the starting concentrations of oxygen and/or carbon dioxide can be reduced.

Exemplary Balloon Systems and Balloons

Intragastric Balloon System 1: An intragastric balloon system, the system comprising: an intragastric balloon; at least two wires in communication with a surface of a wall of the intragastric balloon; and an electronics package configured to facilitate a supply of current to the at least two wires.

Intragastric Balloon System 2: Intragastric Balloon System 1, wherein the electronics package is configured to complete a circuit between the at least two wires.

Intragastric Balloon System 3: Intragastric Balloon System 2, wherein the electronics package comprises a switch, wherein the electronics package is configured to complete a circuit between the least two wires by activating the switch.

Intragastric Balloon System 4: Intragastric Balloon System 3, wherein the at least two wires comprise a copper wire and an aluminum wire, wherein the system further comprises a saline solution in communication with the at least two wires.

Intragastric Balloon System 5: Intragastric Balloon System 1, wherein the at least two wires are embedded within a weld of the balloon.

Intragastric Balloon System 6: Intragastric Balloon System 1, wherein the electronics package comprises a timer, wherein the electronics package is configured to facilitate the supply of current to the at least two wires at a predetermined time or after a predetermined amount of time.

Intragastric Balloon System 7: Intragastric Balloon System 1, wherein the electronics package further comprises a communications module, the communications module configured to receive data from an external device.

Intragastric Balloon System 8: Intragastric Balloon System 7, wherein the electronics package is configured to receive an instruction to initiate the supply of current to the at least two wires from the external device.

Intragastric Balloon System 9: Intragastric Balloon System 1, wherein the intragastric balloon comprises a uni-directional polymer film.

Intragastric Balloon 10: An intragastric balloon comprising a uni-directional polymer film, the uni-directional polymer film comprising a plurality of polymer molecules oriented along a longitudinal axis.

Intragastric Balloon 11: Intragastric Balloon 10, wherein the uni-directional polymer film is embedded within a seam of the intragastric balloon.

Intragastric Balloon 12: Intragastric Balloon 10, further comprising an erodible material in communication with the uni-directional polymer film, the erodible material configured to erode in the gastric environment over a period of time, wherein erosion of the erodible material is configured to form one or more holes in the uni-directional polymer film.

Intragastric Balloon 13: Intragastric Balloon 10, further comprising an electronics package, the electronics package configured to initiate the formation of one or more holes in the uni-directional polymer film.

Intragastric Balloon 14: Intragastric Balloon 13, wherein the electronics package further comprises a timer, wherein the electronics package is configured to initiate the formation of one or more holes in the uni-directional polymer film at a predetermined time or after a predetermined amount of time.

Intragastric Balloon 15: Intragastric Balloon 13, wherein the electronics package further comprises a communications module, the communications module configured to receive data from an external device.

Intragastric Balloon 16: Intragastric Balloon 15, wherein the communications module is configured to receive an instruction to initiate the formation of one or more holes in the uni-directional film from the external device.

The present invention has been described above with reference to specific embodiments. However, other embodiments than the above described are equally possible within the scope of the invention. Different method steps than those described above may be provided within the scope of the invention. The different features and steps of the invention may be combined in other combinations than those described. The scope of the invention is only limited by the appended patent claims.

All references cited herein are incorporated herein by reference in their entirety. To the extent publications and patents or patent applications incorporated by reference contradict the disclosure contained in the specification, the specification is intended to supersede and/or take precedence over any such contradictory material.

To the extent publications and patents or patent applications incorporated by reference herein contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, unless otherwise expressly stated, should be construed as open ended as opposed to limiting. As examples of the foregoing, the term 'including' should be read to mean 'including, without limitation' or the like; the term 'comprising' as used herein is synonymous with 'including,' 'containing,' or 'characterized by,' and is inclusive or open-ended and does not exclude additional, unrecited elements or method steps; the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise. In addition, as used in this application, the articles 'a' and 'an' should be construed as referring to one or more than one (i.e., to at least one) of the grammatical objects of the article. By way of example, 'an element' means one element or more than one element.

The presence in some instances of broadening words and phrases such as 'one or more', 'at least', 'but not limited to', or other like phrases shall not be read to mean that the narrower case is intended or required in instances where such broadening phrases may be absent.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. An intragastric balloon system, the system comprising:
   an intragastric balloon, the intragastric balloon having a top half, a bottom half, a seam connecting the top half and the bottom half, and a head;
   at least two wires imbedded in the seam of the intragastric balloon; and
   an electronics package positioned within the seam and comprising a processor configured to perform logical operations to provide power to the at least two wires or to complete a circuit with the at least two wires such that a supply of current to the at least two wires is generated, wherein the wires are adapted such that the current generates heat that melts or burns one or more portions of the seam of the intragastric balloon, whereby the structural integrity of the seam of the intragastric balloon is compromised such that the intragastric balloon deflates.

2. The intragastric balloon system of claim 1, wherein the electronics package is configured to complete a circuit between the at least two wires.

3. The intragastric balloon system of claim 2, wherein the electronics package comprises a switch, wherein the electronics package is configured to complete a circuit between the at least two wires by activating the switch.

4. The intragastric balloon system of claim 3, wherein the at least two wires comprise a copper wire and an aluminum wire, wherein the system further comprises a saline solution in communication with the at least two wires.

5. The intragastric balloon system of claim 1, wherein the electronics package comprises a timer, wherein the electronics package is configured to facilitate the supply of current to the at least two wires at a predetermined time or after a predetermined amount of time.

6. The intragastric balloon system of claim 1, wherein the electronics package further comprises a communications module, the communications module comprising a receiver configured to receive data in a form of an RF signal, a magnetic signal, or an ultrasound signal from an external device.

7. The intragastric balloon system of claim 6, wherein the electronics package is configured to receive an instruction to initiate the supply of current to the at least two wires from the external device.

8. The intragastric balloon system of claim 1, wherein the intragastric balloon comprises a uni-directional polymer film.

9. An intragastric balloon, comprising:
a wall enclosing a lumen, the wall comprising a top half, a bottom half, a weld, and a valve, the wall comprising a uni-directional polymer film incorporated into the weld of the intragastric balloon, the uni-directional polymer film comprising a plurality of polymer molecules oriented along a longitudinal axis so as to allow the film, in response to application of a shear force, to readily tear into multiple separate pieces along the longitudinal axis but not perpendicularly to the longitudinal axis;
a self-sealing valve system adapted for addition of an inflation fluid to the lumen; and
an erodible material in communication with the uni-directional polymer film, the erodible material configured to erode in the gastric environment over a period of time, wherein erosion of the erodible material is configured to form one or more holes in the uni-directional polymer film such that, in response to application of a shear force, the film readily tears into multiple separate pieces along the longitudinal axis but not perpendicularly to the longitudinal axis, such that the intragastric balloon deflates.

10. The intragastric balloon system of claim 1, wherein the at least two wires are configured to burn through all of a longitudinal segment of the seam, causing the intragastric balloon to break into at least two separate pieces.

11. The intragastric balloon system of claim 10, wherein a rupture of the seam severs the top half from the bottom half of the intragastric balloon.

12. The intragastric balloon system of claim 10, wherein the intragastric balloon comprises additional wires embedded in additional seams, folds, or welds adapted to break the intragastric balloon into a plurality of smaller balloon pieces.

13. The intragastric balloon system of claim 10, having an inverted configuration.

14. The intragastric balloon system of claim 10, having a noninverted or overlapped configuration.

15. The intragastric balloon system of claim 10, wherein the at least two wires are composed of a metal that readily dissolves in stomach acid.

16. The intragastric balloon system of claim 10, wherein the electronics package is configured to activate a switch and/or a power source if the intragastric balloon receives a premature tear or puncture allowing stomach acid to enter the interior of the balloon.

17. The intragastric balloon system of claim 9, wherein each of the multiple separated pieces are smaller than the size of a fully formed deflated balloon and have no capacity to trap a liquid in comparison to a fully formed deflated balloon.

18. The intragastric balloon system of claim 9, having an inverted configuration.

19. The intragastric balloon system of claim 9, having a noninverted or overlapped configuration.

\* \* \* \* \*